(12) United States Patent
Zhu et al.

(10) Patent No.: US 10,596,553 B2
(45) Date of Patent: Mar. 24, 2020

(54) METHODS, CATALYSTS, AND DEVICES FOR BIOLOGICAL OBJECT DEGRADATION

(71) Applicant: JIANGSU SIJIA BIOMASS TECHNOLOGY CO., LTD., Suzhou, Jiangsu (CN)

(72) Inventors: Jianliang Zhu, Jiangsu (CN); Wenliang Wu, Jiangsu (CN)

(73) Assignee: JIANGSU SIJIA BIOMASS TECHNOLOGY CO., LTD., Suzhou (CN)

(*) Notice: Subject to any disclaimer, the term of this patent is extended or adjusted under 35 U.S.C. 154(b) by 0 days.

(21) Appl. No.: 16/322,959

(22) PCT Filed: Aug. 3, 2016

(86) PCT No.: PCT/CN2016/093031
§ 371 (c)(1),
(2) Date: Feb. 3, 2019

(87) PCT Pub. No.: WO2018/023474
PCT Pub. Date: Feb. 8, 2018

(65) Prior Publication Data
US 2019/0184378 A1    Jun. 20, 2019

(51) Int. Cl.
*B01J 3/00* (2006.01)
*B01J 21/04* (2006.01)
(Continued)

(52) U.S. Cl.
CPC ............... *B01J 23/72* (2013.01); *B01J 3/00* (2013.01); *B01J 21/04* (2013.01); *B01J 21/08* (2013.01);
(Continued)

(58) Field of Classification Search
CPC ..... B01J 3/00; B01J 23/00; B01J 23/70; B01J 23/72; C07C 29/00; C07C 29/132;
(Continued)

(56) References Cited

U.S. PATENT DOCUMENTS

2012/0172588 A1    7/2012  Qiao et al.
2012/0197029 A1*   8/2012  Hwang ............... B01J 23/72
                                                   549/266
(Continued)

FOREIGN PATENT DOCUMENTS

CN    101619227 A    1/2010
CN    102898278 A    1/2013
(Continued)

OTHER PUBLICATIONS

International Search Report in PCT/CN2016/093031 dated Apr. 27, 2017, 6 pages.
(Continued)

*Primary Examiner* — Natasha E Young
(74) *Attorney, Agent, or Firm* — Metis IP LLC

(57) ABSTRACT

The present disclosure provides a method for biological object degradation. The method may include: providing a first biological object; providing a catalyst that forms a mixture with the first biological object and includes a copper element; and obtaining a first liquid phase and a first solid phase by heating the mixture in an atmosphere including hydrogen. The first liquid phase may include a sugar. The present disclosure also provides a system and a catalyst for biological object degradation.

19 Claims, 18 Drawing Sheets

(51) Int. Cl.
*B01J 21/08* (2006.01)
*B01J 23/72* (2006.01)
*B01J 23/75* (2006.01)
*B01J 37/18* (2006.01)
*C07C 29/141* (2006.01)
*C07C 29/74* (2006.01)
*C07C 31/20* (2006.01)
*C07C 31/22* (2006.01)
*C10B 53/02* (2006.01)
*B01J 23/755* (2006.01)

(52) U.S. Cl.
CPC .............. *B01J 23/755* (2013.01); *B01J 37/18* (2013.01); *C07C 29/141* (2013.01); *C07C 29/74* (2013.01); *C07C 31/202* (2013.01); *C07C 31/205* (2013.01); *C07C 31/225* (2013.01); *C10B 53/02* (2013.01)

(58) Field of Classification Search
CPC ..... C07C 29/136; C07C 29/14; C07C 29/141; C07C 29/74; C07C 31/00; C07C 31/18; C07C 31/20; C07C 31/202; C07C 31/205; C07C 31/225; C10B 53/00; C10B 53/02
See application file for complete search history.

(56) References Cited

U.S. PATENT DOCUMENTS

| | | |
|---|---|---|
| 2013/0052682 A1 | 2/2013 | Medoff et al. |
| 2014/0007862 A1 | 1/2014 | Fujita |
| 2014/0060522 A1 | 3/2014 | Baynes et al. |

FOREIGN PATENT DOCUMENTS

| | | |
|---|---|---|
| CN | 102921426 A | 2/2013 |
| CN | 104073533 A | 10/2014 |
| EP | 2374903 A1 | 10/2011 |

OTHER PUBLICATIONS

He Li, The Preparation and Characterization of Cu-Based Catalyst and the Study on Catalytic Hydrogenation of Cellulose, 2011.

* cited by examiner

FIG. 2

```
Obtaining a mixture of air including dust and biological object      ~ 310
particles by pulverizing the biological object
                            ↓
Feeding the biological object particles into a stirring tank         ~ 320
                            ↓
Trapping at least a portion of the dust when the air including the   ~ 330
dust passes through a cyclone separator
                            ↓
Obtaining filtered air after the remaining air including dust passes ~ 340
through a bag filter
```

FIG. 3

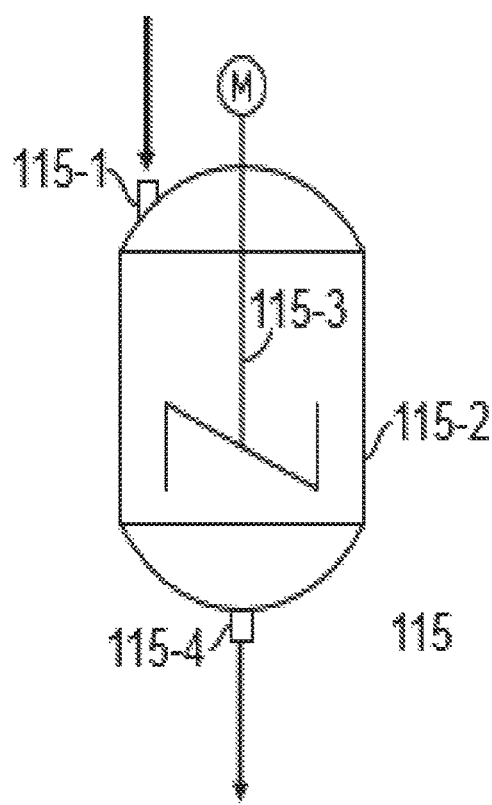
FIG. 6
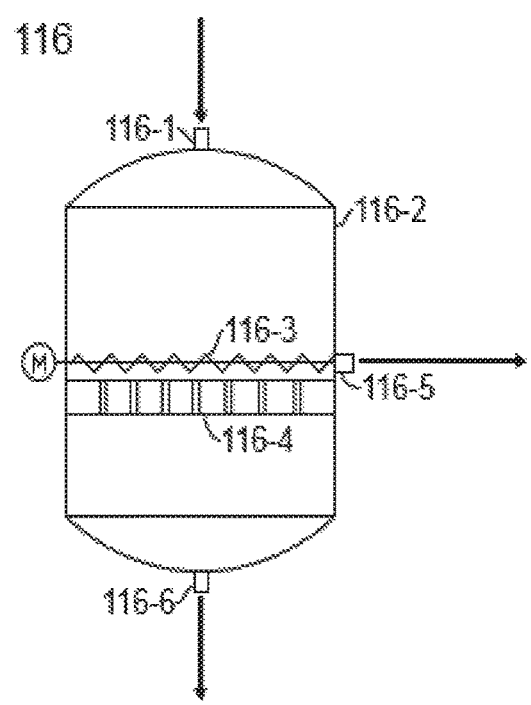
FIG. 7-A

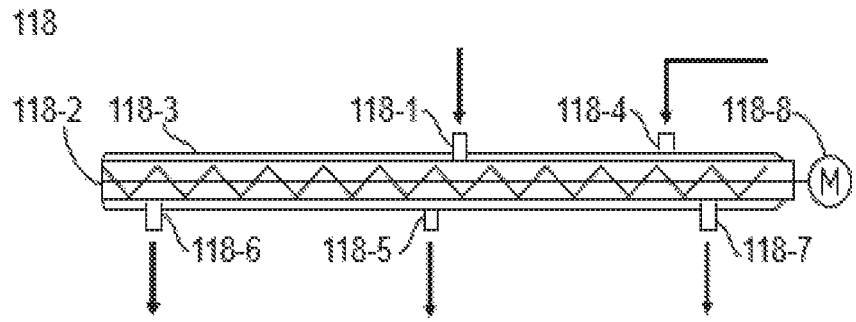
FIG. 7-B
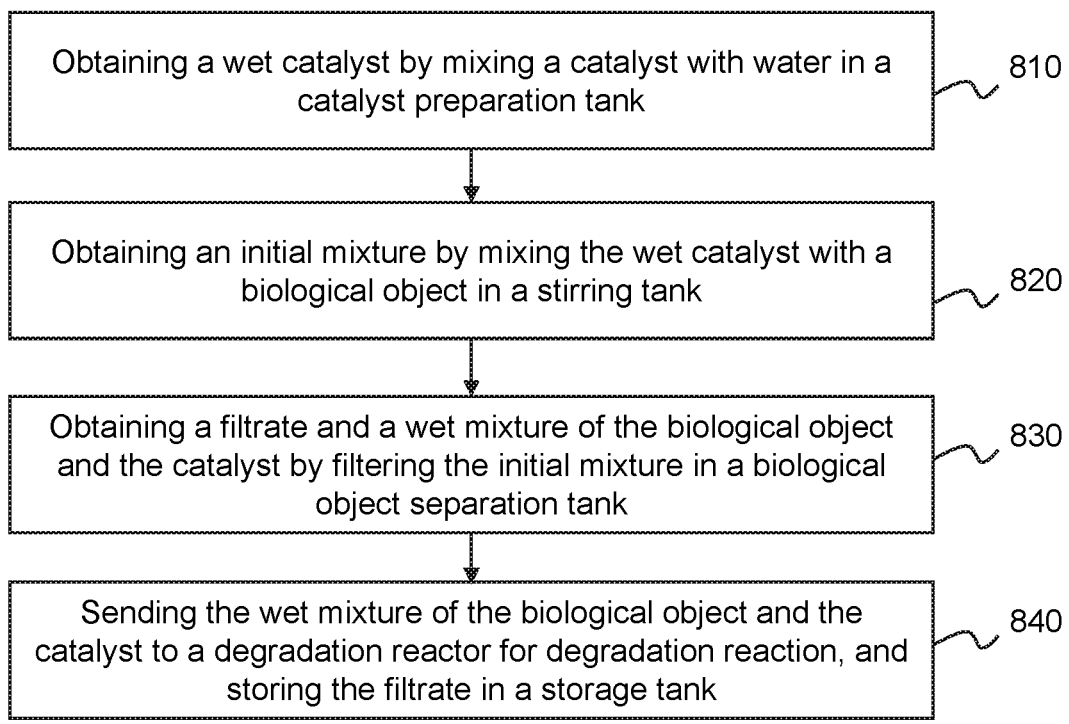
FIG. 8-A

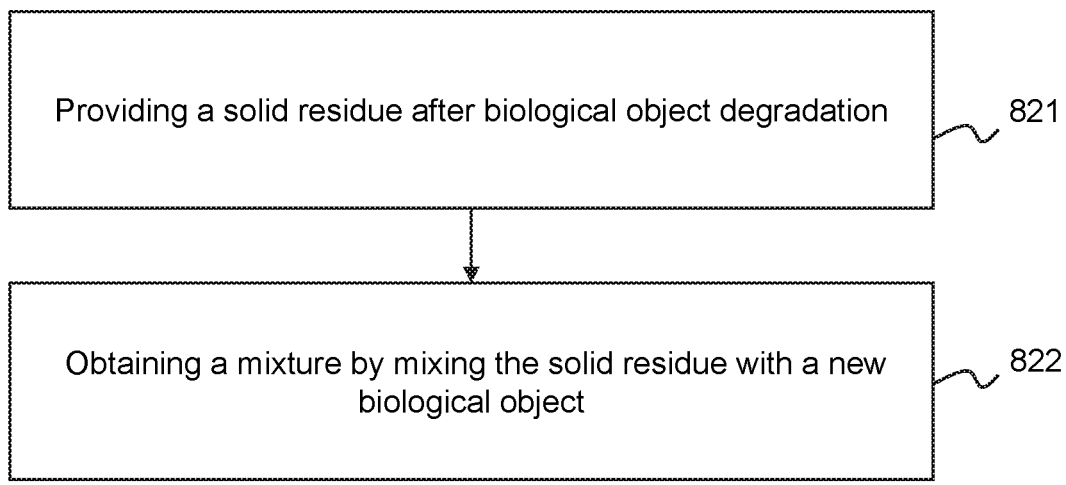
FIG. 8-B
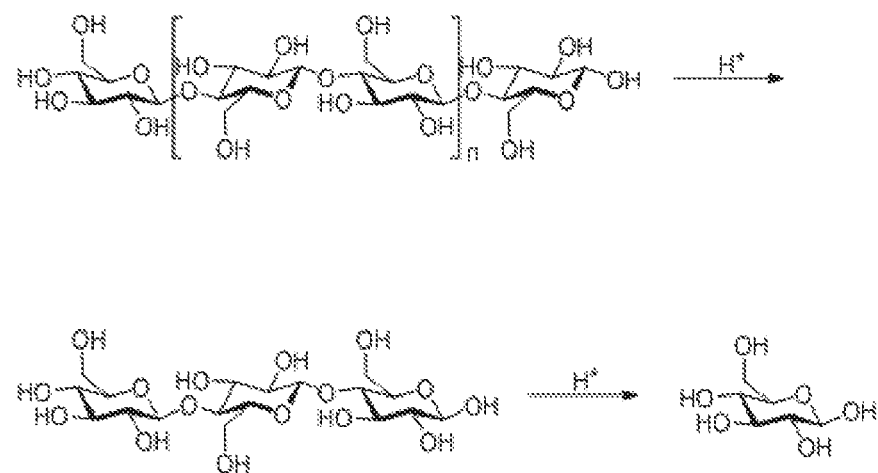
FIG. 8-C

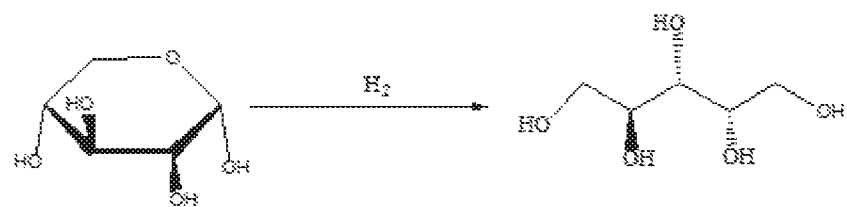
FIG. 20-A
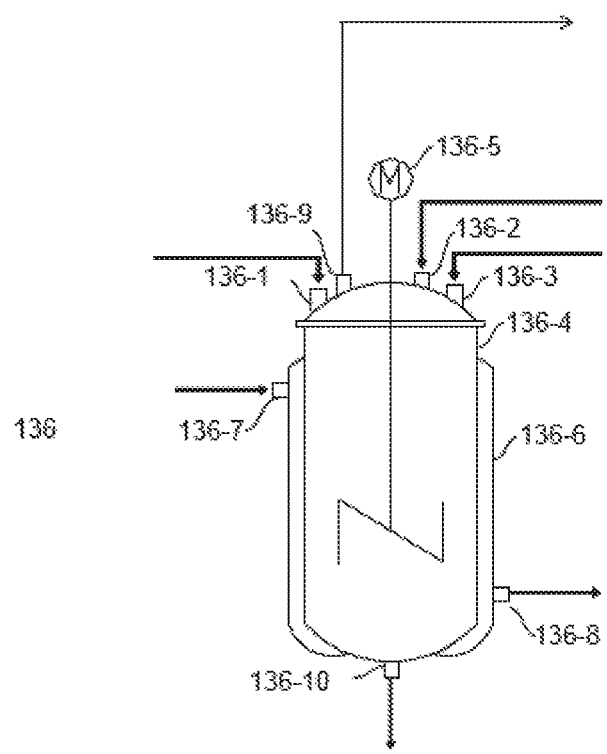
FIG. 20-B

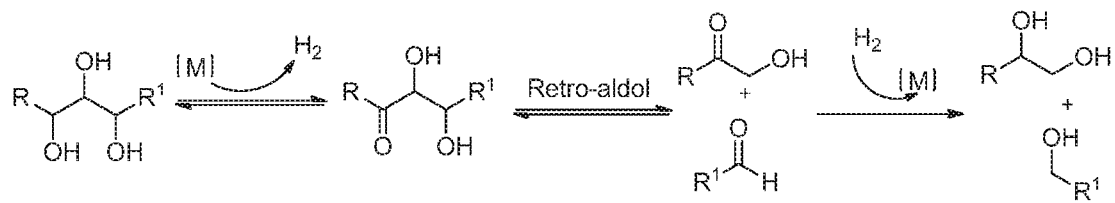
FIG. 25-A
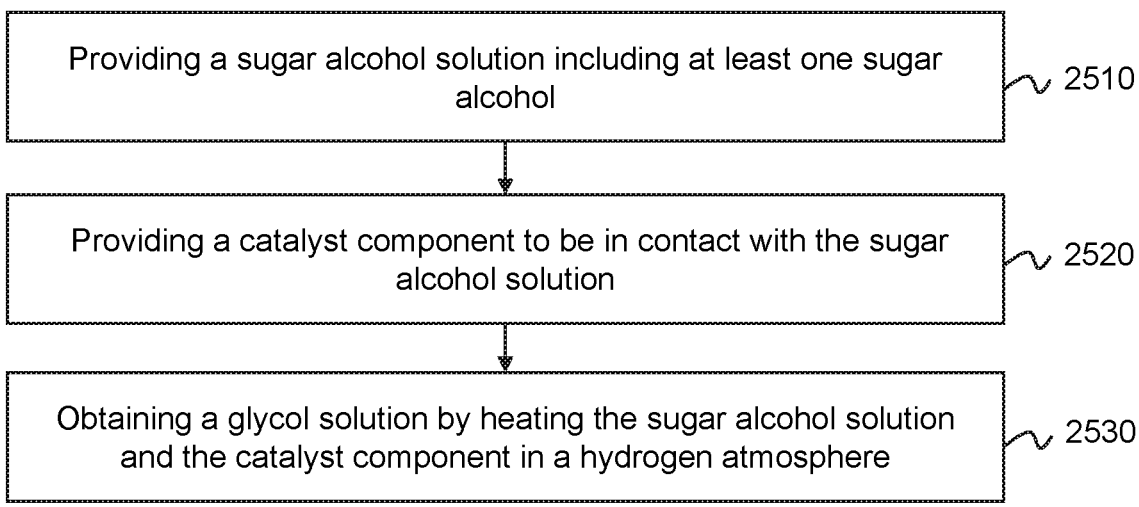
FIG. 25-B

METHODS, CATALYSTS, AND DEVICES FOR BIOLOGICAL OBJECT DEGRADATION

CROSS-REFERENCE TO RELATED APPLICATIONS

This application is a U.S. national stage under 35 U.S.C. § 371 of International Application No. PCT/CN2016/093031, now WO 2018/023474 A1, filed on Aug. 3, 2016, designating the United States of America, the entire contents of which are incorporated herein by reference.

TECHNICAL FIELD

The present disclosure relates to the field of processing biological objects, and more particularly, to methods, catalysts, and devices for biological object degradation.

BACKGROUND

As the energy shortage and environmental pollution is increasing, people are looking for new energy resources to replace non-renewable resources such as fossil fuels. Biological objects are the fourth largest energy resource after coal, oil, and natural gas. There are many types of biological objects, including straw, forestry waste, weeds and so on. As a traditional biological object energy resource, straw is rich in polysaccharides, proteins, fats, and other organic compounds, and also includes a large amount of nitrogen, phosphorus, potassium, and other nutrients. The polysaccharides in straw are mainly cellulose and hemicellulose, accounting for about 70% to 80%. Cellulose and hemicellulose may be used in papermaking, packaging materials processing, environmental protection products, production of alcohol and xylitol, and so on. Straw is rich in nutrients such as nitrogen, phosphorus, and potassium, which may be used as green fertilizer in farmland and woodland to promote the growth of plants.

By biological or chemical methods, biological objects such as straw may be processed to obtain fuels, inorganic salts, and chemical raw materials. The utilization of straw not only saves resources and energy, but also reduces the harm to the environment. Therefore, it is desirable to provide methods for comprehensively utilizing the organic and inorganic components of biological objects.

SUMMARY

One aspect of the present disclosure relates to a method for biological object degradation. The method may include: providing a first biological object; providing a catalyst, the catalyst and the biological object forming a mixture and the catalyst including a copper element; and obtaining a first liquid phase and a first solid phase by heating the mixture in an atmosphere including hydrogen, the first liquid phase including a sugar. According to some embodiments of the present disclosure, the method may further include filtering the mixture. According to some embodiments of the present disclosure, the method may further include providing a second biological object; mixing the second biological object with the solid phase residue; obtaining a second solution and a second solid phase by heating the second biological object components and the solid phase residue in an atmosphere including hydrogen, the second solution including a sugar.

One aspect of the present disclosure relates to a system for biological object degradation. The system may include a first reactor. The first reactor may include: a first chamber, a first feed port, a first heating device, a first discharge port, and a second discharge port. The first chamber may be configured to hold a mixture. The mixture may include biological object and catalyst. The first chamber may be in an atmosphere including hydrogen. The first feed port may be configured to deliver the mixture. The first heating device may be configured to heat the mixture to obtain a first liquid phase containing sugar and a first solid phase containing catalyst. The first discharge port may be configured to discharge the first liquid phase, and the second discharge port may be configured to discharge the first solid phase. According to some embodiments of the present disclosure, the system may further include a stirring device. According to some embodiments of the present disclosure, the system may further include a second reactor. The second reactor may include a second chamber, a second heating device, a second feed port, a third discharge port, and a fourth discharge port. The second chamber may be configured to hold a second mixed material. The second mixed material may include at least the first solid phase. The second heating device may be configured to heat the second mixed material to obtain a second liquid phase containing sugar and a second solid phase containing catalyst. The third discharge port may be configured to discharge the second liquid phase. The fourth discharge port may be configured to discharge the second solid phase. The second discharge port may be connected with the second feed port and receive the first solid phase.

According to some embodiments of the present disclosure, the catalyst may include at least one of copper, copper oxide, and cuprous oxide. According to some embodiments of the present disclosure, the catalyst may include an auxiliary agent. According to some embodiments of the present disclosure, the auxiliary agent may be silicon dioxide.

According to some embodiments of the present disclosure, the first biological object may be preprocessed. According to some embodiments of the present disclosure, the pre-processing operation may include at least one of cutting, pulverizing, grinding, and drying.

According to some embodiments of the present disclosure, the mass ratio of the catalyst to the first biological object may be in the range of 1:100 to 200:100.

According to some embodiments of the present disclosure, the atmosphere including hydrogen may have a pressure in the range of 1.0 MPa to 6.0 MPa. According to some embodiments of the present disclosure, the atmosphere including hydrogen may have a pressure in the range of 1.0 MPa to 4.0 MPa.

According to some embodiments of the present disclosure, heating the mixture may be carried out in the range of 100° C. to 170° C.

According to some embodiments of the present disclosure, the heating of the mixture may last from 0.5 hours to 20.0 hours. According to some embodiments of the present disclosure, the heating of the mixture may be accompanied by stirring of the mixture. According to some embodiments of the present disclosure, the stirring speed may be in the range of 400 rpm to 800 rpm. The present disclosure also provides a catalyst for biological object degradation. The catalyst may include a copper-containing component. The copper-containing component may have a mass percentage of 4.8% to 100%. The auxiliary agent may have a mass percentage of 0% to 95.2% and a particle size in the range of 0.5 mm to 32 mm.

Some of the additional features of the present disclosure may be explained in the following description. Some of the additional features of the present disclosure will be apparent to those skilled in the art from a review of the following description and the accompanying drawings. The characteristics disclosed by the present disclosure may be realized and achieved by the practice or use of the methods, means and combinations of the various aspects of the specific embodiments described below.

BRIEF DESCRIPTION OF THE DRAWINGS

The drawings described herein are provided to provide a further understanding of the present disclosure, which form a part of the present disclosure. The illustrative embodiments of the present disclosure and the description thereof are used to explain the present disclosure and do not constitute a limitation of the present disclosure. The same reference numerals represent similar structures throughout the several views of the drawings.

FIG. 2 is a shematic diagram illustrating an exemplary biological object preprocessing device according to some embodiments of the present disclosure FIG. 3 is a flowchart illustrating an exemplary process for preprocessing a biological object according to some embodiments of the present disclosure

FIG. 6 is a shematic diagram illustrating an exemplary feeding tank according to some embodiments of the present disclosure.

FIG. 7-A is a shematic diagram illustrating an exemplary biological object feeding tank with solid-liquid separation according to some embodiments of the present disclosure.

FIG. 7-B is a shematic diagram illustrating an exemplary dispensing device according to some embodiments of the present disclosure.

FIG. 8-A is a flowchart illustrating an exemplary process for feeding a biological object according to some embodiments of the present disclosure.

FIG. 8-B is a flowchart illustrating an exemplary process for mixing new materials and old materials according to some embodiments of the present disclosure.

FIG. 8-C is a shematic diagram illustrating an exemplary hydrolysis mechanism of cellulose according to some embodiments of the present disclosure.

FIG. 20-A illustrates a reaction formula of hydrogenation of xylose to generate xylitol according to some embodiments of the present disclosure.

FIG. 20-B is a shematic diagram illustrating an exemplary hydrogenation reactor according to some embodiments of the present disclosure.

FIG. 25-A is a schematic diagram illustrating an exemplary cracking mechanism of sugar alcohol according to some embodiments of the present disclosure.

FIG. 25-B is a flowchart illustrating an exemplary process for sugar alcohol cracking according to some embodiments of the present disclosure.

DETAILED DESCRIPTION

Figure 1:
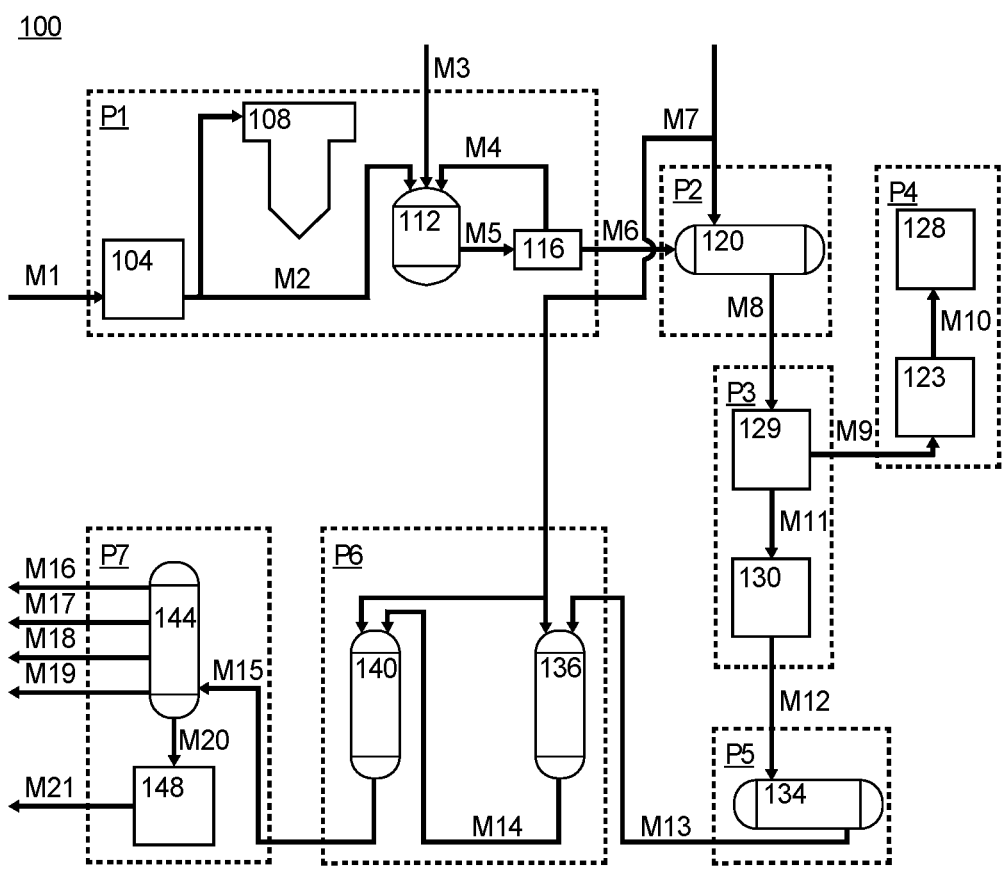
FIG. 1 is a shematic diagram illustrating an exemplary biological object processing system according to some embodiments of the present disclosure.

In order to more clearly illustrate the technical solutions of the embodiments of the present disclosure, a brief description of the drawings used in the description of the embodiments will be briefly made below. Obviously, the drawings in the following description are only some examples or embodiments of the present disclosure. For those skilled in the art, the present disclosure may also be applied to other similar scenarios in accordance with these figures without the inventive effort. Unless the context is obvious or otherwise stated, the same reference numerals in the figures represent similar structures or operations.

Before any embodiment of the present disclosure is described in detail, it is to be understood that the present disclosure is not limited in its application to the structural details and the arrangement of the components as described in the following description or the following figures. The present disclosure may have other embodiments and may be operated or implemented in a variety of ways. It is to be understood that the phraseology and terminology used herein is for the purpose of description and should not be construed as limiting. As used in the present disclosure and the appended claims, the singular forms "a," "an," and "the" include plural referents unless the content clearly dictates otherwise. As used herein, "including," "comprising" or "having" and variations thereof are intended to cover the items listed thereafter and their equivalents as well as additional items. These projects do not constitute an exclusive list, and methods or apparatus may also contain other projects. Unless otherwise stated or limited, the terms "connected" and "coupled" and variations thereof are used broadly to encompass both direct and indirect connections and couplings. For example, an entry of a device may be directly connected with an exit of another device, or an indirect connection between the entry of the device and the exit of another device may be established through a pipe. In addition, "connected" and "coupled" are not restricted to physical or mechanical connections or couplings. It is understood that other embodiments may be utilized to make structural or logical changes without departing from the scope of the disclosure. In addition, terms such as "front," "rear," "top," and "bottom" are used only to describe that the elements are related to each other, and are not intended to limit, indicate or imply the necessary orientation of the apparatus. Unless otherwise stated or limited, the terms "discharge port" and "feed port" may have a valve. The flow or delivery of materials may be allowed or prevented by opening or closing the valve. Unless otherwise stated, "particle size" refers to a diameter of particles.

Flowcharts are used in the present disclosure to illustrate the operations performed by the system in accordance with an embodiment of the present disclosure. It should be understood that the preceding or the following operations are not necessarily performed precisely in order. Instead, the various steps may be processed in reverse order or simultaneously. At the same time, one or more operations may be added to or removed from these processes.

Embodiments of the system or method of the present disclosure may be applied to various application scenarios such as biological object refineries, biological object treatment plants, domestic garbage disposal stations, and so on.

For example, embodiments of the systems or methods of the present disclosure may be applied to treating biological object resources including sugars (e.g., polysaccharides, etc.) to obtain products having application value, including, for example, a variety of industrial chemical products and/or raw materials.

The biological object described in the present disclosure refers to organic substances derived from living organisms. Biological objects may be used as a source of energy and chemicals. As an energy source, the biological object may be directly converted into various forms of biofuels that may generate heat by combustion, or be indirectly converted into biofuels by thermal, chemical and biochemical methods. As a source of chemicals, the biological object may be directly or indirectly converted into various forms of chemicals by hydrolysis, alcoholysis, aminolysis, cracking, oxidation, reduction, fermentation, and other chemical reactions.

The sources of the biological object may be substances rich in organics, such as forestry resources, agricultural resources, domestic sewage, industrial organic wastewater, city solid waste, and manure of livestock and poultry, etc. Forestry resources may include scattered wood, residual leaves, branches, and fruit shells, etc. Agricultural resources may include crop straw (such as corn straw, sorghum straw, wheat straw, rice straw, soybean straw, and cotton straw), and waste of agriculture and processing industry (such as rice husks remaining in the agricultural production process, etc). Domestic sewage may include various types of drainage from the living of urban residents, commercial industries, and service industries, such as cooling water, bath drainage, washing drainage, laundry drainage, kitchen drainage, and other sewage. Industrial organic wastewater may include wastewater discharged during the production process of alcohol, brewing, sugar, food, pharmaceutical, paper, and slaughter industries. City solid waste may include domestic waste of urban residents, commercial industries, and service industries, and a small amount of construction waste.

The common biological object may include wood, starch (wheat, corn, mung beans, potatoes, cassava, etc.), cotton and linen fiber, agricultural and forestry waste (bark, straw, weeds), food residue (such as arthropod exoskeleton including chitin and chitosan, etc.).

Woody plants, herbs, ferns, and bryophytes may provide a large number of biological object resources. Woody plants may include trees (such as pine, fir, maple, poplar, alfalfa, etc.) and shrubs (tea, rose, hibiscus, etc.), subshrubs (peony, etc.); herbs may include annual herbs (such as rice, gourd, morning glory, aster, corn, sorghum, etc.), biennial herbs (such as wheat, beets, broad beans, etc.), and perennial herbs (such as bamboo, sweet potato, chrysanthemum, lotus, etc.). Ferns may include selaginella, cymbidium, Chinese leeches, or the like. The bryophytes may include liverworts, lichens, gourd moss, or the like. Algae may include spirulina, green algae, cyanobacteria, diatoms, red algae, kelp, seaweed, etc.

Straw refers to the stem of mature crops and is natural materials including polysaccharides. The straw may include cellulose, hemicellulose, lignin, soluble sugar, crude protein, inorganic salt, silica, or the like. Straw may include rice straw, bagasse, branches, leaves, bamboo leaves, bamboo stems, hemp, wheat straw, corn stover, sorghum, weeds, water hyacinth, etc.

Polysaccharide is a polymer obtained by dehydration polymerization of a plurality of monosaccharide molecules. The dehydrated monosaccharide molecules are linked by glycosidic bonds in the polysaccharide. Polysaccharides may have straight chains or long chains with branches. Polysaccharides may hydrolyze to generate monosaccharides or oligosaccharides. Polysaccharides may include starch, glycogen (muscle glycogen, hepatic glycogen), various heteropolysaccharides, hemicellulose, cellulose, or the like. In the present disclosure, the biological object may include materials existing in different forms, such as biological object particles obtained by pulverization.

The monosaccharide constituting the polysaccharide may include glucose, fructose, galactose, mannose, rhamnose, arabinose, xylose, henna sugar, ribose, deoxyribose, glyceraldehyde, dihydroxyacetone, erythrose, lyxose, sedoheptulose, idose, and so on.

Polysaccharides may be divided into homogeneous polysaccharides and heterogeneous polysaccharides according to the type of monosaccharides. The homogeneous polysaccharide refers to a polysaccharide composed of one kind of monosaccharide molecules. The homogeneous polysaccharide may include starch, glycogen, cellulose, chitosan, polyfructose, polygalactose, etc., which is composed of glucose. Starch and glycogen are storage forms of glucose in plants and animals, respectively. Cellulose is the main structural component of plant cells. The heterogeneous polysaccharide refers to a polysaccharide formed by the condensation of different monosaccharide molecules. Heterogeneous polysaccharides may include hyaluronic acid, chondroitin sulfate, or the like.

Cellulose is a polysaccharide composed of β-D-glucose that is linked by β-1,4-glycosidic bonds. The cellulose is a linear polymer, and is the main ingredients of plant cell walls. Cellulose is mainly derived from vascular plants, ground plants, and a part of algae cell walls, such as cotton, wood, hemp, wheat straw, bagasse, or the like. Cellulose may include crystalline cellulose and amorphous cellulose. Crystalline cellulose refers to partially depolymerized cellulose in which all of the hydroxyl groups in the molecular chain form intramolecular hydrogen bonds or intermolecular hydrogen bonds without free hydroxyl groups. In amorphous cellulose, only a part of the hydroxyl groups form hydrogen bonds, and there are many free hydroxyl groups.

Hemicellulose is a heterogeneous polysaccharide composed of several different pentoses and hexose with a degree of polymerization of about 200. Monosaccharides constituting hemicellulose may include xylose, glucose, arabinose, mannose, galactose, rhamnose, or the like. Hemicellulose formed by the condensation of these monosaccharides may include xylan, polygalactose glucose mannose, polyarabose galactose, polyglucose mannose, or the like.

Lignin is an aromatic polymer with a molecular structure including oxyphenylpropanol or a derivative structural unit thereof. Lignin is widely present in plants. The dry matter ratio of the lignin of the herb and the woody plant may be 20% to 32%. Lignin may be present in the cell walls of conducting tissue cells, marrow, roots, fruits, shoots, bark, and cork layers, etc. In terms of quantity, lignin is mostly present in the secondary cell wall, but the quantity is higher in the intermediate layer. By coupling with hemicellulose, lignin is combined with a plurality of cellulosic fibers to create a more rigid structure, especially with increased flexural strength. Lignin may be polymerized from three basic phenylpropane structural monomers (p-coumaryl alcohol, coniferyl alcohol, and sinapyl alcohol), mainly generating three kinds of lignin including p-hydroxyphenylpropane lignin, guaiacyl lignin, and syringyl lignin. Lignin may be divided into native lignin and separated lignin. The native lignin is insoluble in any solvent, and the native lignin is an aggregate with many polar groups, especially with many hydroxyl groups, causing intramolecular and intermolecular hydrogen bonds. The separated lignin has a change in its solubility properties due to condensation and degradation. According to solubility, the separated lignin may be divided into sulfuric acid lignin, hydrochloric acid lignin, copper oxide ammonia lignin, periodic acid lignin, alkali lignin, ethanol lignin, sulfur lignin, phenol lignin, organic amine lignin, or the like.

Preprocessing may refer to a transformation of the size, shape, structure, composition, etc. of the raw materials to a certain extent through physical, chemical or biological processes.

Physical pretreatment may include pulverizing the materials using mechanical, acoustic, ultrasonic, radiation, high temperature, steam, or the like. Mechanical treatment may include shearing, milling, rolling, tearing, milling, or the like. For example, in the process of mechanical pulverization, the cell walls of dead cells in a biological object are destroyed, resulting in an increase in the specific surface area of the particles and obtaining particles of different sizes. The particles may be sieved through sieves of different mesh numbers.

The chemical pretreatment may include dehydration, drying, solvent extraction, acid-base treatment, oxidation, and so on, which may change the structure and morphology of raw materials and make cellulose more conductive to degradation. For example, alkaline degradation may partially break the glycosidic bond of cellulose, and decrease the degree of polymerization of cellulose.

The biological pretreatment may be a process in which the raw materials is partially degraded by a fermentation process of microorganism, resulting in polysaccharides with a low molecular weight and intermediate products, making cellulose easier to be decomposed. For example, cellulase digestion pretreatment utilizes the interaction of cellulase with cellulose to cause the long molecular chain of the fiber forming the crystal structure to be cracked, and to cause the end of the long chain molecule to be free, thereby making the cellulose easy to hydrate. As another example, the endonuclease may act on the exo-enzyme-activated cellulose, and decompose the β-1,4 bond to generate a short-chain oligosaccharide such as cellobiose or trisaccharide. As another example, the lignin-degrading microorganisms are used to degrade the lignin in the biological object, thereby increasing the enzymatic saccharification rate of cellulose and hemicellulose.

Degradation refers to a process in which the number of carbon atoms in an organic compound molecule is reduced and the molecular weight is decreased. In the present disclosure, degradation refers to a process in which under the action of chemical or physical methods, the cellulose or hemicellulose in the biological object undergoes functional group conversion, which causes a decrease in degree of polymerization, and breakage of carbon-carbon bonds or carbon-oxygen bonds in glucose groups, thereby generating various monosaccharides, oligosaccharides or other polysaccharides. The degradation method of cellulose may include an acid method, an alkali method, an enzymatic method, a critical water degradation method, an ionic liquid degradation method, an oxidative degradation method, a hydrodegradation method, or the like. Different degradation methods may generate different products. Hemicellulose is easier to be degraded and the degradation conditions are relatively mild. At least part of the cellulose degradation method may be applied to the degradation of hemicellulose.

Monosaccharides produced by biological object degradation may include xylose, arabinose, and glucose.

Xylose is a pentacarbonal aldosaccharide. Xylose is widely present in plants in the form of xylan and is one of the main monosaccharides after hemicellulose hydrolysis. Xylose is widely used. For example, xylitol may be produced by hydrogenation reduction of xylose. Arabinose is a pentacarbonal aldosaccharide. Arabinose is mainly present in hemicellulose and pectin in the form of a polymer and is one of the main monosaccharides after hemicellulose hydrolysis. Glucose is a kind of hexose aldose, which is a monosaccharide widely distributed in nature and is ubiquitous in cellulose and hemicellulose.

Sugar alcohol refers to a polyol formed by reduction of an aldehyde group or a ketone carbonyl group of a saccharide to a hydroxyl group. Sugar alcohols may be prepared from sugars by reduction or hydrogenation. Sugar alcohols are usually prepared by catalytic reduction of sugars with sodium borohydride, sodium amalgam or Raney nickle in laboratories. Industrially, a production method of sugar alcohols is a high-pressure catalytic hydrogenation reduction in the presence of nickel or an electrolytic reduction in an alkaline medium.

Sugar alcohols are in small amounts in nature. It is generally colorless crystal and soluble in water. Common sugar alcohols are xylitol, arabitol, and sorbitol, etc. Xylitol is a pentacarbonitol. Industrially, xylitol may be obtained by hydrogenation of xylose. Xylitol may be used as a non-caloric sweetener in food. Algalitol is a pentacarbonitol. The arabitol may be obtained by hydrogenation reduction of arabinose or lysine. Sorbitol is a hexacarbohydrate alcohol. Sorbitol may be obtained by hydrogenation reduction of glucose. Sorbitol may be used as a sweetener in place of sugar in food.

Hydrogenation or hydrogenated reaction is a chemical reduction reaction carried out using hydrogen and a compound. The hydrogenation or hydrogenated reaction may be carried out in the presence of certain metal catalysts. The hydrogenation or hydrogenated reaction may be used to produce certain organic compounds. For example, in the present disclosure, xylose, glucose, and arabinose are hydrogenated to obtain xylitol, sorbitol, and arabitol.

Cracking or cracking reaction is a thermochemical decomposition reaction of organics under high temperature conditions. Due to the presence of the catalyst, the reaction temperature of the cracking or cracking reaction may be reduced, and the conversion rate of some cracking productions may be increased.

Coking refers to a process in which a carbonaceous substance is converted to coke or porous carbon under certain conditions (e.g., a higher temperature). In the present disclosure, coking may refer to the chemical reaction of dehydration and pyrolysis of organics (such as monosaccharides) at high temperatures.

Under certain conditions, monosaccharides may be dehydrated to generate by-products of furfural or hydroxymethylfurfural.

Furfural, also known as 2-furaldehyde, is an aromatic aldehyde which is a derivative obtained by substitute the hydrogen atom at the 2-position of the furan with an aldehyde group. Furfural may be prepared by co-heating rice bran with dilute acid. Pentosan may be hydrolyzed to pentose under the action of acid, and then the pentose is dehydrated and cyclized to generate furfural. The raw materials for producing furfural may be plant materials including polysaccharide hemicellulose such as corn cob. Upon heating and in the presence of a catalyst, hemicellulose may be hydrolyzed to generate sugars such as xylose. Under the similar heating conditions, xylose and other pentosaccharides will dehydrate and lose three water molecules to become furfural.

Hydroxymethyl furfural, also known as 5-hydroxymethyl furfural, includes an aldehyde group and a hydroxymethyl group in the molecule. Energy and chemical products such as medicines, resins, and fuels may be produced through processes such as hydrogenation, oxidation, esterification, condensation, halogenation, and polymerization. Hydroxymethyl furfural may be generated by dehydration of glucose or fructose.

The wall adsorption property may refer to a property that a particle or a colloid is adsorbed to physically adhere to a solid surface. In the present disclosure, the wall adsorption property may refer to the property of a metal catalyst in a mixture (e.g., a catalyst including Cu, etc.) to adhere to the inner surface of a reactor (e.g., a reaction tank). In some embodiments, the wall adsorption property may be reduced by polishing the inner surface of the reactor, adding an inert substance for scraping, or increasing the particle size of certain materials in the reaction system.

Distillation is a method for separating different components of a mixed system including a liquid by using the difference of boiling points of the different components in the mixed system.

Rectification is a distillation process that uses reflux to obtain a separated component with a high purity from a mixed system including a liquid. According to the number of components in the mixed system, the method may be divided into binary rectification and multivariate rectification. In some embodiments of the present disclosure, the alcohol obtained by phrolysis includes a plurality of components with a similar molecular weight and polarity, which may be separated by rectification.

A conversion ratio refers to the proportion of the amount of materials participating in the reaction to the total amount of the materials added into the reaction system. According to the number of reactions, the conversion ratio may be further divided into a one-stage conversion ratio and a multi-stage conversion ratio. The one-stage conversion ratio refers to the ratio of the amount of materials participating in the reaction to the total amount of the materials added to the reactor after the materials are added into the reactor at one time. The multi-stage conversion ratio refers to the ratio of the amount of materials participating in the reaction to the total amount of materials added to the reactor when the unreacted part of the materials is added into the reactor for many times. In some embodiments of the present disclosure, since the reaction of the straw is a reaction in which the polymer is degraded into monomers, the conversion ratio may be referred to as a degradation ratio. In some embodiments of the present disclosure, the one-stage conversion ratio of straw refers to the ratio of the amount of straw materials (the difference between the mass of the straw before the reaction and the mass of the straw after the reaction) participating in the reaction to the amount of initial straw added into the degradation reactor. In the present disclosure, the multi-stage conversion ratio of straw refers to the ratio of the amount of the straw materials participating in the reaction to the amount of the initial straw after the unreacted part of the initial straw is added into the degradation reactor for many times (e.g., 2 or 3 times).

The mesh number may refer to the mesh size of a sieve or the particle size or thickness of the materials passing through the mesh. For example, the mesh number may be defined as the number of meshes that are present on a sieve of 1 square inch. If there are 200 meshes on a sieve of 1 square inch, the sieve has a mesh number of 200 meshes. If the particle size of the materials is equal to the size of the mesh of a 200-mesh sieve, the mesh number of the materials is 200 meshes. If the materials pass through a 120-mesh sieve but do not pass through a 200-mesh sieve, the mesh number of the materials is in the range of 120 to 200 meshes. The sieve standard in the present disclosure is China National Standard Sieve.

Here, terms such as "calcination" and "baking" may be used interchangeably.

Although descriptions similar to "solid phase" or "solid" is used to describe materials including "residues," "catalyst," "raw materials," and "biological object," these descriptions are merely for convenience of description, indicating that the above materials have a certain shape, and are not intended to limit the materials to include no gas or liquid components. Solid or solid materials may also include a certain amount of water.

According to some embodiments of the present disclosure, FIG. 1 is a shematic diagram illustrating an exemplary biological object processing system. The biological object processing system 100 may be applied to perform a series of processing operations such as pretreatment, degradation, separation, or the like of the biological object MI. The biological object processing system 100 may include a pretreatment module P1, a degradation module P2, a solid separation module P3, a lignin extraction module P4, a sugar concentrating module P5, a cracking module P6, and a fractionation module P7.

The pretreatment module P1 may include a pulverizer 104, a cyclone separator 108, a stirring tank 112, and a separation tank 116. The pulverizer 104 may pulverize the biological object M1 to obtain biological object particles M2. The biological object particles M2 may be fed into the stirring tank 112. The dust and air generated when the biological object M1 is pulverized may be sent to the cyclone separator 108, and the air separated with the dust may be discharged. In the stirring tank 112, the biological object particles M2 may be rotationally mixed together with a catalyst M3 and water M4 to obtain a mixture M5 of the biological object particles, the water and the catalyst. After mixing, the mixture M5 may be sent to the separation tank 116 for filtration treatment to obtain a wet mixture M6 of biological object particles and the catalyst. Filtrate M4 may be water including a small amount of inorganic salts and soluble sugars. The filtrate M4 may be further pumped into the stirring tank 112 and mixed with the biological object particles M2 and the catalyst M3 for repeated use. After filtration, the wet mixture M6 of the biological object particles and the catalyst may be sent out of the separation tank 116 and be sent into the degradation module P2.

The degradation module P2 may include a degradation reactor 120. In some embodiments, the degradation module P2 may also include two or more degradation reactors 120. In the degradation reactor 120, the wet mixture M6 of the biological object particles and the catalyst may be heated in a hydrogen atmosphere including hydrogen M7. The polysaccharide included in the biological object particles may undergo a degradation reaction. The polysaccharide included in the biological object particles may include, for example, one or more of a plurality of polysaccharides, hemicellulose, cellulose, or the like. The product of the degradation reaction may include, for example, one or more kinds of monosaccharides such as xylose, arabinose, glucose, or the like. Together with the inorganic salts included in the biological object particles, the monosaccharides and partially degraded polysaccharide produced after the degradation are dissolved in the aqueous solution after the reaction. Other organic and inorganic substances included in the biological object particles, including lignin, organic polymers that are difficult to degrade, and silica, may be present in a form of solid because they cannot be degraded into soluble components. Similarly, the catalyst M3 may also be present in the solid phase due to its insolubility in water. The reaction mixture may be a solid-liquid mixture M8.

After passing through the degradtion reactor 120, the solid-liquid mixture M8 may be separated and sent to the solid separation module P3. The solid separation module P3 may include a first chamber 129 that is a washing filter and a second chamber 130 that is a washing filter. The solid-liquid mixture M8 may be separated in the first chamber 129 to obtain a mixture M9 including the catalyst and lignin, and a solution M11 including sugars and inorganic salts. The mixture M9 including the catalyst and lignin may be washed and/or filtered in the second chamber 130 washing filter to obtain a solution M12 including sugars and inorganic salts.

The mixture M9 including the catalyst and lignin separated by the solid separation module P3 may be fed into the lignin extraction module P4. The lignin extraction module P4 may include a separator 123 and a lignin extraction device 128. The separator 123 separates the mixture M9 to obtain a lignin crude product M10. The lignin extraction device may further purify the lignin.

The solution M12 including sugars and inorganic salts may be transferred from the solid separation module P3 to the sugar concentrating module P5. The sugar concentrating module P5 may include a sugar solution storage tank 134. The solution may be concentrated and stored in the sugar solution storage tank 134 to obtain a sugar solution M13 (which also includes a certain amount of inorganic salts) with a higher concentration and water steam (not shown). The water steam may be collected by condensation for cyclic utilization. The sugar solution M13 with the higher concentration may be used as raw materials in the subsequent hydrogenation reaction.

It should be understood that, in some embodiments, the solution M12 may also be processed directly into the cracking module P6 without concentration.

The sugar solution M13 with the higher concentration may be fed into the cracking module P6 after leaving the sugar concentrating module P5. The cracking module P6 may include two sections, one being a hydrogenation reactor 136 and the other being a cracking reactor 140. In the hydrogen atmosphere of the hydrogenation reactor 136, the sugar solution with the higher concentration may be hydrogenated, and a sugar alcohol solution M14 with a higher concentration may be obtained. In some embodiments, the mass percentage concentration of the sugar alcohol solution with the higher concentration may be 10% to 50%. The sugar alcohol solution M14 may undergo a cracking reaction in the cracking reactor 140 at a higher temperature and a hydrogen atmosphere to generate a glycol solution M15. During the cracking reaction, the C—C bonds in the sugar alcohol may be broken to generate two or more alcohols. One sugar alcohol molecule may generate two or more alcohols having a smaller molecular weight, for example, ethylene glycol, 1,2-propylene glycol, 1,3-propanediol, or the like. These small-molecule alcohols may be present in the glycol solution M15 in the form of a solute.

After the hydrogenation reaction and the cracking reaction, the cracking product (the glycol solution M15) may be fed into the fractionation module P7. The fractionation module P7 may include a rectification column 144 and an evaporator 148. In the rectification column 144, the glycol solution M15 may be heated and vaporized. After the steam is condensed, different compounds may be collected in different temperature ranges. In some embodiments, water and other components with a low boiling point may be collected in the form of fraction M16. 1,2-propanediol may be collected in the form of fraction M17. Ethylene glycol may be collected in the form of fraction M18. 1,3-propanediol may be collected in the form of fraction M19. The remaining inorganic salts that are difficult to gasify and a small amount of water may remain in a solid phase M20. Then, the solid phase M20 may be fed into the evaporator 148 for drying, and the water in the solid phase M2 may be evaporated to obtain an inorganic salt M21.

According to some embodiments of the present disclosure, FIG. 2 is a shematic diagram illustrating an exemplary biological object preprocessing device. In some embodiments, the biological object preprocessing device may include one or more pulverizers 104, one or more cyclone separators 108, one or more bag filters 109, and one or more fans 110.

In some embodiments, the pulverizer 104 may pulverize biological objects having a large size to meet the size requirements of the biological object particles. The pulverizer 104 may include one or more feed ports 104-1, one or more discharge ports 104-2, a cutting mechanism 104-3, and one or more air outlets 104-4. The cutting mechanism 104-3 may include one or more cutters. Depending on the different requirements of the size of biological object particles, the pulverizer 104 may pulverize the biological object to obtain biological object particles with different mesh numbers. The size of the biological object particles may be a specific mesh number, for example, 10 meshes, 20 meshes, 60 meshes, 80 meshes, 100 meshes, 120 meshes, 200 meshes, 300 meshes, etc. The size of the biological object particles may also be a certain range of meshes, for example, 10 meshes to 20 meshes, 20 meshes to 60 meshes, 60 meshes to 80 meshes, 80 meshes to 100 meshes, 100 meshes to 120 meshes, 120 meshes to 200 meshes, and 200 meshes to 300 meshes. In some embodiments, the pulverizer 104 may be one or more of a crusher (e.g. below 60 meshes), a pulverizer (e.g. 60 meshes to 120 meshes), a superfine pulverizer (e.g. 120 meshes to 300 meshes), and an ultrafine pulverizer (e.g. over 300 meshes).

In some embodiments, the cyclone separator 108 may perform a gas-solid separation of the air including dust to separate the high-density dust from the low-density air for subsequent filtration and other operations. The cyclone separator 108 may include one or more air inlets 108-1, a separation chamber 108-2, and one or more air outlets 108-3. The air inlet 108-1 of the cyclone separator 108 may be connected to the air outlet 104-4 of the pulverizer 104 to receive the air including dust discharged from the pulverizer 104.

In some embodiments, the bag filter 109 may filter the air including dust generated by the biological object pulverization to remove the dust particles in the air. The bag filter 109 may include one or more air inlets 109-1, a filter chamber 109-2, one or more filter bags 109-3, and one or more air outlets 109-4. The air inlet 109-1 of the bag filter 109 may be connected to the air outlet 108-3 of the cyclone separator 108 to receive the air including dust from the cyclone separator 108.

The fan 110 may be configured to discharge the filtered air from the bag filter 109. In some embodiments, the fan 110 may receive power from a circuit. The blades of the fan rotate under an electric drive, causing the air to flow. The fan 110 includes one or more air inlets 110-1, a casing 110-2, and one or more air outlets 110-3. The air inlet 110-1 of the fan 110 may be connected to the air outlet 109-4 of the bag filter 109 to receive the filtered air from the bag filter 109. The air may be introduced into the casing 110-2 from the air inlet 110-1, and after the air is driven by the fan blades, an air flow forms and may leave the fan 110 from the air outlet 110-3. According to the materials of the fan, the fan 110 may be an iron-shell fan, a fiberglass fan, a plastic fan, an aluminum fan, a stainless steel fan, or the like. According to the direction of the air flow, the fan 110 may be a centrifugal fan, an axial fan, a diagonal flow (mixed flow) fan, a cross flow fan, or the like. According to the pressure, the fan 110 may be a negative-pressure fan, a low-pressure fan, a medium-pressure fan, a high-pressure fan, or the like. According to the form of pressure, the fan 110 may be a single-stage-pressure fan, a two-stage-pressure fan, a multi-stage-pressure fan, or the like.

In some embodiments, the biological object may be fed into the cutting mechanism 104-3 through the feed port 104-4, and be pulverized. The pulverized biological object may be sent out from the discharge port 104-2. After the biological object is pulverized, the air including dust may be discharged from the air outlet 104-4, and then sent to the separation chamber from the air inlet 108-1 for preliminary dust removal. The air after the preliminary dust removal may be discharged from the air outlet 108-3, and then introduced into the filter chamber 109-2 from the air inlet 109-1. The filtration chamber 109-2 may further dedust the air after the preliminary dust removal. The filter chamber 109-2 may include a filter bag 109-3 for the further dust removal. The dust-removed air may be discharged from the air outlet 109-4, and then introduced into the casing 110-2 of the fan through the air inlet 110-1, and is driven by the blades inside the casing, and is discharged from the air outlet 110-3.

The above description of the biological object preprocessing device is merely a specific example and should not be considered as the only feasible implementation. Obviously, for those skilled in the art, after understanding the basic principles of biological object preprocessing, it is possible to make various modifications and changes to the specific implementation and steps of the biological object preprocessing device without departing from this principle. However, these modifications and changes are still within the scope of the above description. For example, in some embodiments, some devices may be added or subtracted from the biological object preprocessing device. For example, in the biological object preprocessing device, the bag filter 109 may not be included. For example, in the biological object preprocessing device, a sieving device may be added to sieve the biological object particles of different sizes. The sieving device may include, but is not limited to, a mesh, a staged impeller, an air separation device, or the like, or any combination thereof. The sieving device and the pulverizer may exist independently of each other or as a whole. In some embodiments, the various devices in the biological object preprocessing device may be replaced by other devices. For example, the cyclone separator 108 may be replaced by a washing dust-removing device, a filter dust-removing device, an electrostatic dust-removing device, a magnetic dust-removing device, and a mechanical force dust-removing device. In some embodiments, the various devices in the biological object preprocessing device may exist independently, or as a whole. Such variants are covered by the present disclosure.

According to some embodiments of the present disclosure, FIG. 3 is a flowchart illustrating an exemplary process for preprocessing a biological object. In 310, the biological object may be pulverized to obtain a mixture of air including dust and biological object particles. The pulverization of the biological object may be performed by the pulverizer 104. In some embodiments, the particle size of the pulverized biological object may be related to the specific parameters of the pulverizer and the pulverizing time. In some embodiments, for different biological objects, biological object particles of different sizes may be obtained by controlling the pulverizing time. In some embodiments, the rice straw is used as the raw materials, and the parameters of the pulverizer are as follows: the rated voltage of 220V, the load power of 1100 W, the motor speed of 29000 rpm, the pulverization degree of 60 meshes to 300 meshes, the rated frequency of 50 Hz. When the pulverizing time is from 0 minute to 1.5 minutes, biological object particles with 10 meshes to 100 meshes may be obtained; when the pulverizing time is from 1.5 minutes to 5 minutes, biological object particles with 100 meshes to 300 meshes, or biological object particles with a mesh number greater than 300 meshes may be obtained. In 320, the biological object particles may be fed into a stirring tank 112. In 330, air including dust passed through the cyclone separator 108 to trap at least a portion of the dust. In some embodiments, operations 320 and 330 may be performed simultaneously or not simultaneously. In 340, the remaining air including dust may passed through the bag filter 109 to obtain the filtered air. At least a portion of dust may be trapped in the bag filter 109.

The above description of the process of biological object preprocessing is merely a concrete example and should not be considered as the only feasible implementation. Obviously, for those skilled in the art, after understanding the basic principles of biological object preprocessing, it is possible to make various modifications and changes to the specific implementation and steps of the biological object preprocessing device without departing from this principle. However, these modifications and changes are still within the scope of the above description. For example, in some embodiments, one or more operations may be added or subtracted. For example, a sieving operation using a sieve, a staged impeller, a wind selection device, or the like, or any combination thereof, may be added after operation 310. In some embodiments, the same operation may be repeated in order to achieve the effect and purpose of the process, and a plurality of operations may be performed cyclically. For example, in order to make the particle size of the pulverized biological object meets the requirements, operation 310 may be repeated. If a sieving operation is added, operation 310 may be carried out first to pulverize the biological object, and then the sieving operation may be carried out to sieve the pulverized biological object, and then, in 310, the pulverized biological object is further pulverized, and circulating repeatedly to obtain biological object particles meeting the particle size requirements. For example, in order to make the dust removal more thorough, operation 320 may be repeated, or operation 330 may be repeated. Such variants are covered by the present disclosure.

Figure 4:
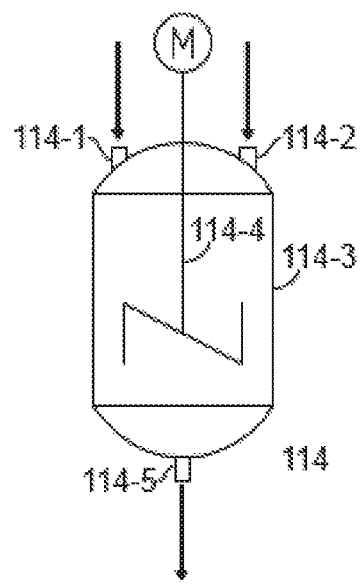
FIG. 4 is a shematic diagram illustrating an exemplary catalyst preparation tank according to some embodiments of the present disclosure.

According to some embodiments of the present disclosure, FIG. 4 is a shematic diagram illustrating an exemplary catalyst preparation tank. In some embodiments, the catalyst preparation tank 114 may be configured to uniformly mix solid substances (e.g., solid catalysts, etc.) with liquid substances (e.g., water, etc.), or store solid-liquid mixtures (e.g., mixtures of solid catalysts and water, etc.).

In some embodiments, the catalyst preparation tank 114 may include one or more solid feed ports 114-1, one or more liquid feed ports 114-2, a chamber 114-3, one or more stirring devices 114-4, and one or more discharge ports 114-5.

In some embodiments, the solid feed port 114-1 and the liquid feed port 114-2 may be located at or near the top of the chamber 114-3, and the discharge port 114-5 may be located at or near the bottom of the chamber 114-3. The solid feed port 114-1, the liquid feed port 114-2 or the discharge port 114-5 may include one or more sealing devices. The sealing device may be configured to seal the solid feed port 114-1, the liquid feed port 114-2, or the discharge port 114-5, thereby making the catalyst preparation tank 114 become a sealed container, and/or controlling the entry and discharge of the substances. In some embodiments, the sealing device may be a valve, a sealing cover, a piston, a hydraulic seal, a pneumatic seal, or the like, or any combination thereof.

In some embodiments, the stirring device 114-4 may be configured to mix solid substances and liquid substances. The stirring device 114-4 may be a magnetic stirring device, a mechanical stirring device, an ultrasonic stirring device, or the like, or any combination thereof. In some embodiments, the magnetic stirring device may include a magnetic stirrer, a stirring bar, or the like. In some embodiments, the mechanical stirring device may include a motor or a stirring rod, or the like. The shape of the stirring rod may be paddle, toothed, turbine, anchor, frame, ribbon, screw or Brumakin, etc.

In some embodiments, a solid substance (e.g., solid catalyst, etc.) may be fed into the chamber 114-3 from the solid feed port 114-1, and a liquid substance (e.g., water) may be fed into the chamber 114-3 from the liquid feed port 114-2. The solid substance (e.g., solid catalyst, etc.) and the liquid substance (e.g., water, etc.) may be uniformly mixed by the stirring device 114-4. The mixed solid-liquid mixture e.g., a mixture of the solid catalyst and water) may be discharged from the discharge port 114-5 for further processing (e.g., mixing with biological object in a stirring tank), or be stored in the catalyst preparation tank 114 for use.

Figure 5:
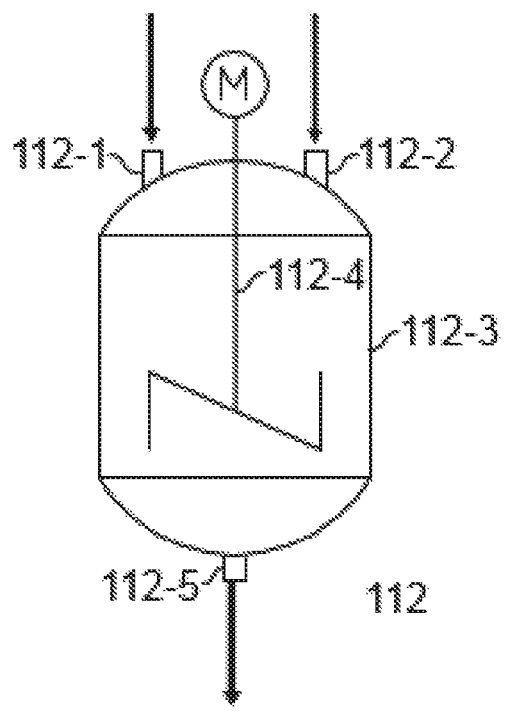
FIG. 5 is a shematic diagram illustrating an exemplary stirring tank according to some embodiments of the present disclosure.

According to some embodiments of the present disclosure, FIG. 5 is a shematic diagram illustrating an exemplary stirring tank. In some embodiments, the stirring tank 112 may be configured to mix solid substances (e.g., the biological object, the biological object particles, etc.) and liquid substances (e.g., mixtures of solid catalysts and water), or store solid-liquid mixtures (e.g., mixtures of biological object particles, solid catalysts, and water).

In some embodiments, the stirring tank 112 may include one or more solid feed ports 112-1, one or more feed ports for liquids including solids 112-2, a chamber 112-3, one or more stirring devices 112-4 (see FIG. 4 for details), and one or more discharge ports 112-5.

In some embodiments, the solid feed port 112-1 and the feed port for liquids including solids 112-2 may be located at or near the top of the chamber 112-3, and the discharge port 112-5 may be located at or near the bottom of the chamber 112-3. The solid feed port 112-1, the feed port for liquids including solids 112-2, and the discharge port 112-5 may include one or more sealing devices. The sealing device may be configured to seal the solid feed port 112-1, the feed port for liquids including solids 112-2, and the discharge port 112-5, thereby making the stirring tank 112 become a sealed container, and/or controlling the entry and discharge of solid substances, liquids including solids, or solid-liquid mixtures. In some embodiments, the sealing device may include a sealing cover, a piston, a hydraulic seal, a pneumatic seal, or the like, or any combination thereof.

In some embodiments, the solid substances (e.g., the biological object, the biological object particles, etc.) may be fed into the chamber 112-3 from the solid feed port 112-1, and the liquids including solids (e.g., a mixture of the solid catalyst and water, etc.) may be fed into the chamber 112-3 from the feed port for liquids including solids 112-2. The solid substances (e.g., the biological object, the biological object particles, etc.) and the liquids including solids (e.g., a mixture of the solid catalyst and water) may be uniformly mixed by the stirring device 112-4. The mixed solid-liquid mixture (e.g., the mixture of the biological object, the biological object particles, the solid catalyst, and water, etc.) may be discharged through the discharge port 112-5 for further processing (e.g., to the feeding tank for further mixing), or be stored in the stirring tank 112 for use.

According to some embodiments of the present disclosure, FIG. 6 is a shematic diagram illustrating an exemplary feeding tank. In some embodiments, the feeding tank 115 may be configured to further mix a solid mixture (e.g., a mixture of the biological object and the catalyst) or a solid-liquid mixture (e.g., a mixture of the biological object, the catalyst, and water), store solid-liquid mixtures (e.g., a mixture of the biological object, the catalysts, and water, etc.), or act as a intermediate device for bufferring.

In some embodiments, the feeding tank 115 may include one or more feed ports 115-1, a chamber 115-2, one or more stirring devices 115-3 (see FIG. 4 for details), and one or more discharge ports 115-4.

In some embodiments, the feed port 115-1 may be located at or near the top of the chamber 115-2, and the discharge port 115-4 may be located at or near the bottom of the chamber 115-2. The feed port 115-1 and the discharge port 115-4 may include one or more sealing devices. The sealing device may be configured to seal the feed port 115-1 and the discharge port 115-4, thereby making the feeding tank 115 become a sealed container, and/or controlling the entry and discharge of the solid-liquid mixture. In some embodiments, the sealing device may be a valve, a sealing cover, a piston, a hydraulic seal, a pneumatic seal, or the like.

In some embodiments, a solid mixture (e.g., a mixture of the biological object and the catalyst) or a solid-liquid mixture (e.g., a mixture of the biological object, the catalyst, and water) may be fed into the chamber 115-2 from feed port 115-1 and be uniformly mixed under the action of the stirring device 115-3. The mixed solid-liquid mixture (e.g., a mixture of the biological object, the catalyst, and water) may be discharged from the discharge port 115-4 for further processing (e.g., to a biological object separation tank for water removal treatment, etc.), or be stored in the feeding tank 115 for use.

The above description of the feeding tank structure is merely a specific example and should not be considered as the only feasible embodiment. Obviously, for professionals in the field, after understanding the basic principles of the feeding tank, various modifications and changes in the form and details of the structure and implementation of the feeding tank may be made without departing from this principle. However, these modifications and changes are still within the scope of the above description. For example, in some embodiments, the feeding tank 115 may not include a stirring device, and the feeding tank 115 is only used as a storage device or an intermediate buffer device for storing a solid-liquid mixture or for buffering. As another example, after being discharged out by the stirring tank 112, a mixture of the biological object, the catalyst, and water may be directly introduced into the subsequent devices, such as the biological object feeding tank 116 with solid-liquid separation or the degradation reactor 121, without passing through the feeding tank 115. Such variants are covered by the present disclosure.

As another example, in some embodiments, the mixing mode of the catalyst, water, and the biological object may be changed. For example, water and straw may be mixed first, and then the mixture of the water and the straw may be mixed with the catalyst. For example, the straw and the catalyst may be mixed first, and then the mixture of the straw and the catalyst may be mixed with water. For example, the straw, the water, and the catalyst may be mixed at the same time. For example, the straw may be mixed with the catalyst without adding water. Such variants are covered by the present disclosure.

According to some embodiments of the present disclosure, FIG. 7-A is a shematic diagram illustrating an exemplary biological object feeding tank with solid-liquid separation. In some embodiments, the separation tank 116 may be used for a preliminary solid-liquid separation, such as, separating a portion of water from a mixture of the biological object, the solid catalyst and water to control the mass ratio of the biological object to water.

In some embodiments, the separation tank 116 may include one or more feed ports 116-1, a chamber 116-2, a discharge device 116-3, one or more filter devices 116-4, one or more discharge ports 116-5, and one or more water outlets 116-6.

In some embodiments, the feed port 116-1 may be located at or near the top of the chamber 116-2. The discharge port 116-5 may be located on the side wall of the chamber 116-2, and the water outlet 116-6 may be located at or near the bottom of the chamber 116-2. The feed port 116-1, the discharge port 116-5, and the water outlet 116-6 may include one or more sealing devices. The sealing device may be configured to seal the feed port 116-1, the discharge port 116-5, or the water outlet 116-6, thereby making the separation tank 116 become a sealed container, and/or controlling the entry and discharge of solid-liquid mixtures and liquids. In some embodiments, the sealing device may be a sealing cover, a piston, a hydraulic seal and a pneumatic seal, or the like, or any combination thereof.

In some embodiments, the discharge device 116-3 may be configured to deliver the solid-liquid mixture out of the chamber 116-2. The discharge device 116-3 may be connected to the discharge port 116-5. In some embodiments, the discharge device 116-3 may be a feeding screw.

In some embodiments, the filter device 116-4 may be configured to initially filter the mixture of the catalysts, the biological object particles, and water to control the mass ratio of water to the biological object particles. The concentration of the sugar solution generated after degradation may be adjusted by controlling the mass ratio of water to the biological object particles. The filter device 116-4 may be located downstream of the fluid flow of the discharge device 116-3 and/or the discharge port 116-5. The filter device 116-4 may be a strainer, a mesh screen, a filter paper, a filter cloth, a filter cotton, or the like, or any combination thereof. The filtering device may include a certain number of pores. The pore size allows for the passage of water or a solution and prevents the passage of solid particles larger than the pore size. In some embodiments, filter devices with different pore sizes may be selected according to the size of the catalyst and/or the biological object. In some embodiments, the mixture may also not pass through the filter device 116-4.

In some embodiments, a solid-liquid mixture (e.g., a mixture of the biological object, the catalyst, and water) may be fed into the chamber 116-2 from the feed port 116-1. The liquid substance in the solid-liquid mixture (e.g., an aqueous solution of soluble components in water or the biological object) may be filtered by the filter device 116-4 to the bottom of the chamber 116-2 by the gravity, and be discharged by the water outlet 116-6 for further processing (e.g., into a storage tank or a recycling device for subsequent use of devices requiring water). The solid substance and a small portion of the liquid substance in the solid-liquid mixture (e.g., a wet mixture of the biological object particles and catalyst, etc.) may be intercepted by the filter device 116-4, and discharged from the discharge device 116-3 via the discharge port 116-5 to the chamber 116-2 for further processing (e.g., to the degradation reactor 121 for degradation reaction, etc.), or be stored in the chamber 116-2 for use.

The above description of the biological object separation tank structure is merely a specific example and should not be considered as the only feasible embodiment. Obviously, for those skilled in the art, after understanding the basic principles of the biological object separation tank, various modifications and changes in the form and details of the structure and implementation of the biological object separation tank may be carried out without departing from this principle. However, these modifications and changes are still within the scope of the above description. For example, in some embodiments, the separation tank 116 may further include a gas pressure adjusting device. The gas pressure adjusting device may be used to change the gas pressure within the chamber 116-2 to utilize the atmospheric pressure to increase or decrease the rate of solid-liquid separation. As another example, in some embodiments, a mixture of the biological object and the catalyst or a mixture of the biological object, the catalyst, and water may be fed into the degradation reactor 121 without undergoing a water filtration operation of the separation tank 116. Such variants are covered by the present disclosure.

According to some embodiments of the present disclosure, FIG. 7-B is a shematic diagram illustrating an exemplary dispensing device. In some embodiments, the dispensing device 118 may be configured to feed or discharge materials. The materials may be solid materials (e.g., the biological object, the solid catalyst, etc.), or solid-liquid mixing materials (e.g., a mixture of the biological object, the solid catalysts, and water), reaction residues, a mixture of the solid catalysts and water, a mixture of lignin and water, a mixture of the solid catalysts, fine straw slag, and water, etc.).

In some embodiments, the dispensing device 118 may include one or more feed ports 118-1, a barrel 118-2, one or more discharge ports 118-6 and/or 118-7, and a screw rod 118-8. In some embodiments, the barrel 118-2 may be placed horizontally or be inclined at an angle to the horizontal plane.

The feed port 118-1 may be configured to input the materials. The discharge ports 118-6 and/or 118-7 may be configured to discharge the materials. In some embodiments, the feed port 118-1 may be at an axial end of the barrel 118-2, and discharge port 118-6 and/or 118-7 may be at the other axial end of the the barrel 118-2; the feed port 118-1 may be in the middle of the barrel 118-2, and discharge ports 118-6 and/or 118-7 may be at ane axial end of the barrel 118-2; the feed port 118-1 may be in the middle of the barrel 118-2, and discharge ports 118-6 and/or 118-7 may be at two axial ends of the barrel 118-2; the two feed ports 118-1 may be respectively at two axial ends of the barrel 118-2, and discharge ports 118-6 and/or 118-7 may be in the middle of the barrel 118-2; or the feed port 118-1 may be at the end or in the middle of the barrel 118-2, and discharge ports 118-6 and/or 118-7 may be in the axial direction of the barrel 118-2. The axial direction described here refers to the direction parallel to the screw rod 118-8.

In some embodiments, the dispensing device 118 may include one or more sealing devices. The sealing device may be configured to seal the feed port 118-1, the discharge ports 118-6 and/or 118-7, thereby making the barrel 118-2 become a sealed container, and/or controlling the entry and discharge of the materials. In some embodiments, the sealing device may be a valve, a sealing cover, a piston, a hydraulic seal, a pneumatic seal, or the like, or any combination thereof.

In some embodiments, the dispensing device 118 may be used in combination with a reactor for feeding and discharging materials. When the dispensing device 118 is used for feeding materials, the feed port 118-1 may be connected to the feed port of the reactor, and the discharge ports 118-6 and/or 118-7 may be located inside the reactor chamber. In some embodiments, the feed port 118-1 may be opened and the discharge ports 118-6 and 118-7 may be closed to allow materials to be introduced into the barrel 118-2. When the amount of materials in the barrel 118-2 reaches a certain value, the feed port 118-1 may be closed and the discharge ports 118-6 and 118-7 may be opened so that the materials move under the action of the screw rod 118-8 to the discharge ports 118-6 and/or 118-7, then to be introduced into the reactor chamber. During the entire feeding process, the reactor chamber may maintain the airtightness, and the reaction conditions such as temperature and pressure inside the reactor chamber are kept constant, and the reaction in the reactor chamber may be normally performed. In some embodiments, the reactor may be a biological object degradation reactor.

In some embodiments, the barrel 118-2 may be used to trap materials fed from the feed port 118-1. Due to the gravity of the materials and the friction with the barrel wall of the barrel 118-2, the materials may move along the bottom of the barrel 118-2 under the action of the screw rod 118-8 without rotating with the screw rod. In some embodiments, the shape of the barrel 118-2 may be tubular or U-shaped. In some embodiments, the barrel 118-2 may be modified according to different application scenarios. For example, when the dispensing device 118 is applied to the biological object separation tank in FIG. 7-A, in order to achieve the purpose of water filtration, holes may be added at appropriate positions of the barrel wall of the barrel 118-2, or the appropriate position of the barrel wall of the barrel 118-2 may be directly replaced with a filter device (e.g., a filter).

In some embodiments, the screw rod 118-8 may be configured to propel the materials along the bottom of the barrel 118-2. In some embodiments, the screw rod 118-8 may be located inside the barrel 118-2. In some embodiments, the screw rod 118-8 may include a drive device such as a screw shaft, a thread, and a screw rod. The shape of the thread may be a solid thread, a belt thread, a blade thread, a toothed thread, or the like, or any combination thereof. In some embodiments, for the same screw rod 118-8, the thread pitch, the thread shape or the thread direction may be the same or different. In some embodiments, if the dispensing device 118 includes two or more screw rods 118-8, the thread pitch, thread shape or thread direction of the two or more screw rods 118-8 may be the same or different. In some embodiments, the screw drive device may act on the screw shaft to rotate the screw shaft in the axial direction. The screw drive device may be located at one end of the screw shaft. The screw drive device may include, but is not limited to, a motor. The screw drive device may also include but is not limited to a manual device.

In some embodiments, the materials (e.g., a mixture of the biological object, the catalyst, and water) may be fed into the barrel 118-2 from the feed port 118-1, and the materials (e.g., a mixture of the biological object, the catalyst, and water) is moved along the bottom of the barrel 118-2 by the screw rod 118-8, and may be discharged from the discharge port 118-6 and/or 118-7.

In some embodiments, the dispensing device 118 may further include a heating device. The heating device may be used for drying, heating, and heat preservation of materials. The heating device may include a heating jacket 118-3, a heating substance inlet 118-4, and a heating substance outlet 118-5. The heating substance inlet 118-4 may be used to feed a heating substance, wherein the heating substance may be hot air, steam, hot water, or hot oil, or the like. The heating substance outlet 118-5 may be used to discharge the cooled heating substance. The heating jacket 118-3 may be configured to provide heat to the materials for the purpose of drying or heating the materials. In some embodiments, the heating jacket 118-3 may be located outside the barrel 118-2.

In some embodiments, the heating substance may be introduced into the heating jacket 118-3 from the heating substance inlet 118-4, and then be cooled, and be discharged from the heating substance outlet 118-5.

The above description of the dispensing device is only a specific example and should not be considered as the only feasible implementation. Obviously, for those skilled in the art, after understanding the basic principles of the ingredients, it is possible to make various modifications and changes in the form and details of the structure and implementation of the ingredients without departing from this principle. However, these modifications and changes are still within the scope of the above description. For example, in some embodiments, the screw rod 118-8 may not include a screw shaft. In some embodiments, the heating substance that is introduced into the heating jacket 118-3 may be replaced by a heating structure placed inside the heating jacket 118-3, for example, a resistance wire, or the like. Such variants are covered by the present disclosure.

According to some embodiments of the present disclosure, FIG. 8-A is a flowchart illustrating an exemplary process for feeding a biological object. Through the biological object feeding process as described below, the mass ratio of the biological object to water in the materials may be controlled to control the concentration of the sugar solution obtained after degradation.

In 810, the catalyst is mixed with water in a catalyst preparation tank 114, and a wet catalyst may be obtained. In 820, the wet catalyst is mixed with the biological object in the stirring tank 112, and an initial mixture may be obtained. In some embodiments, the mass ratio of the biological object to water in the initial mixture may be 1:1 to 1:11, 1:2 to 1:10, 1:3 to 1:9, 1:4 to 1:8, 1:5 to 1:7, 1:6, 1:10 to 5:10, 2:10 to 4:10, or 3:10, etc.

In 830, the initial mixture may be filtered in the biological object separation tank 116 to obtain a filtrate and a wet mixture of the biological object and the catalyst. In some embodiments, in the filtered mixture of the biological object, the catalyst, and water, the mass ratio of the biological object to water may be 1:1 to 1:6, 1:2 to 1:5, or 1:3 to 1:4, etc.

For example, 9 to 15 kg of a catalyst and 300 kg to 500 kg of water may be added to the catalyst tank 114 with a capacity of 2000 liters to obtain a mixture of the catalyst and water. The mixture of the catalyst and water may be mixed with 30 kg to 50 kg of a biological object (e.g., straw) to obtain the initial mixture, wherein the mass ratio of the biological object, the catalyst, and water in the initial mixture is about 10:3:100. The initial mixture is filtered through the separation tank 116 having a capacity of 800 liters to obtain a filtrate and a wet mixture of the biological object (e.g., wet straw) and the catalyst. For example, in a wet mixture of the biological object (e.g., straw) and the catalyst, the mass of the biological object may be 30 kg to 50 kg, the mass of the catalyst may be 9 kg to 15 kg, the mass of water may be 120 kg to 200 kg, and the mass ratio of the biological object, the catalyst, and water may be about 10:3:40, and the water filtration ratio (the mass of filtered water to the mass of original water) may be about 33% to 76%.

In 840, the wet mixture of the biological object and the catalyst may be sent to the degradation reactor 121 or 122 for degradation reaction, and the filtrate may be stored in the storage tank for use.

The above description of the biological object feeding process is merely exemplary and should not be considered as the only feasible implementation. Obviously, for those skilled in the art, after understanding the basic principles of the biological object feeding process, it is possible to make various modifications and changes to the form and details of the biological object feeding process and implementation without departing from this principle. However, these modifications and changes are still within the scope of the above description. For example, in some embodiments, the mixing order of the biological object, the catalyst, and water may be changed. For example, water and the biological object may be mixed first, and then the mixture of water and the biological object may be mixed with the catalyst. In some embodiments, the biological object and the catalyst may be mixed first, and then the mixture of the biological object and the catalyst may be mixed with water. In some embodiments, the biological object, water, and the catalyst may also be mixed at the same time. In some embodiments, in order to achieve the purpose of further mixing and/or buffering the materials, an operation may be added after operation 820, for example, the initial mixture may be further mixed in the feeding tank 115. In some embodiments, the mixture of the biological object, the catalyst, and water may be fed into the degradation reactor 121 or 122 without the water filtration operation of operation 830. Such variants are covered by the present disclosure.

According to some embodiments of the present disclosure, FIG. 8-B is a flowchart illustrating an exemplary process for mixing new materials and old materials. In the process of biological object degradation, the catalyst component existing in the form of particles or powder may adsorb on the reactor wall (e.g., the degradation reactor chamber 121-3 in FIG. 9) by stirring at a high temperature. The adsorption may result in a decrease in the amount of catalysts actually involved in the reaction during the degradation reaction, which may lead to a reduction in catalytic efficiency and is not conducive to the degradation reaction. In order to reduce the wall adsorption property of the catalyst and improve the catalytic efficiency of the catalyst, the solid residue after the degradation reaction may be mixed with a new biological object for degradation reaction, or the solid residue after the degradation reaction may be mixed with the auxiliary agent (e.g., an inert component that is easily separated from the reaction product) for degradation reaction, and the auxiliary agent herein is described in detail below. The new biological object particles and the auxiliary agent are larger in size than the solid residue and catalyst after the degradation reaction. The large particles of the biological object and the auxiliary agent may cause the catalyst particles adsorbing on the reactor wall to fall off the reactor wall by stirring, thereby improving the catalytic efficiency of the catalyst and the degradation rate of the biological object.

In 821, a solid residue after biological object degradation is provided. The solid residue may include catalysts (including unreacted and/or reacted catalysts) and undegraded biological object particles. The undegraded biological object particles may include cellulose and/or lignin.

In some embodiments, the solid residue may be discharged directly from the degradation reactor. In some embodiments, the solid residue may be a solid obtained by performing one or more separation operations including filtration, washing or drying to a solid residue discharged from the degradation reactor. In some embodiments, the above separation operation may remove lignin, sugars, inorganic salts or water from the solid residue.

Figure 17:
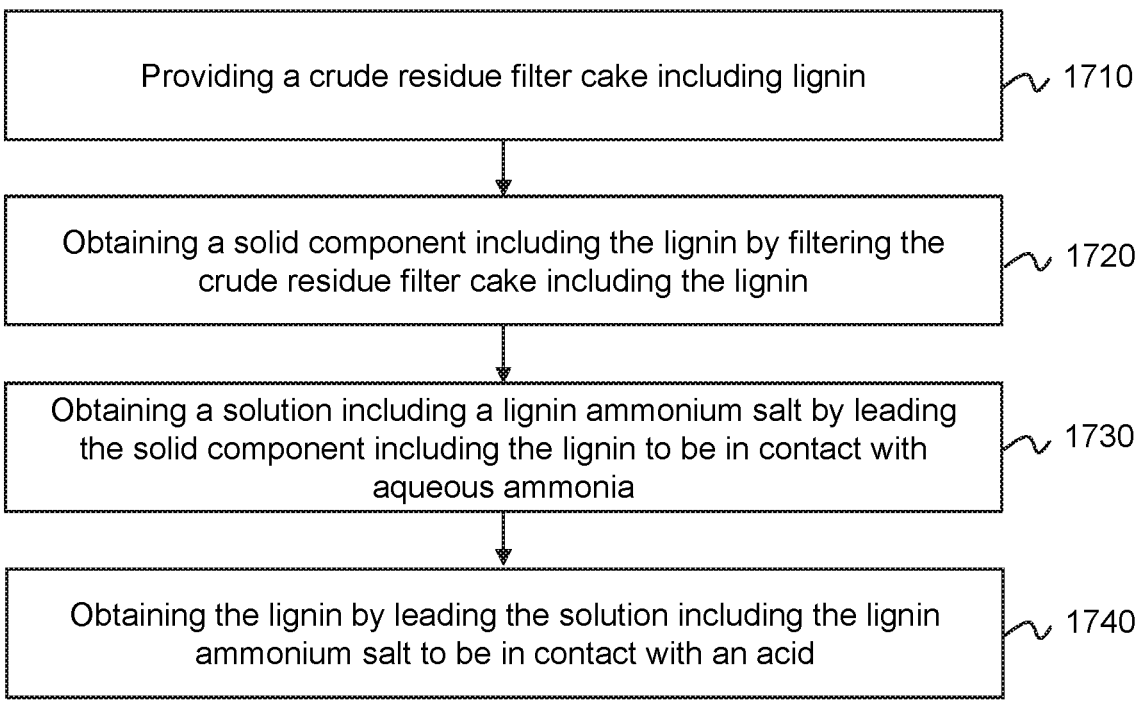
FIG. 17 is a flowchart illustrating an exemplary process for extracting lignin according to some embodiments of the present disclosure.

In 822, the solid residue is mixed with a new biological object to obtain a mixture. In some embodiments, the feeding process of the solid residue and the new biological object may be as follow: after the reaction has been carried out for a period of time (e.g., 2 hours, etc.), a mixture of the new biological object, the catalyst, and water (the mixing process of the new biological object, the catalyst, and water is detailed in FIG. 8-A) after filtration of water may be added to the degradation reactor (e.g., a primary degradation reactor 121 or a secondary degradation reactor 122) to mix with the solid residue. In some embodiments, after the reaction has been carried out for a period of time (e.g., 2 hours, etc.), lignin in the solid residue after the reaction may be extracted (the extraction process is detailed as shown in FIG. 17), and the remaining solid residue is mixed with a new biological object, the catalyst, and water, followed by a degradation reaction. In some embodiments, the solid residue after the extraction of lignin may be mixed with a new biological object, the catalyst, and water, and then be processed by water filtration treatment. In some embodiments, the new biological object, the catalyst, and water may be processed by water filtration treatment followed by mixing with the solid residue after the extraction of the lignin. The mixing of the solid residue with the new biological object may be carried out in a degradation reactor or in another device, for example, the stirring tank 112.

In some embodiments, the mass ratio of new materials to old materials may be in a range of 1:4 to 4:1.

In some embodiments, the mixture of the new biological object and the degraded solid residues may be further degraded by hydrogenating.

In some embodiments, a metallic copper-based catalytic component may be used. The component may include a component including copper and an auxiliary agent. The mass ratio of the component including copper to the auxiliary agent may be in a range from 1:0 to 1:20, 1:1 to 1:15, 1:5 to 1:10, 1:1 to 1:9, 7:13 to 3:17, or 3:7 to 1:4. The mass percentage of the component including copper may be in a range from 4.8% to 100%, 6.2% to 50%, 9.1% to 16.7%, 10% to 50%, 15% to 35%, or 20% to 30%. The mass percentage of the auxiliary agent may be in a range from 0% to 95.2%, 50% to 93.8%, 83.3% to 90.9%, 50% to 90%, 65% to 85%, or 70% to 80%. The mass of copper element in the component including copper may be in a range from 10% to 100%, 30% to 100%, 50% to 100%, or 80% to 100%.

The component including copper may be a component including a copper element, for example, metallic copper, oxide of copper, a copper salt, or the like, or any combination thereof. In some embodiments, the oxide of copper may be at least one of copper oxide and cuprous oxide. In some embodiments, the copper salt may be a basic copper carbonate, a copper chloride, a cuprous chloride, a copper sulfate, a copper nitrate, a copper oxalate, or the like, or any combination thereof. The component including copper such as copper oxide, cuprous oxide, and basic copper carbonate may be reduced in a hydrogen atmosphere and a high-pressure environment to generate metal copper in situ, thereby functioning as an active component. The component including copper may exist in the form of solid particles, powder, or crystals. In some embodiments, the average particle size of the component including copper may be in the range of 20 micrometers to 1700 micrometers, 25 micrometers to 1500 micrometers, 40 microns to 1000 microns, 50 microns to 500 microns, or 100 microns to 200 microns, or greater than 20 microns, greater than 23 microns, greater than 25 microns, greater than 30 microns, greater than 40 microns, greater than 50 microns, or less than 1700 microns, less than 1500 microns, less than 1200 microns, less than 1000 microns, less than 800 microns, less than 600 microns, or less than 500 microns, or the like.

The auxiliary agent may aid in the diffusion and/or contact between the reaction materials (e.g., biological object particles, water, and the other components in the catalyst) to facilitate the reaction. Under the condition of heating and stirring, the auxiliary agent may also rub against the walls of the degradation reactor and the copper catalyst adsorbing on the walls to "wash," "scrape" or "sweep" the metallic copper, thereby weakening the wall adsorption property of the metallic copper. Thus, in the presence of the auxiliary agent, the copper in the catalyst component may be more fully contacted with the biological object particles to facilitate the reaction. The auxiliary agent may not participate in the catalytic reaction. In some embodiments, the auxiliary agent may be a quartz sand, a diamond, silicon carbide, a diatomaceous earth, a ceramic material, or the like, or any combination thereof. The quartz sand, the diamond, the silicon carbide, the diatomaceous earth, and the ceramic materials are inherently difficult to react with the biological object, hydrogen or the components including copper. The particle size of the auxiliary agent may affect the effect of cleaning the metallic copper. In some embodiments, the average particle size of the auxiliary agent is in the range of 0.5 mm to 32 mm, 1 mm to 16 mm, or 2 mm to 8 mm.

The catalyst component may also include a cocatalyst component. According to some embodiments, the catalyst component may include a cocatalyst component with a mass fraction of 0.05% to 50%. The cocatalyst component may assist the catalyst including copper to modulate the degradation catalytic activity and selectivity of the catalyst. The cocatalyst component may also aid in the bond breaking and/or dissociation of hydrogen molecules. In some embodiments, the cocatalyst component may be a transition metal, a transition metal oxide, a transition metal salt, or the like, or any combination thereof. In some embodiments, the cocatalyst component may include a metal (e.g., a zirconium, a manganese, a zinc, a cobalt, a tungsten), a metallic oxide (e.g., an oxide of zirconium, an oxide of manganese, an oxide of zinc, an oxide of cobalt, an oxide of tungsten), and a metal salt (e.g., a zirconium salt, a manganese salt, a zinc salt, a cobalt salt, a tungsten salt), or the like, or any combination thereof. For example, the cocatalyst component may include a metal (e.g., a zirconium, a manganese, a zinc, a cobalt, a tungsten), a metallic oxide (e.g., an oxide of zirconium, an oxide of manganese, an oxide of zinc, an oxide of cobalt, an oxide of tungsten), and a metal salt (e.g., a zirconium salt, a manganese salt, a zinc salt, a cobalt salt, a tungsten salt), or the like, or any combination thereof.

According to some embodiments of the present disclosure, FIG. 8-C is a shematic diagram illustrating an exemplary hydrolysis mechanism of cellulose. Under the condition of heating, hemicellulose and cellulose may be hydrolyzed to generate the corresponding monosaccharides. This process may be accelerated in the presence of the copper catalyst. The copper catalyst has a large specific surface area, for example, the specific surface area of the copper catalyst per unit mass may be on the order of 10 square meters per gram. The copper catalyst may be capable of adsorbing hydrogen at a higher temperature (e.g., above 100° C.) and a certain hydrogen atmosphere (e.g., 0.1 MPa hydrogen partial pressure). A part of the adsorbed hydrogen may exist in the form of atomic hydrogen, which may lose one electron to obtain hydrogen ions. Therefore, the solution of the degradation reaction system may exhibit a certain acidity.

The oxygen on a β-1,4-glycosidic bond is protonated by accepting a hydrogen ion when the hydrogen ion is contacted with the β-1,4-glycosidic bond on a cellulose chain, to obtain a conjugate acid, in which the glycosidic bond is broken and reacts with water to obtain a hydroxyl group while releasing a hydrogen ion that may catalyze the hydrolysis reaction again. The hydrolysis reaction is continued until hydrolyzable C—O—C bonds are completely reacted or the conditions of the hydrolysis reaction are no longer exist (the acidity or the temperature of the system is decreased, etc.).

The hydrolysis mechanism of hemicellulose is similar to that of cellulose. Hydrogen ions may rapidly protonate the oxygen atom of the glycosidic bond in the hemicellulose macromolecule to obtain a conjugate acid, which may weaken and break the glycosidic bond. The positive carbon ions generated by the broken of the glycosidic bond may react with water to obtain a monosaccharide, and at the same time release hydrogen ions. Hydrogen ions may continue to participate in new hydrolysis reactions.

Unlike the more active catalysts such as iron, zinc or nickel, metallic copper has a low activity and is difficult to react with hydrogen ions in acidic systems. Therefore, the copper catalyst may maintain catalytic activity for a long time without being dissolved in the acidic solution formed by the degradation reaction.

It is worth noting that the degradation reaction is carried out in an environment with a high temperature and high partial pressure of hydrogen. Under such an environment, some compounds including copper, such as copper oxide, cuprous oxide or basic copper carbonate, may be reduced to elemental copper. The elemental copper generated in situ may also be used as a catalyst active component. Therefore, the catalyst component may include no metal elemental copper, but only a copper compound, such as a copper oxide, a copper salt, or the like, or any combination thereof.

Figure 9:
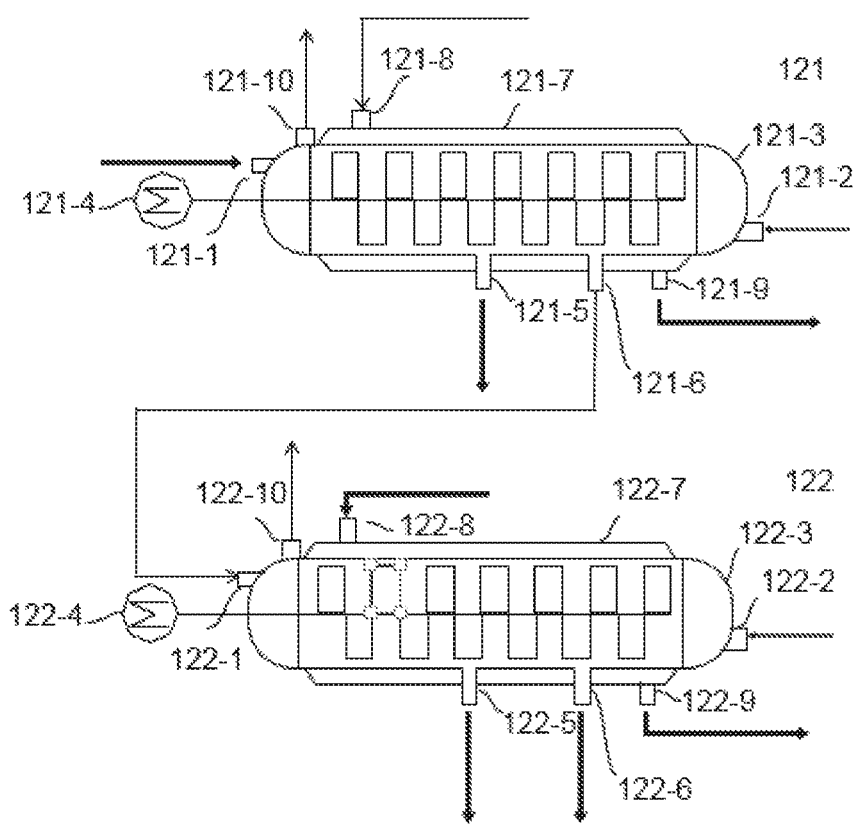
FIG. 9 is a shematic diagram illustrating an exemplary degradation reactor according to some embodiments of the present disclosure.

According to some embodiments of the present disclosure, FIG. 9 is a shematic diagram illustrating an exemplary degradation reactor. In some embodiments, the degradation reactor may degrade the biological object to obtain a sugar-including solution and a solid residue. In some embodiments, the degradation reactor may include a degradation reactor 121 and a degradation reactor 122. The degradation reactor may also have only one degradation reactor 121.

In some embodiments, the degradation reactor 121 may be a reactor in which the biological object undergoes a first-stage degradation reaction. The degradation reactor 121 may include one or more feed ports 121-1, one or more air inlets 121-2, a chamber 121-3, one or more agitators 121-4, one or more sugar solution discharge ports 121-5, one or more solid residue discharge ports 121-6, a fluid conduit 121-7, one or more fluid inlets 121-8, one or more fluid outlets 121-9, and one or more air outlets 121-10.

When the degradation reactor 121 works, the feed port 121-1 may be used to feed non-gaseous reactants. The non-gaseous reactants herein may be the biological object, the catalysts, and water, or the partially degraded biological object, the catalysts, and water, or a mixture of the biological object and the partially degraded biological object, the catalysts, and water. In some embodiments, a non-gaseous reactant may be delivered from the feed port 121-1 into the chamber 121-3 using a screw pump. The screw pump here may be a positive displacement rotor pump that relies on the volume change of the sealed chamber formed by the screw and the bushing to draw in and discharge non-gaseous reactants.

The air inlet 121-2 may be used for gas input, and the air outlet 121-10 may be used for gas discharge. The gas herein may be hydrogen, oxygen, air, nitrogen, argon, ozone, chlorine, carbon dioxide, or a mixed gas thereof. The air inlet 121-2 and the feed port 121-1 may be of the same structure or different structures. The air outlet 121-10 and the sugar solution discharge port 121-5 or the solid residue discharge port 121-6 may be of the same structure or different structures. In some embodiments, the feed port 121-1 and the air inlet 121-2 may be respectively located at both ends of the axial direction of the reactor 121 such that the feed direction is opposite to the air intake direction, so that the reactants and the gas may be sufficiently contacted. The axial direction described here refers a direction parallel to the stirring shaft of the agitator 121-4. In some embodiments, the air outlet 121-10 and the air inlet 122-2 in the reactor 122 may be connected or disconnected. In some embodiments, the air outlet 121-10 and the air inlet 122-2 in the reactor 122 may be connected through a conduit. In some embodiments, the conduit may be fitted with a valve, and whether the air outlet 121-10 and the air inlet 122-2 in the reactor 122 may be connected to form as a whole may be controlled by a switch of the valve.

The entry of non-gaseous reactants and gaseous reactants through the feed port 121-1 and the air inlet 121-2 may be continuous or discontinuous.

The chamber 121-3 may accommodate reactants such as the biological object, the catalyst components, water, and gases. An atmosphere may also be formed in the chamber 121-3. For example, the atmosphere may include hydrogen and have certain pressure. Under the condition of heating and stirring, the biological object may undergo a degradation reaction in the chamber 121-3. The chamber 121-3 may be made of an acid-resistant material, an alkali-resistant material, a high-temperature resistant material, a pressure-resistant material or a wear-resistant material, for example, metals or alloys (copper, rare earth metals, stainless steel, ductile iron, manganese steel, brass, bronze, white copper, solder, hard aluminum), inorganic materials (ceramics, graphene), polymer materials (organic glass, phenolic resin, ABS resin, polytetrafluoroethylene, polyvinyl chloride), composite materials (color steel plate, glass steel), or any combination of the above materials. The catalyst component exiting in the form of particles or powder may adsorb on the walls of the chamber 121-3 when stirring at high temperatures. The adsorption may result in a decrease amount of effective catalysts actually participating in the degradation reaction, which is detrimental to the degradation reaction. In order to reduce the wall adsorption property of the catalyst, the inner wall of the chamber 121-3 may be processed by certain treatment to cause the inner wall of the chamber 121-3 flatter and smoother. The treatment may be chemical treatment, physical treatment, or a combination thereof. The chemical treatment may be chemical modification or treatment of the inner wall, for example, formation of an oxide film, formation of a nitride film, chemical oxidation and surface modification, or the like. The physical treatment may include coating, polishing, sanding, milling, and extrusion.

The agitator 121-4 may be used to agitate and mix the reactants, and may increase the number of collisions between the reactants. The contact times of the reactants with the inner wall of the chamber 121-3 may be also increased by stirring, so that the non-gaseous reactant continuously washes the inner wall surface of the chamber 121-3, reducing the wall adsorption property of the catalyst, thereby increasing the use efficiency of the catalyst. According to the mechanical structure of the agitator, the agitator 121-4 may be a propeller agitator, a turbine agitator, a paddle agitator, an anchor agitator, a ribbon agitator, a magnetic agitator, a hinged agitator, a variable frequency double agitator or a side-in agitator, or the like. According to some embodiments of the present disclosure, the agitator 121-4 may include a stirring rod with one or more blades. The plane of the blade may be parallel to the central axis of the stirring rod. The blade may be evenly/non-unevenly distributed over different longitudinal heights of the central axis of the stirring rod. The number of blades per longitudinal height may be one or more. The number of blades at different longitudinal heights may be the same or different. In order to reduce the adsorption of the catalyst on the surface of the agitator 121-4, the surface of the agitator 121-4 may be processed by certain treatment to make the surface of the agitator 121-4 flatter and smoother. The treatment method may be the same as or different from the treatment of the inner wall of the chamber 121-3.

The sugar solution discharge port 121-5 may be configured to discharge the sugar-including solution. The sugar-including solution herein may be delivered to a sugar solution buffer tank or a sugar solution storage tank. For example, the sugar solution discharge port 121-5 may be located below the reactor 121. In some embodiments, the sugar solution discharge port 121-5 may include a filter. The filter may initially filter the mixture in chamber 121-3 to reduce or avoid solid phase residues from flowing out of the sugar solution discharge port 121-5.

The solid phase residue discharge port 121-6 may be configured to discharge a solid phase residue. The solid residue may be a mixture of the partially degraded biological object and the catalyst. For example, the solid residue discharge port 121-6 may be located below the degradation reactor 121. In order to make the sugar solution and the solid phase residue being discharged more smoothly, the reactor 121 may be placed obliquely so that the sugar solution and the solid phase residue may be discharged by gravity. In some embodiments, the sugar solution and the solid residue may be discharged by introducing a high pressure gas into the chamber 121-3. The high pressure described here refers to the pressure greater than one atmosphere, for example, 110 kPa, 120 kPa, or higher.

The fluid conduit 121-7, fluid inlets 121-8, and fluid outlets 121-9 may collectively constitute a heating device for the reactor 121. The heating device herein may be configured to heat the chamber 121-3, thus heating the biological object, the catalyst, water, and the gas placed in the chamber 121-3 to obtain a sugar-including solution and a solid phase residue. The heating device may be heated using a fluid. The fluid herein may include water, water steam, superheated air, heat transfer oil, or the like. The fluid may be introduced into the fluid conduit from the fluid inlet 121-8. The fluid conduit 121-7 may be distributed inside or on the surface of the chamber 121-3, so that the fluid is sufficiently exchanged with biological object, catalyst, water, and the gas in heat. After heat exchange, the fluid may exit the fluid conduit 121-7 from the fluid outlet 121-8.

It should be noted that the above examples are for convenience of description only and do not constitute a limitation on the present disclosure. Those skilled in the art will appreciate that many variations and modifications may be made in the disclosure of the present disclosure. Although a heating device utilizing the principle of fluid heat exchange is used herein, other types of heating devices may be used in the degradation reactor 121. For example, an electric heating device, a high frequency heating device, or a microwave heating device. These variations or improvements are covered by the present disclosure.

In some embodiments, the degradation reactor 122 may be a reactor in which the biological object undergoes a second-stage degradation reaction. The degradation reactor 122 may have the same structure as the degradation reactor 121. The degradation reactor 122 may also have a different structure from the degradation reactor 121. The degradation reactor 122 may include one or more feed ports 122-1, one or more air inlets 122-2, a chambers 122-3, one or more agitators 122-4, one or more sugar solution discharge ports 122-5, one or more solid phase residue discharge ports 122-6, a fluid conduit 122-7, one or more fluid inlets 122-8, one or more fluid outlets 122-9, and one or more air outlets 122-10.

When the degradation reactor 122 works, the feed port 122-1 may be used to feed non-gaseous reactants. The non-gaseous reactants may be a solid phase residue that is discharged by the solid residue residue port 121-6. In some embodiments, the feed port 122-1 of the reactor 122 and the solid residue discharge port 121-6 of the reactor 121 may be connected or disconnected. In some embodiments, the feed port 122-1 and the solid residue discharge port 121-6 may be connected through a conduit (not shown). In some embodiments, the conduit may be fitted with a valve, and whether the degradation reactor 121 and the degradation reactor 122 may be connected to form as a whole may be controlled by a switch of the valve.

The structure, function, parameters, materials, etc. of the air inlet 122-2, the chamber 122-3, the agitator 122-4, the sugar solution discharge port 122-5, the solid residue discharge port 122-6, the fluid conduit 122-7, the fluid inlet 122-8, and the fluid outlet 122-9, and the air inlet 121-2, the chamber 121-3, the agitator 121-4, the discharge port 121-5, the solid residue discharge port 121-6, the fluid conduit 121-7, the fluid inlet 121-8, and the fluid outlet 121-9 in the degradation reactor 121 may be the same or different. The mixed solution of the dilute sugar and the inorganic salt obtained by the degradation reactor 122 may be discharged from the sugar solution discharge port 122-5 to the sugar solution buffer tank or to the sugar solution storage tank. The solid residue obtained by the degradation reactor 122 may be discharged through the solid residue discharge port 122-6. The solid residue may be further processed, for example, the recovery of the catalyst and the extraction of lignin may be performed.

The above description of the degradation reactor is merely a specific example and should not be considered as the only feasible embodiment. Obviously, for those skilled in the art, after understanding the basic principles of the work of the degradation reactor, various modifications and changes in the form and details of the specific embodiment and steps of the degradation reactor may be carried out without departing from this principle. However, these modifications and changes are still within the scope of the above description. In some embodiments, the degradation reactor may include one or more reactors. For example, the number of reactors may be from 1 to 6, or from 2 to 4, or the like. Each reactors may exist independently or be connected in a certain way to form as a whole. In some embodiments, the fluid outlet 121-9 and the fluid inlet 122-8 may be connected or disconnected. In some embodiments, the fluid outlets 121-9 and the fluid inlets 122-8 may be connected through a conduit. In some embodiments, the conduit may be fitted with a valve, and whether the fluid conduit 121-7 and the fluid conduit 122-7 may be connected to form as a whole may be controlled by a switch of the valve. When the valve is opened, the degradation reactor 121 and the degradation reactor 122 may perform heat exchange and materials transportation. In some embodiments, the outer layers of the fluid conduit 121-7 and the fluid conduit 122-7 may be fitted with a thermal insulation sleeve, and the thermal insulation sleeve may reduce heat loss and improve insulation efficiency. Such variants are covered by the present disclosure.

Figure 10:
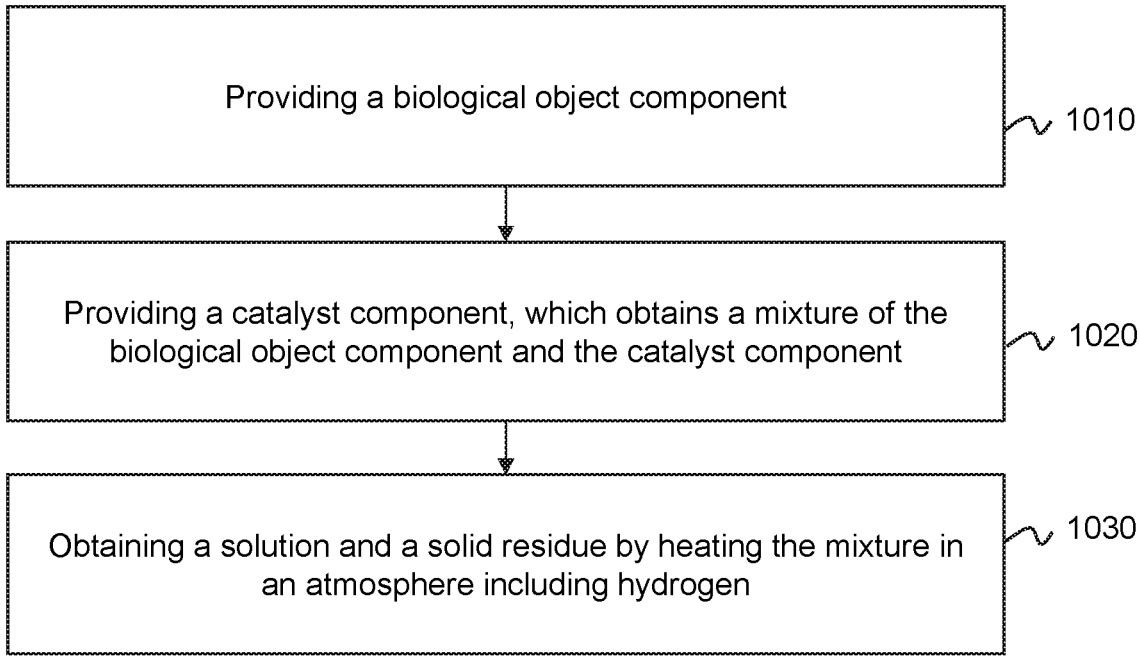
FIG. 10 is a flowchart illustrating an exemplary process for a first-stage reaction of biological object degradation according to some embodiments of the present disclosure.

According to some embodiments of the present disclosure, FIG. 10 is a flowchart illustrating an exemplary process for a first-stage reaction of biological object degradation.

In 1010, a biological object component is provided. The biological object component herein may be the biological object without degradation, the partially degraded biological object, or a mixture of the biological object without degradation and the partially degraded biological object, etc. In some embodiments, the partially degraded biological object may be a solid phase residue that is discharged through the degradation reactor. When the biological object is partially degraded, a lot of pores may be formed on the surface of the biological object, and the three-dimensional structure of the biological object may be destroyed. After the reaction, the biological object particles may transform into a porous form with many whisker-like branches and a core. These branches may prevent the core of the biological object from contacting the catalyst, thus hindering the degradation of the biological object. In order to improve the conversion rate of the biological object degradation, the flocculated biological object may be mechanically treated to destroy the flocculated form of the biological object, making it easy to be degraded. In some embodiments, the mechanical processing may include compaction, extrusion, etc.

In 1020, a catalyst component is provided, obtaining a mixture with the biological object component provided in 1010. The catalyst here may be used to catalyze the degradation of the biological object, accelerate the reaction process of the biological object degradation, improve the conversion rate of the biological object degradation, and may be recycled after treatment. The specific components and contents of the catalyst are described in detail below. The mass ratio of the catalyst to the biological object may be 1:100 to 200:100, 10:100 to 100:100, 10:100 to 70:100, 10:100 to 50:100, 20:100 to 45:100, or 30:100 to 40:100. In some embodiments, water may be provided simultaneously in 1020.

In 1030, the mixture obtained in 1020 is heated in an atmosphere including hydrogen to obtain a solution and a solid residue. The atmosphere including hydrogen here may have hydrogen pressure.

In a hydrogen atmosphere, hemicellulose and cellulose in the biological object may be degraded to obtain monosaccharides and polysaccharides by heating. In some embodiments, the moisture included in the biological object is released by heating. Monosaccharides and polysaccharides may be dissolved in water together with substances such as inorganic salts originally present in the biological object to obtain a solution. The undegraded biological object (including residual cellulose and hemicellulose, lignin and other water-insoluble components, etc.) and catalyst components may form a solid phase residue.

Under the experimental conditions in the present disclosure, the hemicellulose degradation rate in the biological object is faster than the cellulose degradation rate, and the lignin is basically not degraded. The hemicellulose in the biological object may be selectively hydrolyzed by controlling the time of degradation. In this case, the main components of the undegraded biological object are lignin and cellulose. After lignin is extracted, the remaining biological object component is predominantly cellulose. The obtained cellulose with higher purity may be used in other industries or agriculture, for example, papermaking and manufacture of cellulose sheets.

The heating of the mixture may be accompanied by stirring. Heating and stirring are both designated to promote the contact and collision between the biological object, the catalyst, water, and hydrogen.

The degradation catalyst used in the present disclosure includes copper powder, which easily adsorbs on the inner wall of the degradation reactor. Under a condition of stirring, the large biological object particles may continuously flush the copper adsorbing on the inner wall of the degradation reactor, which makes the adsorbing copper into the reaction system, thereby increasing the reaction rate of degradation. However, if the biological object particles are too large, the specific surface area of the biological object is too small, then the contact between the biological object and the catalyst is insufficient, and the reaction rate of degradation is decreased.

The degradation reaction in the present disclosure occurs under certain reaction pressure. When the hydrogen pressure is too large, the sugar obtained by the degradation may be converted into sugar alcohols; and the greater the reaction pressure, the higher the requirement for the device.

The conversion rate of the biological object degradation may be increased by increasing the reaction time. However, when the reaction time is too long, a complicated conversion process may occur between the generated sugars, and by-products such as sugar alcohols and small molecular alcohols may be generated. In addition, the longer the degradation reaction time, the longer the reaction cycle and the more energy and resources are consumed.

The degradation reaction rate may be increased by increasing the heating temperature. However, if the heating temperature is too high, the generated sugar may also shrink (coking or charring) to generate impurities such as caramel and coke.

In some embodiments, both the catalyst and water are provided in 1020. The catalyst, water, and the biological object together form a mixture. The solid-liquid ratio in the mixture refers to the ratio of the mass of the biological object to the water. The larger the solid-liquid ratio, the more difficult it is to stir, the less contact between the biological object and the catalyst, and the lower the reaction rate is.

The solid-solid ratio in the present disclosure refers to the mass ratio of the catalyst to the biological object. If the the solid-solid ratio is increased, the amount of the catalyst will be increased and the reaction rate will be increased. However, when the amount of the catalyst reaches a certain amount, the degradation rate tends to be stable. The faster the stirring speed, the more frequent contact of the biological object with the catalyst, the biological object with the water, and the catalyst with the water.

In order to understand the influence of different factors on the degradation reaction, and determine the appropriate range of reaction conditions, a plurality of experiments were designed. In the experiment, rice straw was used as raw materials for the biological object. The effects of the rice straw particle size, the reaction temperature, the solid-solid ratio (a mass ratio of the catalyst to the straw), the solid-liquid ratio (a mass ratio of the straw to water), the stirrer rotation speed, the hydrogen pressure, and the reaction time on the biological object degradation reaction were investigated by single factor experiments. Specific experimental operations and results are described in detail in Example 1 to Example 7.

In the reaction of straw degradation, when the other experimental conditions were fixed, if the straw particles were too large or too small, the degradation rate of the straw and the concentration of the sugar solution obtained by the degradation were all decreased. The size of the straw particles may in a range from 10 meshes to 300 meshes, 20 meshes to 100 meshes, or 20 meshes to 60 meshes.

When the other experimental conditions were fixed, with the increase of the hydrogen pressure, the degradation rate of straw and the concentration of sugar solution obtained by degradation were all decreased, and the concentration of the sugar solution decreased more greatly. The reaction pressure may be in a range from 1.0 MPa to 6.0 MPa, 1.5 MPa to 4.0 MPa, 1.0 MPa to 4.0 MPa, 1.5 MPa to 3.0 MPa, or 1.5 MPa to 2.0 MPa, etc.

When the other experimental conditions were fixed, under different reaction times, the degradation rate of the straw changed little, and the concentration of the sugar solution changed more greatly. The reaction time may be from 0.5 hour to 20.0 hours, 1.0 hour to 10.0 hours, 2.0 hours to 4.0 hours, or 2.0 hours to 3.0 hours, or the like.

When the other experimental conditions were fixed, if the temperature was too high or too low, the degradation rate of the straw and the concentration of the sugar solution obtained by the degradation were all decreased. The reaction temperature may be from 100° C. to 170° C., 110° C. to 160° C., 130° C. to 150° C., or 140° C., or the like.

When the other experimental conditions were fixed, if the solid-liquid ratio was too high or too low, the degradation rate of the straw and the concentration of the sugar solution obtained by the degradation were all decreased. The solid-liquid ratio may be in a range of 1:6 to 1:12, 1:7 to 1:11, or 1:8 to 1:10, or the like.

When the other experimental conditions were fixed, if the solid-solid ratio was too high or too low, the degradation rate of the straw and the concentration of the sugar solution obtained by the degradation were all decreased. The solid-solid ratio may be in a range of 1:100 to 200:100, 10:100 to 100:100, 10:100 to 70:100, 10:100 to 50:100, 20:100 to 45:100, or 30:100 to 40:100, etc.

When the other experimental conditions were fixed, under different stirring speeds, the degradation rate of the straw changed little while the concentration of the sugar solution changed more greatly. The stirring speed may be from 400 rpm to 800 rpm, 500 rpm at 700 rpm, 600 rpm to 700 rpm, or 600 rpm.

The above description of the process for the first-stage reaction of biological object degradation is only a specific example and should not be considered as the only feasible embodiment. Obviously, for those skilled in the art, after understanding the basic principles of biological object degradation reaction, various modifications and changes in the form and details of the biological object degradation reaction may be carried out without departing from this principle. However, these modifications and changes are still within the scope of the above description. In some embodiments, the mixing mode of the catalyst, water, and the biological object may be changed. For example, water and the straw may be mixed first, and then the mixture of water and the straw may be mixed with the catalyst. For example, the straw and the catalyst may be mixed first, and then the mixture of the straw and the catalyst may be mixed with water. For example, the straw, water, and the catalyst may be mixed at the same time. Such variants are covered by the present disclosure.

Figure 11:
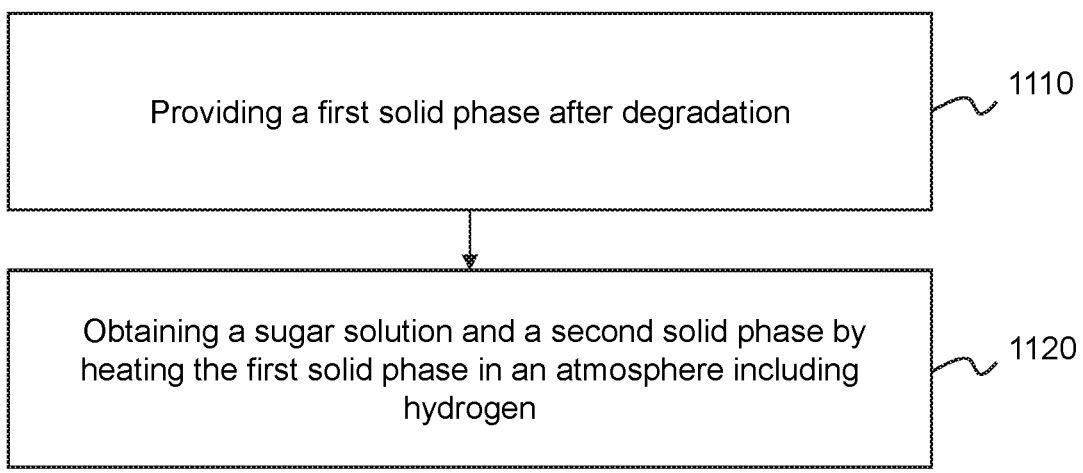
FIG. 11 is a flowchart illustrating an exemplary process for a second-stage reaction of biological object degradation according to some embodiments of the present disclosure.

According to some embodiments of the present disclosure, FIG. 11 is a flowchart illustrating an exemplary process for a second-stage reaction of biological object degradation.

In 1110, a first solid phase after degradation is provided. The first solid phase after degradation may be a solid phase residue of the biological object after degradation, including cellulose, lignin, and the degradation catalyst. In some embodiments, the first solid phase after degradation may be a solid phase residue obtained in the first-stage reaction of biological object degradation.

In some embodiments, in 1110, an additional degradation catalyst may be also provided, and the additional degradation catalyst may be mixed with the first solid phase. The degradation catalyst herein and the catalyst described in 1020 of FIG. 10 may be the same or different, and the specific catalyst components and contents are described in detail below. The amount of the catalyst (herein refers to a mass ratio of the catalyst to the first solid phase) may be 1% to 200%, 10% to 100%, 20% to 70%, or 30% to 40%, etc.

In 1120, the first solid phase is heated in an atmosphere including hydrogen to obtain a sugar solution and a second solid phase. The atmosphere including hydrogen herein may have hydrogen pressure. In some embodiments, the pressure of the atmosphere including hydrogen may be the same as or different from the pressure of the atmosphere including hydrogen in the first-stage reaction of biological object degradation.

In a hydrogen atmosphere, hemicellulose and cellulose in the first solid phase may undergo a degradation reaction to generate monosaccharides and polysaccharides by heating. Monosaccharides and polysaccharides may be dissolved in water together with substances such as inorganic salts originally present in the biological object to obtain a solution. The undegraded biological object (including residual cellulose and hemicellulose, lignin and other water-insoluble components, etc.) and the catalyst components may form a second solid phase.

Like the first-stage reaction of biological object degradation, the second-stage reaction of biological object degradation is also affected by many factors, including the particle size of the biological object, the reaction time, the reaction pressure, the reaction temperature, the solid-liquid ratio (a mass ratio of the straw to water), the solid-solid ratio (a mass ratio of the catalyst to the straw), and the stirring speed. In the process for the second-stage reaction of biological object degradation, the values of the factors affecting the second-stage reaction of biological object degradation may be the same as or different from the values of the factors of the first-stage reaction of biological object degradation.

In some embodiments, the size of the straw particles may be in a range from 10 meshes to 300 meshes, 20 meshes to 100 meshes, or 20 meshes to 60 meshes, etc.

In some embodiments, the reaction pressure may be in a range from 1.0 MPa to 6.0 MPa, 1.5 MPa to 4.0 MPa, 1.5 MPa to 3.0 MPa, or 1.5 MPa to 2.0 MPa.

In some embodiments, the reaction time may be from 0.5 hour to 20.0 hours, 2.0 hours to 4.0 hours, or 2.0 hours to 3.0 hours.

In some embodiments, the temperature of the reaction may be in a range from 100° C. to 170° C., 120° C. to 160° C., 130° C. to 150° C., or 140° C.

In some embodiments, the solid-liquid ratio may be 1:6 to 1:12, 1:7 to 1:11, or 1:8 to 1:10.

In some embodiments, the solid-solid ratio may be 1:100 to 200:100, 10:100 to 100:100, 10:100 to 70:100, 10:100 to 50:100, 20:10 to 45:100, or 30:100 to 40:100.

In some embodiments, the stirring speed may be about 400 to 800 rpm, 500 to 700 rpm, or 600 to 700 rpm. In some embodiments, the stirring speed may be about 400 rpm, 500 rpm, 600 rpm, 700 rpm, or 800 rpm.

Figure 12:
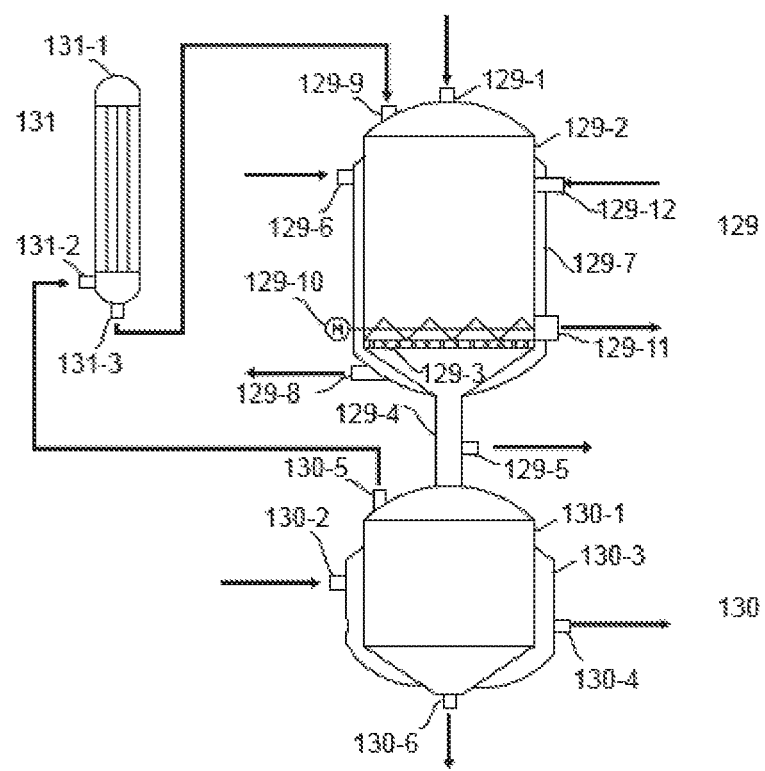
FIG. 12 is a shematic diagram illustrating an exemplary washing filter according to some embodiments of the present disclosure.

According to some embodiments of the present disclosure, FIG. 12 is a shematic diagram illustrating an exemplary washing filter. In some embodiments, the washing filter may be configured to extract one or more components from a mixture. The mixture here may be a mixture of a solid residue of the biological object degradation reaction and sugary solutions. For example, the washing filter may be configured to extract the sugar and/or the other soluble components, such as inorganic salts, in the mixture of the solid residue after the biological object degradation reaction and sugar solutions.

The washing filter may be a single device, or a combination of several devices. In some embodiments, the washing filter may include, but is not limited to, a first chamber 129, a second chamber 130, and a condensing device 131. In some embodiments, the first chamber 129 may be located in the upstream of the fluid flow of the second chamber 130.

In some embodiments, the first chamber 129 may include one or more solid feed ports 129-1, a chamber 129-2, one or more filter devices 129-3, one or more connection devices 129-4, one or more condensate inlets 129-9, one or more discharge devices 129-10, one or more discharge ports 129-11, and one or more sugar solution feed ports 129-12.

In some embodiments, the solid feed port 129-1 may be used for the feed of solid residues. In some embodiments, the solid residue may be from the solid residue discharge port 121-6 or 122-6. In some embodiments, the solid feed port 129-1 may be located at or near the top of the mixing chamber 129-2 or may be located at the side wall of the mixing chamber 129-2. In some embodiments, the solid feed port 129-1 may be connected to a solid residue discharge port (e.g., 121-6 or 122-6) of the degradation reactor. The solid residue formed after the biological object degradation may be removed from the solid residue discharge port 121-6 or 122-6, and introduced into the washing filter through the solid feed port 129-1.

In some embodiments, the sugar-including solution may be fed into the mixing chamber 129-2 by the sugar solution feed port 129-12. In some embodiments, the sugar-including solution may be from the sugar solution discharge port 121-5 or 122-5, from a washing liquid outlet 130-6, or from a dilute sugar storage tank. The sugar solution feed port 129-12 may be located at or near the top of the mixing chamber 129-2, or be located on the side walls of the mixing chamber 129-2. In some embodiments, the sugar solution feed port 129-12 may be connected to the sugar solution discharge port (e.g., 121-5 or 122-5) of the degradation reactor. In some embodiments, the sugar solution feed port 129-12 and the solid feed port 129-1 may be of the same structure, or different structures.

In some embodiments, the mixing chamber 129-2 may be configured to accommodate the mixture and the washing liquid.

In some embodiments, the filter device 129-3 may be configured to filter the washing liquid. The filter device 129-3 may be located inside the mixing chamber 129-2. The filter device 129-3 may be located in the downstream of the fluid flow of the discharge device 129-10 and/or the discharge port 129-11. The filter device 129-3 may be a strainer, a mesh screen, a filter paper, a filter cloth, a filter cotton, or the like, or any combination thereof. The filter device may have a certain number of pores. The pore size allows for the passage of water or a solution and prevents the passage of solid particles larger than the pore size. In some embodiments, filter devices with different pore sizes may be selected according to the size of the catalyst and/or the biological object.

In some embodiments, the connection device 129-4 may be configured to connect the mixing chamber 129-2 and the washing liquid chamber 130-1, so that the washing liquid may flow from the mixing chamber 129-2 into the washing liquid chamber 130-1. One end of the connection device 129-4 may be connected to the bottom, a place near the bottom, or the side wall of the mixing chamber 129-2, and the other end may be connected to the top, a place near the top, or the side wall of the washing liquid chamber 130-1. The connection between the connection device 129-4 and the mixing chamber 129-2 and/or the washing liquid chamber 130-1 may be detachable or non-removable.

In some embodiments, the condensed washing liquid may be introduced into the mixing chamber 129-2 from the condensate inlet 129-9. The condensed washing liquid may be in contact with the mixture, and extract the components in the mixture. In some embodiments, the condensate inlet 129-9 may be located at or near the top of the mixing chamber 129-2, or on the side wall of the mixing chamber 129-2.

In some embodiments, the discharge device 129-10 may be configured to discharge, from the mixing chamber 129-2, the mixture after extracting the components (e.g., a mixture of the solid residue and water after the sugar is extracted). The discharge device 129-10 may be connected to the discharge port 129-11. In some embodiments, the discharge device 129-10 may be similar to the dispensing device described in FIG. 7-B.

In some embodiments, the mixture after extracting the components (e.g., a mixture of the solid residue and water after the sugar is extracted) may be discharged from the discharge port 129-11 for further processing (e.g., the separation of lignin from catalysts or the recovery of catalysts). The discharge port 129-11 may be located on the side wall of the mixing chamber 129-2 or on the discharge device 129-10. In some embodiments, the second chamber 130 may include a washing liquid chamber 130-1, one or more steam outlets 130-5, one or more washing liquid outlets 130-6, and one or more first heating devices.

In some embodiments, the washing liquid chamber 130-1 may be configured to accommodate the washing liquid and the washing liquid steam.

In some embodiments, the steam outlet 130-5 may be configured to discharge the washing liquid steam. The steam outlet 130-5 may be located at or near the top of the washing liquid chamber 130-1.

In some embodiments, the washing liquid outlet 130-6 may be configured to discharge a pure washing liquid or a washing liquid in which the extracted component is dissolved. The washing liquid outlet 130-6 may be located at or near the bottom of the washing liquid chamber.

In some embodiments, the first heating device may be configured to heat the washing liquid to steam, and then the steam is discharged from the steam outlet 130-5. After the steam has been condensed into a liquid, the liquid is sent to the mixing chamber 129-2 to be in contact with the mixture to extract components. In some embodiments, the first heating device may include one or more heating substance inlets 130-2, one or more heating jackets 130-3, and one or more condensate outlets 130-4. The heating substance inlet 130-2 may be configured to introduce a heated substance. The heating substance may be steam, hot water, hot oil, or the like. The condensate outlet 130-4 may be configured to discharge the cooled heating substance. The heating jacket 130-3 may be configured to transfer the heat of the heating substance to the washing liquid through the washing liquid chamber 130-1, thereby achieving the purpose of heating the washing liquid to turn the washing liquid into steam. In some embodiments, the heating jacket 130-3 may be located outside of the washing liquid chamber 130-1. In some embodiments, the heating substance may be introduced into the heating jacket 130-3 from the heating substance inlet 130-2, and then be discharged from the condensate outlet 130-4 by cooling. In some embodiments, the heating substance introduced into the heating jacket 130-3 may be replaced by a heating structure placed inside the heating jacket 130-3, for example, a resistance wire, or the like. In some embodiments, the heating structure (e.g., the resistance wire) may be directly placed outside the washing liquid chamber 130-1 without providing a heating jacket.

In some embodiments, the washing liquid chamber 130-1 may be in contact with the heat transfer medium to cause the washing liquid to be heated to become steam. The heat transfer medium may be water, oil, or the like. For example, a water bath pot and an oil bath pot may be used as the first heating device to heat the washing liquid. In some embodiments, the washing liquid chamber 130-1 may be directly in contact with a heat source to cause the washing liquid to be heated to become steam. The heat source may be an electric heater or a fuel heater. In some embodiments, the electric heater may be an electromagnetic heater, an infrared heater, or a resistance heater. In some embodiments, the first heating device may be directly in contact with the washing liquid, so that the washing liquid is heated to become steam. For example, a heating rod, a heating tube, and/or a heating sheet may be directly in contact with the washing liquid as the first heating device, so that the washing liquid is heated to become steam.

In some embodiments, the solid feed port 129-1, the discharge port 129-11, the washing liquid outlet 130-6, and the sugar solution feed port 129-12 may include, but are not limited to, one or more sealing devices. The sealing device may be configured to seal the solid feed port 129-1, the discharge port 129-11, the washing liquid outlet 130-6, and the sugar solution feed port 129-12, thereby making the first chamber 129 and the second chamber 130 become a sealed container, and/or controlling the entry and discharge of substances. In some embodiments, the sealing device may be a valve, a sealing cover, a piston, a hydraulic seal, a pneumatic seal, or the like, or any combination thereof.

In some embodiments, the condensing device 131 may be configured to convert the washing liquid steam into a liquid by transferring heat to a nearby heat transfer medium (e.g., air, a refrigerating gas, a refrigerating liquid, etc.). The condensing device 131 may include, but is not limited to, a condensing chamber 131-1, one or more feed ports 131-2, and one or more discharge ports 131-3. The condensing chamber 131-1 may be used to accommodate a heat transfer medium, washing liquid steam, and/or a washing liquid. In some embodiments, the condensing chamber 131-1 may further include one or more recirculation chambers. The recirculation chamber may be used to accommodate the washing liquid steam and/or the washing liquid, and the outside of the recirculation chamber may accommodate a heat transfer medium to transfer heat from the recirculation chamber to the heat transfer medium to cause the washing liquid steam to become a liquid. In some embodiments, the feed port 131-2 may be used to feed the washing liquid steam. The feed port 131-2 may be located at or near the top or bottom, and/or on the side wall of the condensing chamber 131-1. The feed port 131-2 may be connected to the steam outlet 130-5. In some embodiments, an insulating device may be placed between the feed port 131-2 and the steam outlet 130-5 to reduce or prevent the washing liquid steam from entering the condensing chamber 131-1 due to condensation during the process of entering the feed port 131-2 from the steam outlet 130-5. In some embodiments, the discharge port 131-3 may be used to discharge the condensed washing liquid. The discharge port 131-3 may be located at or near the bottom of the condensing chamber 131-1. The discharge port 131-3 may be connected to the condensate inlet 129-9.

In some embodiments, a solid residue (e.g., a solid residue from the solid residue discharge port 121-6 or 122-6, etc.) may be fed into the mixing chamber 129-2 from the solid feed port 129-1. A sugar-including solution (e.g., a sugar-including solution from the sugar solution discharge port 121-5 or 122-5, etc.) may be introduced into the mixing chamber 129-2 from the sugar solution feed port 129-12. The solid component in the mixture may be retained by the discharge device 129-10 and/or the filter device 129-3. The liquid component (e.g., sugar-including solution, etc.) in the mixture may pass through the filter device 129-3 by gravity and into the washing liquid chamber 130-1 via the connection device 129-4. When the first heating device is heating, the washing liquid (e.g., water, or the like) is heated to become steam, and the washing liquid steam (e.g., water steam) may be discharged from the steam outlet 130-5, and brought into the condensing chamber 131-1 by the feed port 131-2. The washing liquid steam (e.g., water steam, or the like) may transfer heat to the heat transfer medium (e.g., circulating condensed water, or the like), thereby becoming a liquid (e.g., water, or the like). The condensed washing liquid may be discharged from the discharge port 131-3 and brought into the mixing chamber 129-2 from the condensate inlet 129-9, and to be in contact with the mixture, thereby dissolving some components in the mixture (e.g., sugars generated after the biological object degradation reaction, etc.) in the washing liquid (e.g., water, or the like). The washing liquid (e.g., an aqueous solution including sugars) in which the extracted components are dissolved may pass through the filter device 129-3, and enter the washing liquid chamber 130-1 via the connection device 129-4, thus circulating repeatedly. When the components are extracted, the washing liquid (e.g., an aqueous solution including sugars) in which the extracted components are dissolved may be discharged from the washing liquid outlet 130-6 for further treatment (e.g., into a dilute sugar storage tank or performing a hydrogenation to prepare sugar alcohol); the solid residue may be sent to the mixing chamber 129-2 by the discharge device 129-11 from the discharge port 129-11 for further processing (e.g., the separation of lignin from catalysts or the recovery of catalysts).

In some embodiments, the first chamber 129 may further include a second heating device. The second heating device may be used to heat and dry the mixture, and may also be used to accelerate the dissolution rate of the extracted components in the washing liquid and to improve the solubility of the extracted components in the washing liquid. The second heating device may include one or more heating substance inlets 129-6, one or more heating jackets 129-7, and one or more condensate outlets 129-8. The heating substance inlet 129-6 may be used to feed the heating substance. The heating substance may be steam, hot water, hot oil, or the like. The condensate outlet 129-8 may be used to discharge the cooled heating substance. The heating jacket 129-7 may be used to transfer heat of the heating substance to the mixture and/or the washing liquid through the mixing chamber 129-2, so as to heat and dry the mixture and speed up the dissolution rate of the extracted components in the washing liquid and improve the solubility of the extracted components in the washing liquid. In some embodiments, the heating jacket 129-7 may be located outside of the mixing chamber 129-2. In some embodiments, the heating substance that is introduced into the heating jacket 129-7 may be replaced by a heating structure placed inside the heating jacket 129-7, for example, a resistance wire. In some embodiments, the heating structure (e.g., the resistance wire) may be directly placed outside the mixing chamber 129-2 without a heating jacket.

In some embodiments, the heating substance may be introduced into the heating jacket 129-7 from the heating substance inlet 129-6, and then be discharged from the condensate outlet 129-8 by cooling.

In some embodiments, the first chamber 129 may further include one or more sampling devices 129-5. The sampling device 129-5 may be used to sample and detect the washing liquid flowing through the connection device 129-4 to determine whether the extracted components in the mixture have been completely extracted. The detection method may be qualitative detection or quantitative detection. For example, when the detection result indicates that the extracted washing liquid does not include the extracted components (e.g., the sugar generated after the biological object degradation reaction) or includes a small amount (e.g., a mass fraction of 1% or less) of the extracted components (e.g., the sugar generated after the biological object degradation reaction), the extraction may be terminated. In some embodiments, the contact time of the mixture with the washing liquid may be extended to dissolve more extracted components in the washing liquid, thereby achieving a better extraction effect. The washing liquid may stay in the mixing chamber 129-2 for a period of time. The sampling device 129-5 may also be used to trap the washing liquid. In some embodiments, the sampling device that implements the sampling function and the sampling device that implements the interception function may be different devices or the same device. For example, the sampling device 129-5 may be a three-way device. The sampling and interception functions may be implemented by controlling the direction of the opening of the three-way device.

The above description of the washing filter is merely a specific example and should not be considered as the only feasible embodiment. Obviously, it will be apparent to those skilled in the art that upon understanding the basic principles of the washing filter, various modifications and changes in the form and details of the structure and implementation of the washing filter may be made without departing from this principle. However, these modifications and changes are still within the scope of the above description. For example, in some embodiments, the second chamber 130 may not include the washing liquid outlet 130-6. In this case, the connection device 129-4 may be detachably connected to the washing liquid chamber 130-1. When it is necessary to remove the washing liquid, the connection device 129-4 may be separated from the washing liquid chamber 130-1, and then the washing liquid is poured out. In some embodiments, the washing filter may further include a gas pressure adjusting device. The gas pressure adjusting device may be used to change the air pressure within the mixing chamber 129-2 and/or the washing liquid chamber 130-1 to utilize atmospheric pressure to increase or decrease the rate of the solid-liquid separation (flow of filtrate per unit time). Such variants are covered by the present disclosure.

Figure 13:
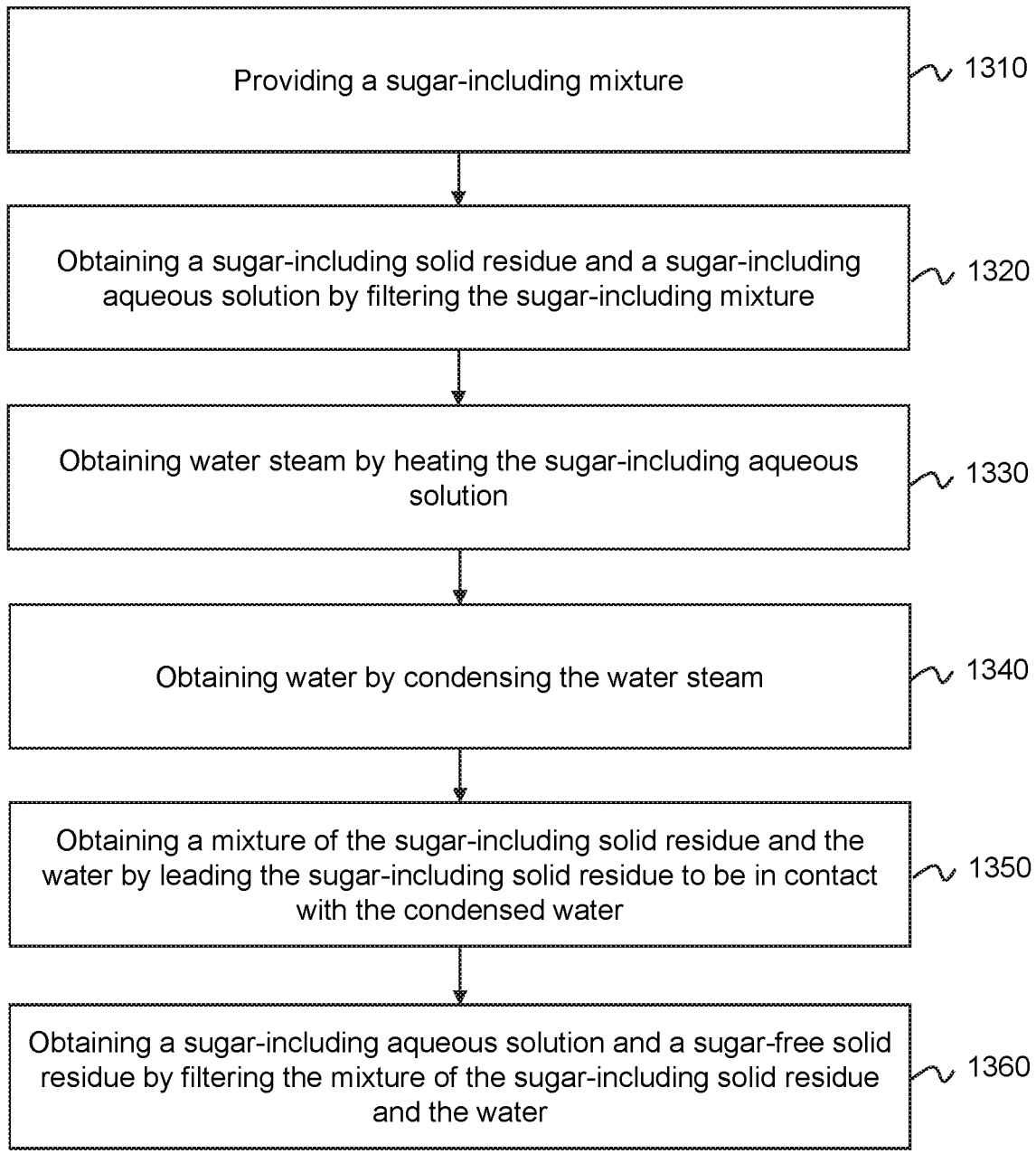
FIG. 13 is a flowchart illustrating an exemplary process for collecting a sugar solution in a residue according to some embodiments of the present disclosure.

According to some embodiments of the present disclosure, FIG. 13 is a flowchart illustrating an exemplary process for collecting a sugar solution in a residue. After the biological object degradation reaction is completed, the solid residue after the reaction still includes sugars. Therefore, the sugar in the solid residue may be extracted. The concentration of the sugar solution is decreased, if a large amount of water is added to extract the sugar in the solid residue, and subsequent extraction of the sugar in the aqueous solution including sugars requires evaporation of a large amount of water, resulting in an increase in energy consumption, which is not conducive to the industrialization of systems and methods in the present disclosure. Therefore, the aqueous solution including sugars after the biological object degradation reaction may be used as a washing liquid so that the most of the sugars in the solid residue may be extracted without reducing the concentration of sugars, reducing energy consumption, which is more conducive to the industrialization of the system and method in the present disclosure.

In 1310, a sugar-including mixture is provided. In some embodiments, the sugar-including mixture may be a mixture of a solid residue and a sugar-including solution. The solid residue may be from the solid residue discharge port 121-6 or 122-6. The sugar-including solution may be from the sugar solution discharge port 121-5 or 122-5, the washing liquid outlet 130-6, the sugar storage tank, or the like.

In 1320, the sugar-including mixture may be filtered, and a sugar-including solid residue and a sugar-including aqueous solution may be obtained. The conditions of filtration may be an atmospheric filtration, a pressure filtration, a vacuum filtration, etc.

In 1330, the sugar-including aqueous solution is heated to obtain water steam. In some embodiments, the heating temperature may be from 90° C. to 150° C., 100° C. to 120° C., or the like.

In 1340, the water steam may be condensed to obtain water.

In 1350, the sugar-including solid residue may be in contact with the condensed water to obtain a mixture of the solid residue and water. During the contact, the sugar in the solid residue dissolves in the water to form a sugar-including aqueous solution. In some embodiments, the mixture of the solid residue and water may be heated to increase the dissolution rate of the sugar in water and the solubility of the sugar in water, so that more sugars may be dissolved in water and the extraction efficiency may be improved.

In 1360, the mixture of the sugar-including solid residue and water is filtered to obtain a sugar-including aqueous solution and a sugar-free solid residue. Then, operation 1330 is performed, thus circulating repeatedly. In some embodiments, a process in which the filtration and the extraction are performed simultaneously may be used. For example, after the water steam is condensed into water, and the water is led to be in contact with the solid residue, and then introduced into the washing liquid chamber 130-1 through the filter device 129-3. In some embodiments, a process in which the extraction is before the filtration may be performed. For example, after the water steam is condensed into water, the water is first in contact with the solid residue for a period of time (e.g., 0.5 hour, etc.), and then flows into the washing liquid chamber 130-1 through the filter device 129-3.

In some embodiments, a process of sampling detection may be added during the process of extracting sugars. The method of detection may be qualitative detection or quantitative detection. For example, when the test result indicates that the sampled aqueous solution does not include sugars or includes a small amount of sugars (e.g., the mass fraction is less than or equal to 1%, etc.), the extraction is terminated.

Figure 14:
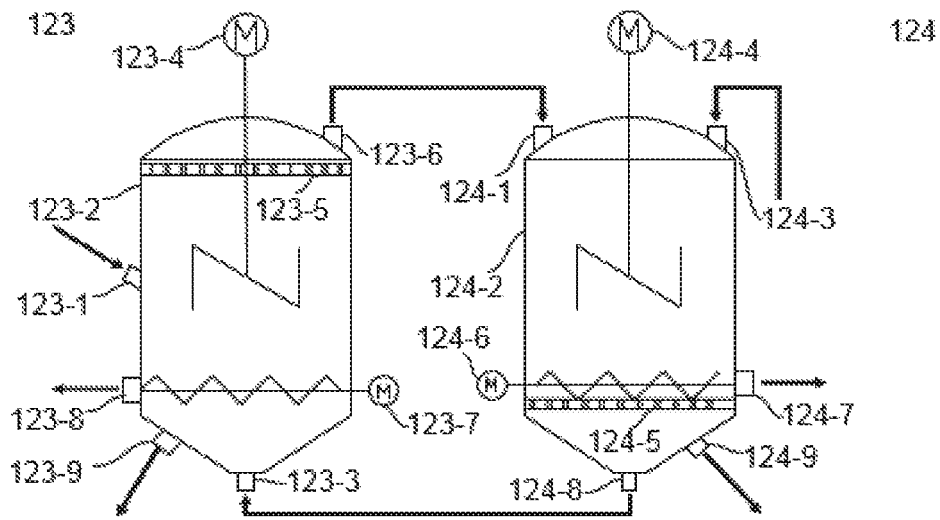
FIG. 14 is a shematic diagram illustrating an exemplary first separator and an exemplary second separator according to some embodiments of the present disclosure.

According to some embodiments of the present disclosure, FIG. 14 is a shematic diagram illustrating an exemplary first separator and an exemplary second separator. In some embodiments, the first separator 123 and the second separator 124 may be used to separate components having different particle sizes in the solid mixture by combining hydraulic circulation and filtration. The first separator 123 and/or the second separator 124 may rotate the washing water around the central axis of the separator by stirring. The components of the larger particles are gravitationally settled down, and the components of the smaller particles are floated up to achieve separation of components with different particle sizes. For example, the solid residue after the biological object degradation reaction incudes lignin particles with a large particle size, fine straw slag including hemicellulose and cellulose with a small particle size, straw slag, and catalyst particles with a small particle size; the second separator 124 may separate the lignin particles with a large particle size, fine straw slag including hemicellulose and cellulose with a small particle size, straw slag, and catalyst particles with a small particle size from the solid residue. The first separator 123 and the second separator 124 may be used as a combination.

In some embodiments, the first separator 123 may include one or more feed ports 123-1, a separation chamber 123-2, one or more water inlets 123-3, one or more stirring devices 123-4, one or more filter devices 123-5, one or more first discharge ports 123-6, one or more discharge devices 123-7, and one or more second discharge ports 123-8.

The feed port 123-1 may be used for feeding solid mixtures including components with different particle sizes (e.g., the solid residue after the biological object degradation reaction including larger lignin particles and catalyst particles with a smaller particle size). In some embodiments, the feed port 123-1 may be used for feeding the solid residue discharged from the washing filter 129. In some embodiments, the feed port 123-1 may be connected with the outlet 129-11 of the washing filter 129. In some embodiments, the feed port 123-1 may be located at or near the top, and/or on the side wall of the separation chamber 123-2.

In some embodiments, the separation chamber 123-2 may be used to accommodate the solid mixture to be separated and the washing water. In some embodiments, the lower portion of the separation chamber 123-2 may be conical.

In some embodiments, the water inlet 123-3 may be used to feed washing water. In some embodiments, the water inlet 123-3 may be located at or near the top or bottom, and/or on the side wall of the separation chamber 123-2. In some embodiments, the water inlet 123-3 may be connected to the water outlet 124-8 of the second separator 124 so that the washing water may be discharged from the water outlet of the second separator 124, and then may be introduced into the first separator via the water inlet 123-3 to realize the recycling of the washing water. In some embodiments, the water in the washing water storage tank may be introduced into the first separator via the water inlet 123-3. It is also possible to feed water from other water sources (e.g., tap water, cooling water, steam condensate, etc.) from the water inlet 123-3 into the first separator.

In some embodiments, the stirring device 123-4 may be used to stir the solid mixture to be separated and washing water, so that the solid mixture to be separated may be uniformly dispersed in the washing water, and the washing water is rotated around the central axis of the separation chamber 123-2. The components with a large particle size in the mixture are gravitationally settled down, and the components with a small particle size float up. In some embodiments, the stirring device 123-4 may be a magnetic stirring device, a mechanical stirring device, an ultrasonic stirring device, or the like, or any combination thereof. In some embodiments, the magnetic stirring device may include a magnetic stirrer, a stirrer, or the like. In some embodiments, the mechanical stirring device may include a motor, a stirring rod, or the like. The shape of the stirring rod may be a slurry type, a toothed type, a turbine type, an anchor type, a frame type, a ribbon type, a screw type, a Bruma gold type, or the like. In some embodiments, the ultrasonic stirring device may include an ultrasonic stirring system, an ultrasonic driving system, or the like. The ultrasonic stirring system may include a stirring rod. During the stirring process, the stirring rod is in contact with the solid-liquid mixture, and the ultrasonic energy is transmitted to the solid-liquid mixture to agitate the solid-liquid mixture. The ultrasonic stirring system may also include a stirring tank. During the stirring process, the liquid is poured into the stirring tank, and the container (e.g., the first separator 123) including the solid-liquid mixture to be stirred is led to be in contact with the liquid, and the ultrasonic wave propagates in the liquid to vibrate the solid-liquid mixture together with the liquid, thus stirring the solid-liquid mixture.

In some embodiments, the filter device 123-5 may be used to trap large particle components (e.g., lignin particles in solid residues after the biological object degradation reaction, etc.) in the solid mixture to be separated, allowing small particle components (e.g., catalyst particles in the solid residue after the biological object degradation reaction, etc.) and washing water to pass through. In some embodiments, the filter device 123-5 may be located inside the separation chamber 123-2. The filter device 123-5 may be located at or near the top of the separation chamber 123-2. The filter device 123-5 may be a strainer, a mesh screen, a filter paper, a filter cloth, a filter cotton, or the like, or any combination thereof. The filtering device may include a certain number of pores. The pore size allows for the passage of water or a solution and prevents the passage of solid particles larger than the pore size. In some embodiments, filter devices with different pore sizes may be selected according to the size of the catalyst and/or the biological object. For example, in order to allow the passage of catalyst particles in the solid residue after the biological object degradation reaction and washing water, and prevent the passage of the lignin particles, the pore size of the filter device 123-5 may be in a range of 50 meshes to 100 meshes.

In some embodiments, the first discharge port 123-6 may be used for the discharge of small particle components (e.g., components including the catalyst, etc.) and washing water. In some embodiments, the first discharge port 123-6 may be located at or near the top of the separation chamber 123-2. In some embodiments, the first discharge port 123-6 may be connected to the feed port 124-1 of the second separator 124.

In some embodiments, the discharge device 123-7 may be used to trap large particle components (e.g., components including lignin particles, etc.), or to discharge large particle components (e.g., components including lignin particles, etc.) out of the separation chamber 123-2. In some embodiments, the discharge device 123-7 may be connected to the second discharge port 123-8. In some embodiments, the discharge device 123-7 may be similar to the dispensing device described in FIG. 7-B.

In some embodiments, the large particle components (e.g., a component including lignin particles, etc.) may be discharged from the second discharge port 123-8 for further processing (e.g., extraction of lignin, or the like). In some embodiments, the second discharge port 123-8 may be located on the side wall of the separation chamber 123-2, or may be located on the discharge device 123-7.

In some embodiments, the feed port 123-1, the first discharge port 123-6, and the second discharge port 123-8 may include one or more sealing devices. The sealing device may be configured to seal the feed port 123-1, the first discharge port 123-6, and the second discharge port 123-8, thereby making the first separator 123 become a sealed container, and/or controlling the entry and discharge of the substance. In some embodiments, the sealing device may be a valve, a sealing cover, a piston, a hydraulic seal, a pneumatic seal, or the like, or any combination thereof.

In some embodiments, the solid mixture to be separated (e.g., the solid residue after the biological object degradation reaction) may enter the separation chamber 123-2 from the feed port 123-1. The washing water may enter the separation chamber 123-2 from the water inlet 123-3 to be in contact with the solid mixture to be separated (e.g., the solid residue after the biological object degradation reaction). By the stirring device 123-4, the solid mixture to be separated (e.g., the solid residue after the biological object degradation reaction) may be sufficiently in contact with the washing water and the solid mixture to be separated (e.g., the solid residue after the biological object degradation reaction) may be uniformly dispersed in the washing water. The washing water may be rotated around the central axis of the separation chamber 123-2 by the stirring device 123-4. The large particle component (e.g., a component including lignin particles) may be intercepted by a separation net with a certain number of meshes, and small particle components (e.g., a component including catalyst particles) may be separated by the separation net. The small particle component (e.g., the component including the catalyst particles) and the washing water may be discharged from the first discharge port 123-6 through the filter device 123-5 for further processing (e.g., entering the second separator 124 for filtration). The large particle component (e.g., the component including the lignin particles) may be sent out of the separation chamber 123-2 from the discharge device 123-7 via the second discharge port 123-8 for further processing (e.g., extracting lignin).

In some embodiments, the first separator 123 may further include one or more washing water reflux outlets 123-9. The outlets may be used for the discharge of washing water. In some embodiments, the washing water reflux outlets 123-9 may be located at or near the bottom of the separation chamber 123-2, and/or on the side walls of the separation chamber 123-2.

The above description of the structure of the first separator is merely a specific example and should not be considered as the only feasible implementation. Obviously, for those skilled in the art, after understanding the basic principle of the first separator, various modifications and variations in the form and details of the structure and implementation of the first separator may be made without departing from this principle. However, these modifications and variations are still within the scope of the above description. For example, in some embodiments, the separation chamber 123-2 may be rotatable for the purpose of stirring the solid mixture to be separated and the washing water, and separating the large particle component from the small particle component. During the separation process, the separation chamber 123-2 may be rotated at a certain speed to achieve the purpose of stirring the solid mixture to be separated and the washing water and to achieve separation of the large particle component from the small particle component. In some embodiments, the first separator 123 may also be placed on a device (e.g., a centrifuge) that may be rotated at a certain speed. During the separation process, the separation chamber 123-2 may be rotated at a certain speed with a rotatable device (e.g., a centrifuge), thereby achieving the purpose of stirring the solid mixture to be separated and the washing water, and achieving separation of the large particle component from the small particle component. Such variations are within the protection scope of the present disclosure.

In some embodiments, the second separator 124 may be configured to separate the small particle component (e.g., the component including catalyst particles), discharged from the first discharge port 123-6 of the first separator 123, and washing water.

In some embodiments, the second sepatator 124 may include one or more feed ports 124-1, a separation chamber 124-2, one or more stirring devices 124-4, one or more filtering devices 124-5, one or more discharge devices 124-6, one or more discharge ports 124-7, and one or more water outlets 124-8.

In some embodiments, the feed port 124-1 may be used for the feed of a mixture of the small particle component and the washing water. In some embodiments, the feed port 124-1 may be located at or near the top of the separation chamber 124-2, and/or on the side walls of the separation chamber 124-2. In some embodiments, the feed port 124-1 may be connected to the first discharge port 123-6 of the first separator 123. After being discharged from the first discharge port 123-6 of the first separator 123, the materials may enter the second separator 124 through the feed port 124-1.

In some embodiments, the separation chamber 124-2 may be configured to accommodate the mixture of the small particle component and the washing water.

In some embodiments, the stirring device 124-4 may be configured to stir the mixture of the small particle component and the washing water so that the small particle component may be uniformly dispersed in the washing water. In some embodiments, the stirring device 124-4 may be a magnetic stirring device, a mechanical stirring device, an ultrasonic stirring device, or the like, or any combination thereof. In some embodiments, the magnetic stirring device may include a magnetic stirrer, a stir bar, or the like. In some embodiments, the mechanical stirring device may include a motor, a stirring rod, or the like. The stirring rod may be in a slurry type, a toothed type, a turbine type, an anchor type, a frame type, a ribbon type, a screw type, a Bruma gold type, or the like. In some embodiments, the ultrasonic stirring device may include an ultrasonic stirring system, an ultrasonic driving system, or the like. The ultrasonic stirring system may include a stirring rod. During the stirring process, the stirring rod may be in contact with the solid-liquid mixture, and the ultrasonic energy may be transmitted to the solid-liquid mixture to stir the solid-liquid mixture. The ultrasonic stirring system may also include a stirring tank. During the stirring process, the liquid is poured into the stirring tank. A container including the solid-liquid mixture to be stirred (e.g., the second separator 124) may be in contact with the liquid, and the ultrasonic wave may propagate in the liquid to vibrate the solid-liquid mixture together with the liquid, thus stirring the solid-liquid mixture.

In some embodiments, the filter device 124-5 may be configured to retain the small particle component and filter the washing water. In some embodiments, the filter device 124-5 may be located inside the separation chamber 124-2. The filter device 124-5 may be located in the downstream of a flow direction of the discharge device 124-6. The filter device 124-5 may be a strainer, a mesh screen, a filter paper, a filter cloth, a filter cotton, or the like, or any combination thereof. The filtering device may have a certain pore size. The pore size may allow water or a solution to pass through and prevents solid particles larger than the pore size from passing through. In some embodiments, filtering devices with different pore sizes may be selected according to the particle size of the catalyst and/or the biological object.

In some embodiments, the discharge device 124-6 may be configured to discharge the small particle component out of the separation chamber 124-2. In some embodiments, the discharge device 124-6 may be located near the discharge port 124-7. In some embodiments, the discharge device 124-6 may be the dispensing device described in FIG. 7-B.

In some embodiments, the small particle component may be discharged by the discharge port 124-7 for further processing (e.g., recycling the catalyst). In some embodiments, the discharge port 124-7 may be located on the side walls of the separation chamber 124-2, or on the discharge device 124-6.

In some embodiments, the filtrate may be discharged from the water outlet 124-8, and the discharged filtrate may be stored in a washing water storage tank. In some embodiments, the discharged filtrate may also be recycled to the separation chamber 123-2 by the water inlet 123-3 of the first separator 123. In some embodiments, the water outlet 124-8 may be located at or near the bottom of the separation chamber 124-2. In some embodiments, the water outlet 124-8 may be connected to the water inlet 123-3 of the first separator 123.

In some embodiments, a mixture of the small particle component from the first separator (e.g., the component including catalyst particles and fine straw residue) and washing water may enter the separation chamber 124-2 from the feed port 124-1. Under the operation of the stirring device 124-4, the small particle component may be uniformly dispersed in the washing water. The washing water may be discharged from the water outlet 124-8 through the filter device 124-5 for further processing (e.g., entering the washing water storage tank or entering the separation chamber 123-2 from the water inlet 123-3 of the first separator 123). The small particle component (e.g., the component including the catalyst particles) may be retained by the filtration device 124-5, and then sent out of the separation chamber 124-2 by the discharge device 124-6 and discharge port 124-7 for further processing (e.g., recycling the catalyst).

In some embodiments, the second separator 124 may further include one or more water inlets 124-3. When the washing water is too little in the separation chamber 124-2, the washing water may be introduced from the water inlet 124-3; or when the water inlet 123-3 of the first separator 123 is connected to the water outlet 124-8 of the second separator 124, the water inlet 124-3 may be served as a water inlet in the separation system including a second separator for introducing the washing water required for the entire system. The water inlet 124-3 may be located at or near the top, and at or near the bottom of the separation chamber 124-2, and/or on the side walls of the separation chamber 124-2.

In some embodiments, the second separator 124 may further include one or more washing water reflux outlets 124-9. When the water inlet 123-3 of the first separator 123 is connected to the water outlet 124-8 of the second separator 124, the washing water reflux outlet 124-9 may be configured to discharge the washing water into the washing water storage tank. In some embodiments, the washing water reflux outlet 124-9 may be located at or near the bottom of the separation chamber 124-2, and/or on side walls of the separation chamber 124-2.

In some embodiments, the feed port 124-1, the discharge port 124-7, the water outlet 124-8, the water inlet 124-3, and the washing water reflux outlet 124-9 may include one or more sealing devices. The sealing device may be used to seal the feed port 124-1, the discharge port 124-7, the water outlet 124-8, the water inlet 124-3, the washing water reflux outlet 124-9, thereby making the second separator 124 become a sealed container, and the sealing device may also be configured to control the entry and discharge of substances. In some embodiments, the sealing device may be a valve, a sealing cover, a piston, a hydraulic seal, a pneumatic seal, or the like, or any combination thereof.

In some embodiments, the first separator 123 and the second separator 124 may be used as a system to separate solid mixtures including components of different particle sizes. The first separator 123 and the second separator 124 may also be used with other devices to separate the solid mixtures including components of different particle sizes, respectively. For example, the second separator 124 may be used with a cyclone filter or a centrifuge to separate the solid mixtures including components of different particle sizes.

The above description of the structure of the second separator is merely a specific example and should not be considered as the only feasible embodiment. Obviously, for those skilled in the art, after understanding the basic principle of the second separator, various modifications and variations in the form and details of the structure and implementation of the second separator may be made without departing from this principle. However, these modifications and variations are still within the scope of the above description. For example, in some embodiments, the second separator 124 may further include a air pressure adjusting device. The air pressure adjustment device may be configured to vary the air pressure within the separation chamber 124-2, thereby utilizing atmospheric pressure to increase or decrease the rate of solid-liquid separation. In some embodiments, the second separator 124 may not include the stirring device 124-4. Such variations are within the protection scope of the present disclosure.

Figure 15:
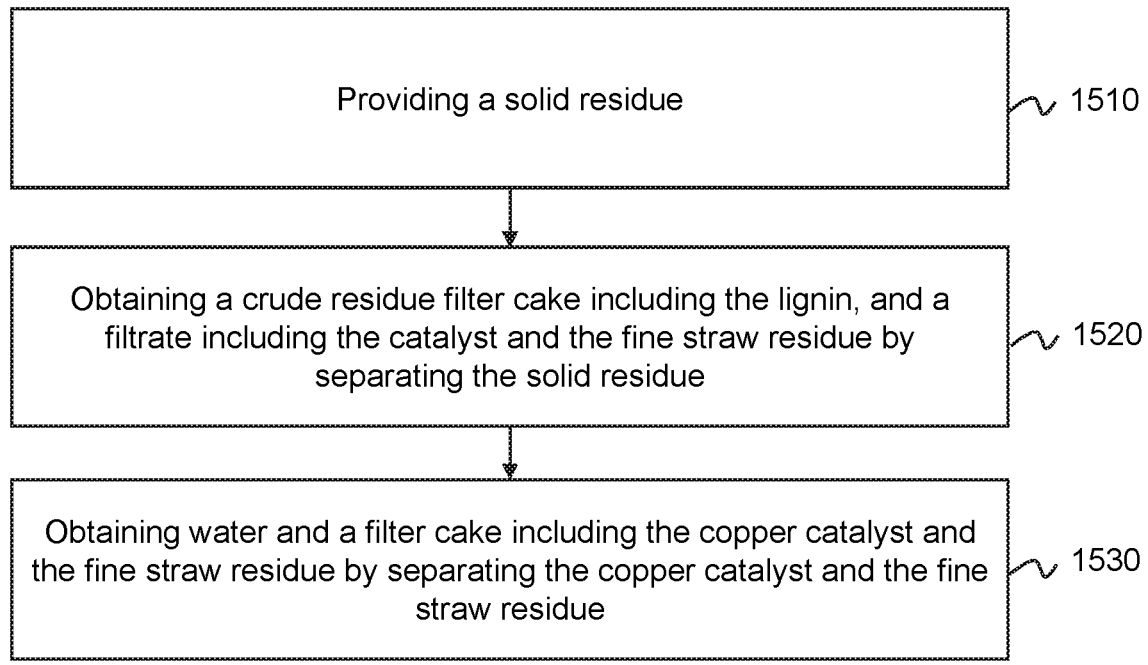
FIG. 15 is a flowchart illustrating an exemplary process for separating lignin and a copper catalyst according to some embodiments of the present disclosure.

FIG. 15 is a flowchart illustrating an exemplary process for separating lignin and a copper catalyst according to some embodiments of the present disclosure. The solid residue obtained after the biological object degradation reaction may include a copper catalyst, fine straw residue (including cellulose and hemicellulose), and lignin. The copper catalyst may have relatively small particles and the lignin may have relatively large particles. The separation of the lignin and the copper catalyst may be carried out by using the different particle sizes of the copper catalyst and the lignin.

In 1510, a solid residue may be provided. In some embodiments, the solid residue may be the solid residue after the biological object degradation reaction, and include the copper catalyst with relatively smaller particles, fine straw residue (including hemicellulose and cellulose), and the lignin with relatively large particles.

In 1520, the solid residue may be separated to obtain a crude residue filter cake including the lignin, and a filtrate including the catalyst and the fine straw residue. In some embodiments, the solid residue may be separated using the first separator 123 described in FIG. 14. In some embodiments, other separation devices may be configured to separate the solid residues, such as a cyclone filter, a centrifuge.

In 1530, the copper catalyst and the fine straw residue may be separated to obtain a filter cake including the copper catalyst and the fine straw residue. In some embodiments, the copper catalyst and the fine straw residue may be filtered using the second separator 124 described in FIG. 14. In some embodiments, the copper catalyst including the copper catalyst and the fine straw residue may be processed by the operation of copper catalyst recovery. The specific processing method for recycling the copper catalyst may be referred to the corresponding description of FIG. 16.

It should be noted that the above description of the process for separating the lignin and the copper catalyst is merely exemplary and should not be considered as the only feasible embodiment. Obviously, it will be apparent to those skilled in the art that after understanding the basic principles of the separator, various modifications and variations in the form and details of the implementation of the separation process may be made without departing from this principle. However, these modifications and variations are still within the scope of the above description. For example, in some embodiments, the separation of the copper catalyst and the fine straw residue may be separated continually after 1530. The copper catalyst and the fine straw slag may be recycled respectively via centrifugal separation or other means utilizing the difference in density between the copper catalyst and the fine straw residue. In some embodiments, the fine straw residue may be present in the filtrate after centrifugation. The copper catalyst is deposited on the bottom of the separated filtrate.

Figure 16:
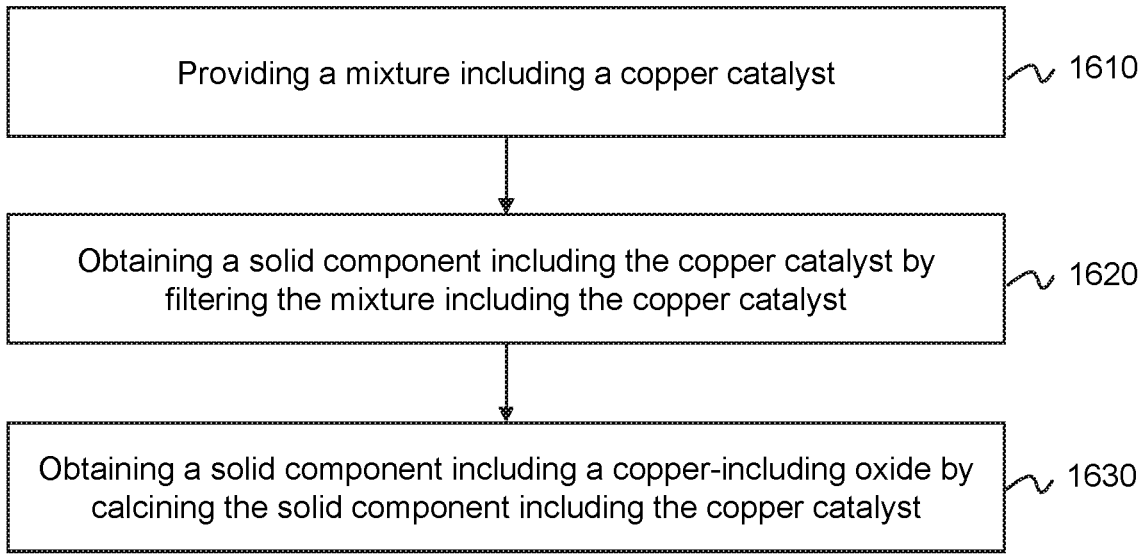
FIG. 16 is a flowchart illustrating an exemplary process for recycling a copper catalyst according to some embodiments of the present disclosure.

FIG. 16 is a flowchart illustrating an exemplary process for recycling the copper catalyst according to some embodiments of the present disclosure. In order to reduce the cost of the biological object degradation process, the copper catalyst in the solid residue after the biological object degradation reaction may be recycled. The residue after the biological object degradation reaction may include the copper catalyst, undegraded cellulose, undegraded hemicellulose, lignin, water, or the like. Cellulose, hemicellulose, and lignin mainly include three elements: C, H, and O. If the residue after the biological object degradation reaction is calcined, the cellulose, hemicellulose, and lignin may be changed into $H_2O$ and $CO_2$, and the copper catalyst may be turned into a copper-including oxide, thereby realizing the recycling of the copper catalyst.

In some embodiments, the calcined solid may be directly used as a catalyst for the subsequent biological object degradation reaction. In some embodiments, copper may be prepared by using a calcined copper-including oxide solid, and then the obtained copper is used as a catalyst in the biological object degradation reaction.

In 1610, a mixture including a copper catalyst may be provided. In some embodiments, the mixture including the copper catalyst may be a solid mixture or a solid-liquid mixture. In some embodiments, the solid mixture may include the copper catalyst and biological object solids (e.g., undegraded cellulose, undegraded hemicellulose, lignin). In some embodiments, the solid-liquid mixture may include the copper catalyst, water, and/or biological object solids (e.g., undegraded cellulose, undegraded hemicellulose, lignin, etc.). In some embodiments, the solid-liquid mixture may be a suspension solution. In some embodiments, the mixture including the copper catalyst may come from the inside of the first separator 123 or the second separator 124.

In 1620, the mixture including the copper catalyst may be filtered to obtain a solid component including the copper catalyst. In some embodiments, before being filtered, the mixture including the copper catalyst may be subjected to other processing such as agitation, extrusion, washing, or the like. In some embodiments, the filtration of the mixture including the copper catalyst may be carried out by the first separator 123 and/or the second separator 124, or other solid-liquid separation devices (e.g., a cyclone filter, a centrifuge, etc.). In some embodiments, the filtration of the mixture including the copper catalyst may result in a solid component including only the copper catalyst, or a solid mixture including the copper catalyst and one or more other substances (e.g., cellulose, hemicellulose, lignin). In some embodiments, the filtration of the mixture including the copper catalyst may be a solid-liquid separation of the solid component including the copper catalyst from water, or a separation of a component including the copper catalyst with small particles from the component including large particles (e.g., lignin), or a combination of these two processes.

In 1630, the solid component including the copper catalyst may be calcined to obtain a solid component including a copper-including oxide.

In some embodiments, the solid component including the copper catalyst may be processed before being calcined, so that the solid component including the copper catalyst may be sufficiently in contact with oxygen. The processing of the solid component including the copper catalyst may be either a physical processing or a chemical processing. The physical processing may include extrusion, pulverization, sieving, grinding, or the like, or any combination thereof. The chemical processing may include pickling, caustic washing, or the like, or any combination thereof.

In some embodiments, the calcination temperature may be 300° C. to 2000° C., 300° C. to 1500° C., 400° C. to 800° C., 400° C. to 600° C., 500° C., or the like. In some embodiments, the calcination time may be from 0.5 hour to 20 hours, from 0.5 hour to 15 hours, from 1 hour to 5 hours, from 1 hour to 3 hours, or the like. In some embodiments, the calcination may be carried out in an open space. In some embodiments, the calcination may be carried out in a closed container. In some embodiments, the solid component including a copper-including oxide may include copper oxide, cuprous oxide, or the like, or any combination thereof. The solid component including the copper oxide obtained in 1630 may be used again as a catalyst for the biological object degradation reaction. In some embodiments, the solid component including the copper-including oxide may be prepared into copper before the reaction, and then the obtained copper may be used as a catalyst in the biological object degradation reaction. In some embodiments, the solid component including the copper-including oxide may be directly added to the biological object degradation reaction system. Since the reaction system is carried out in a reducing atmosphere, the solid component including the copper-including oxide may be reduced to copper during the degradation reaction, thereby acting as a catalyst.

The above description of the process for recycling the copper catalyst is merely a specific example and should not be considered as the only feasible implementation. Obviously, for those skilled in the art, after understanding the basic principles of recycling copper catalyst, various modifications and variations in the form and details of the recycled copper catalyst step may be performed without departing from this principle. However, these modifications and variations are still within the scope of the above description. For example, in some embodiments, the same operation may be performed repeatedly and one or more operations may be performed cyclically in order to achieve the effect and purpose of the process. For example, in order to make the mixture including the copper catalyst meet the requirements, operation 1620 may be performed repeatedly. In some embodiments, the mixture including the copper catalyst may be directly calcined without operation 1620. Such deformations are within the protection scope of the present disclosure.

FIG. 17 is a flowchart illustrating an exemplary process for extracting lignin according to some embodiments of the present disclosure. Since lignin includes a large amount of phenolic hydroxyl groups, hydrogen ions may be removed under alkaline conditions to generate a water-soluble phenate. The alkali may first react with the lignin, and the lignin is present as a phenolate under the action of a base. The acid is then added to the phenate solution to precipitate the lignin, thereby extracting the lignin. The traditional alkaline method for extracting lignin may use a sodium hydroxide solution. The sodium hydroxide solution is more corrosive and requires a high-level device. At the same time, if the resulting lignin sodium salt is neutralized with an acid such as hydrochloric acid or sulfuric acid, a large amount of sodium salts (such as, sodium chloride or sodium sulfate) is generated, and it is difficult for continue recycling. In some embodiments, the lignin may be extracted with ammonia water to generate lignin ammonium salts; thereafter, an inorganic ammonium salt (e.g., ammonium chloride, ammonium sulfate) may be generated by being processed with an acid, such as hydrochloric acid or sulfuric acid. The inorganic ammonium salt may be used as a fertilizer, which is convenient for recycling, saves cost, and is more conducive to the industrialization of the process. At the same time, the alkalinity of ammonia is weak, and it is less corrosive to the device during the processing.

In 1710, a crude residue filter cake including the lignin may be provided. In some embodiments, the crude residue filter cake including the lignin may be a solid mixture or a solid-liquid mixture. In some embodiments, the solid mixture may include the copper catalyst, undegraded cellulose, undegraded hemicellulose, lignin, or the like. In some embodiments, the solid-liquid mixture may include a mixture of the copper catalyst, undegraded cellulose, undegraded hemicellulose, lignin, and water. In some embodiments, the solid-liquid mixture may be a colloidal solution, or a suspension solution.

In 1720, the crude residue filter cake including the lignin may be filtered to obtain a solid component including the lignin. In some embodiments, the filtration of the crude residue filter cake including the lignin may be carried out by the first separator 123 and/or the second separator 124, or other filter devices (e.g., an acyclone filter, a centrifuge, etc.). In some embodiments, a solid component only including the lignin, or a solid mixture including the lignin and one or more other substances (e.g., the copper catalyst, cellulose, hemicellulose, etc.) may be obtained by filtrating the crude residue filter cake including the lignin. In some embodiments, the filtration of the crude residue filter cake including the lignin may be a solid-liquid separation of a solid component including the lignin from water, a separation of a component including small particles (e.g., the copper catalyst) from the lignin including large particles, or a combination of the two processes.

In 1730, the solid component including the lignin may be in contact with aqueous ammonia to obtain a solution including lignin ammonium salts. In some embodiments, a mass percentage of the aqueous ammonia to process the lignin may be in a range of 5% to 35%, 10% to 30%, 10% to 25%, or the like. In some embodiments, the concentration of the aqueous ammonia to process the lignin may be 5%, 8%, 10%, 15%, 18%, 20%, 25%, or the like. In some embodiments, the time for the aqueous ammonia to process the lignin may be from 0.5 hour to 12 hours, from 1 hour to 8 hours, from 1 hour to 5 hours, or the like. In some embodiments, the temperature at which the aqueous ammonia processes the lignin may be from 100° C. to 190° C., from 110° C. to 180° C., from 120° C. to 170° C., from 150° C. to 170° C., or the like. In some embodiments, the process of processing the lignin with the aqueous ammonia may also be carried out without heating.

In 1740, the solution including the lignin ammonium salt may be in contact with an acid to obtain the lignin. In some embodiments, the acid to be used may be sulfuric acid, hydrochloric acid, nitric acid, $CO_2$ (soluble in water and partially forming the carbonic acid), phosphoric acid, or the like. In some embodiments, the acid concentration for processing the solution including the lignin ammonium salt may be 5% to 30%, 10% to 20%, 10% to 15%, or the like. In some embodiments, after the addition of the acid, the pH of the solution including the lignin ammonium salt may be 1 to 5, 2 to 3, or the like. In some embodiments, the time of the processing of the solution including the lignin ammonium salt with an acid may be from 0.5 hour to 12 hours, or from 1 hour to 8 hours, or from 1 hour to 5 hours. In some embodiments, the temperature at which the solution including the lignin ammonium salt is processed with an acid may be 25° C. to 100° C., 25° C. to 90° C., 40° C. to 90° C., or 80° C. to 90° C. In some embodiments, the process of processing the solution including the lignin ammonium salt with an acid may also be carried out without heating. An ammonium salt may be obtained in 1740 at the same time the lignin is obtained. In some embodiments, the ammonium salt may be ammonium sulfate, ammonium hydrogen sulfate, ammonium chloride, ammonium nitrate, ammonium hydrogencarbonate, ammonium phosphate, ammonium monohydrogen phosphate, ammonium dihydrogen phosphate, or the like, or any combination thereof.

In some embodiments, after 1740, the solution including the lignin processed with the acid may be washed to be neutral with water. The solution including the lignin may be then filtered and dried to obtain the lignin including less impurities. The obtained lignin may be used as a strengthening agent, a binder or an emulsifier.

The above description of the process of extracting lignin is only a specific example and should not be considered as the only feasible embodiment. Obviously, for those skilled in the art, after understanding the basic principles of extracting lignin, various modifications and variations in the form and details of the process and implementation of extracting lignin may be carried out without departing from this principle. However, these modifications and variations are still within the scope of the above description. For example, in some embodiments, the process of extracting lignin may not include operation 1720 and may directly include contacting the crude residue cake including the lignin with ammonia water to generate a lignin ammonia salt. Such variations are within the protection scope of the present disclosure.

Figure 18:
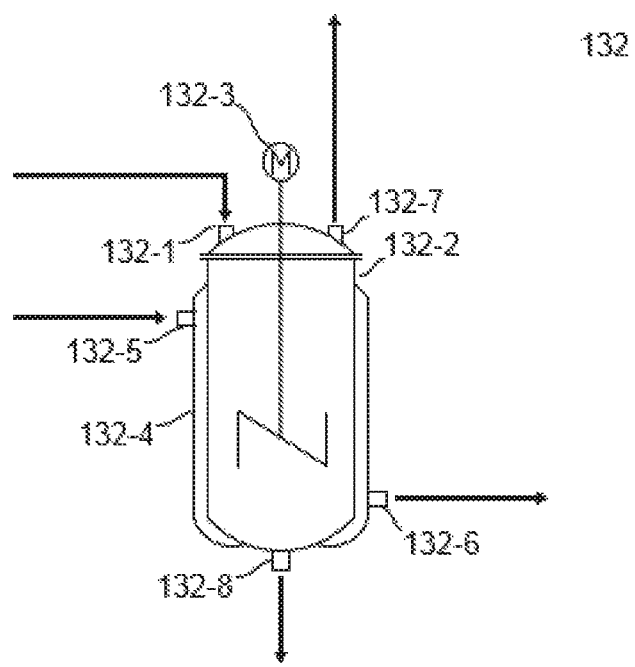
FIG. 18 is a shematic diagram illustrating an exemplary device for concentrating a sugar solution according to some embodiments of the present disclosure.

FIG. 18 is a shematic diagram illustrating an exemplary device for concentrating a sugar solution according to some embodiments of the present disclosure. In some embodiments, the sugar solution concentration device 132 may evaporate the solvent in the stored sugar solution to obtain a sugar solution having an increased sugar concentration. In some embodiments, the sugar solution concentration device 132 may include one or more sugar solution inlets 132-1, a chamber 132-2, one or more stirrers 132-3, a fluid conduit 132-4, one or more fluid inlets 132-5, one or more fluid outlets 132-6, one or more solvent outlets 132-7, and one or more sugar solution outlets 132-8.

In some embodiments, the sugar solution inlet 132-1 may be used for the input of a sugar solution having a lower sugar concentration. The sugar solution having a lower sugar concentration here may be derived from a sugar solution storage tank, or from a sugar solution buffer tank, or the like.

In some embodiments, the sugar solution inlet 132-1 may be located at or near the top of the chamber 132-2. In some embodiments, the sugar solution inlet 132-1 may have a strainer. The function of the strainer is to finely filter the input sugar solution to reduce or avoid the entry of fine straw residue and the catalyst into the chamber 132-2.

The chamber 132-2 may be configured to accommodate the sugar solution. Under heating and stirring, the solvent of water in the sugar solution may be evaporated, and the generated water vapor may escape from the solvent outlet 132-7 and/or the sugar solution inlet 132-3.

The stirrer 132-3 may be configured to stir the sugar solution in the chamber 132-2, which may increase the evaporation rate of the solvent of water. According to the mechanical structure of the stirrer, the stirrer 121-4 may be a propeller stirrer, a turbine stirrer, a paddle stirrer, an anchor stirrer, a ribbon stirrer, a magnetic stirrer, a hinged stirrer, a variable frequency double stirrer, and a side entry stirrer.

The fluid conduit 132-4, the fluid inlet 132-5, and the fluid outlet 132-6 may collectively constitute a heating device for the reactor 132. The heating device herein may be configured to heat the chamber 132-2, thereby heating the sugar solution placed in the chamber 132-2 to evaporate the water vapor. The heating device may utilize a fluid to achieve heating. The fluid herein may include water, water vapor, superheated air, heat transfer oil, or the like. The fluid may enter the fluid conduit from fluid inlet 132-5. The fluid conduit 132-4 may be distributed inside or on the surface of the chamber 132-2 for sufficient heat exchange of the fluid with the sugar solution. After heat exchange, the fluid may exit the fluid conduit 132-4 from the fluid outlet 132-6. It should be noted that the above examples are for convenience of description only and do not limit the present disclosure. Those skilled in the art will appreciate that many variations and modifications may be made in the disclosure of the present disclosure. Although a heating device utilizing the principle of fluid heat exchange is used herein, other types of heating devices may be used in the sugar solution concentration device 132, for example, an electric heating tube, a solar tube, an infrared heating device, or a microwave heating device.

The solvent outlet 132-7 may be used for the discharge of the solvent. The solvent herein refers to a solvent vapor evaporating in the chamber 132-2, such as water vapor. In some embodiments, the solvent outlet 132-7 may have one or more condensers. The function of a condenser is to condense the solvent vapor escaping from the solvent port 132-7, and the liquid solvent obtained after condensation may be recycled and reused.

The sugar solution outlet 132-8 may discharge a sugar solution with a high concentration. The sugar solution with a high concentration herein refers to a sugar solution having an increased sugar concentration obtained after concentration. The sugar solution with a high concentration may be delivered to the sugar solution storage tank. In some embodiments, the concentration of the sugar solution with a high concentration (herein referred to as a mass ratio of the sugar to the sugar solution) may be from 5% to 25%, from 10% to 25%, or from 15% to 25%. In some embodiments, the sugar solution outlet 132-8 may be located at or near the bottom of the chamber 132-2. The sugar solution may be discharged by the action of gravity. In some embodiments, the sugar solution outlet 132-8 may have a strainer. The function of the filter is to filter the solid residue that may be included in the sugar solution to reduce or prevent the solid residue in the sugar solution from flowing into the sugar solution storage tank.

The above description of the sugar solution concentration device is merely a specific example and should not be considered as the only feasible embodiment. Obviously, for those skilled in the art, after understanding the basic principles of the work of sugar solution concentration device, various modifications and variations in the form and details of the specific implementation and steps of the sugar solution concentration device may be carried out without departing from this principle. However, these modifications and variations are still within the scope of the above description. In some embodiments, the sugar solution inlet 132-1 and the sugar solution outlet 132-8 may be configured with one or more sealing devices. The sealing device may seal the sugar solution inlet 132-1 and the sugar solution outlet 132-8 to reduce heat loss and improve energy utilization. The sealing device may be a valve, a sealing cover, a piston, a hydraulic seal, a pneumatic seal, or the like, or any combination thereof. In some embodiments, an outer layer of the fluid conduit 132-4 may have a thermal insulation sleeve, and the thermal insulation sleeve may reduce heat loss and improve heat utilization. Such variations are within the protecton scope of the present disclosure.

Figure 19:
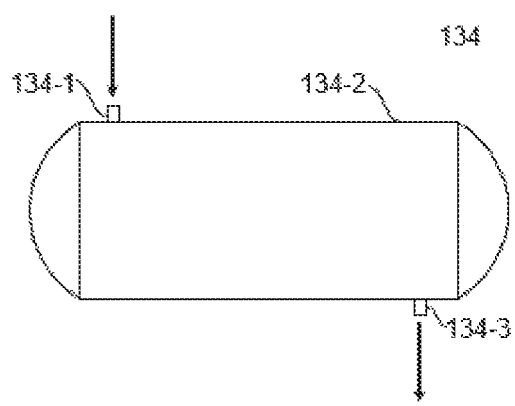
FIG. 19 is a shematic diagram illustrating an exemplary sugar solution storage tank according to some embodiments of the present disclosure.

FIG. 19 is a schematic diagram illustrating an exemplary sugar solution storage tank according to some embodiments of the present disclosure. The sugar solution storage tank 134 may receive and store the sugar solution generated in the biological object degradation device, or receive and store the sugar solution generated in the sugar solution concentration device.

In some embodiments, the sugar solution storage tank 134 may include one or more sugar solution inlets 134-1, a chamber 134-2, and one or more sugar solution outlets 134-3.

In some embodiments, the sugar solution inlet 134-1 may be located at or near the top of the sugar solution chamber 134-2; the sugar solution outlet 134-3 may be located at or near the bottom of the chamber. The sugar solution inlet 134-1 and the sugar solution outlet 134-3 may include one or more sealing devices. The sealing device may be configured to seal the sugar solution inlet 134-1, the sugar solution outlet 134-3, thereby making the sugar solution storage tank 134 become a sealed device, and/or controlling the entry and discharge of the substance. In some embodiments, the sealing device may be a valve, a sealing cover, a piston, a hydraulic seal, a pneumatic seal, or the like, or any combination thereof.

In some embodiments, the sugar solution storage tank may be made of a material resistant to acid, alkali, high temperature, pressure, or abrasion. For example, the sugar solution storage tank may include a metal material (stainless steel, chrome steel, other metals, or alloys), plastic (polyethylene, polypropylene, Teflon, or other engineering plastics), rubber (polyurethane rubber, propylene oxide rubber, or EPDM rubber), inorganic materials (ceramics), inorganic/organic composite materials (various types of glass steel composed of glass fiber reinforced unsaturated polyester, epoxy resin, or phenolic resin matrix).

In some embodiments, the chamber 134-2 may have one or more level gauges. A level gauge may be configured to measure the liquid level of the sugar solution in the chamber 134-2, thereby detecting the liquid level of the chamber 134-2.

The above description of the sugar solution storage tank structure is merely a specific example and should not be considered as the only feasible embodiment. Obviously, for those skilled in the art, after understanding the basic principles of the sugar solution storage tank, various modifications and variations in the form and details of the structure and implementation of the sugar solution storage tank may be carried out without departing from this principle. However, these modifications and variations are still within the scope of the above description. For example, the sugar solution inlet 134-1 and/or the sugar solution outlet 134-3 may be provided with a strainer. The function of the strainer is to filter the sugar solution to remove the solid residue (solid impurities generated in storage, etc.) which may be contained in the sugar solution. These variations or improvements are within the pretection scope of the present disclosure.

FIG. 20-A illustrates a reaction formula of hydrogenation of xylose to xylitol according to some embodiments of the present disclosure. The xylose is hydrogenated to generate the xylitol under a condition of a high temperature, high-pressure, and having a catalyst.

The cracking reaction from sugars to small molecule polyols may usually require relatively intense reaction conditions, such as high temperatures (some sugar alcohols may have a cracking temperature in excess of 200° C.). Under such conditions, the sugar may easily undergo side reactions such as condensation, dehydration, and carbonization, and forms residues such as caramel or coke which are difficult to dissolve. These side reactants may both reduce the conversion and selectivity of the feedstock and cause difficulties in cleaning the interior of the reactor and separating the side reactants from the interior of the reactor. Condensation, dehydration, and charring of sugar alcohols may be relatively difficult to occur compared to sugars. Therefore, before the cleavage, the sugar may be converted into a sugar alcohol by hydrogenation, so as to subsequently cleave the sugar alcohol into a small molecular polyol.

The hydrogenation of the sugar may be carried out in the presence of a catalyst. The catalytic hydrogenation reaction may be a gas-liquid-solid heterogeneous catalytic reaction, which not only has a gas-liquid phase transfer process, but also has a chemical reaction in the liquid phase. The hydrogen absorbed in the gas may first diffuse through the gas film to the gas-liquid interface, and then react with the sugar in the liquid film or the sugar solution, and the aldehyde group and the hydrogen gas may be first adsorbed on the surface of the catalyst to react to form an alcohol having a hydroxyl group. The alcohol may be then desorbed from the surface of the catalyst and leaves the reaction environment.

FIG. 20-B is a schematic diagram illustrating an exemplary hydrogenation reactor according to some embodiments of the present disclosure. The hydrogenation reactor may sufficiently mix the raw materials and hydrogen, which then undergo a hydrogenation reaction to obtain a product after hydrogenation. The raw materials here may be a sugar solution from a sugar solution storage tank, and the hydrogenated product may be a sugar alcohol solution. In some embodiments, the hydrogenation reactor may include one or more sugar solution inlets 136-1, one or more catalyst inlets 136-2, one or more gas inlets 136-3, a chamber 136-4, one or more stirrer 136-5, a fluid conduit 136-6, one or more fluid inlets 136-7, one or more fluid outlets 136-8, one or more sugar alcohol outlets 136-9, and one or more catalyst outlets 136-10.

A sugar solution inlet 136-1 may be used for the input of the sugar solution. In some embodiments, the sugar solution inlet 136-1 may be located at or near the top of the chamber 136-4.

The catalyst inlet 136-2 may be used to input the catalyst. In some embodiments, the catalyst inlet 136-2 may be located at or near the top of the chamber 136-4.

The component including a transition metal may be used as the catalyst for the hydrogenation reaction. In some embodiments, the transition metal may include a non-noble metal, such as Cu or Ni, and a noble metal, such as Ir, Pt, Pd, Ru, Rh, or the like. The component including the transition metal may be a metal element (such as Cu, Ni, Ir, Pt, Pd, Ru, Rh), a metal oxide (such as CuO, $Cu_2O$, $Ni_2O_3$, $PtO_2$, $PdO_2$), metal salts (such as $Ni(HCO_3)_2$, $RuCl_2$, $RuCl_4$), metal carbonyl compounds (such as $Ni(CO)_4$), or other metal compounds (such as metal hydrides, hydroxides, sulfides, borides, nitrides), or the like, or any combination thereof.

The above component including the transition metal may be supported on a carrier. The carrier herein may be a porous material or particles having a large specific surface. In some embodiments, the carrier may include porous carbon/activated carbon, MgO, $Al_2O_3$, $SiO_2$, amorphous silica alumina, zeolite molecular sieves (such as ZSM-5, SBA-15, etc.), $TiO_2$, $ZrO_2$, $WO_3$ or ZnO.

In some embodiments, a Ni—$Al_2O_3$ component is used as a catalyst for hydrogenation reaction. This component may include 10% to 50% by mass of metallic Ni powder and 50% to 90% by mass of $Al_2O_3$. The powder of metal Ni may be used as an active component for catalytic hydrogenation. $Al_2O_3$ may act as a catalyst carrier.

The gas inlet 136-3 may be used to input the gas. The gas here may be hydrogen or a mixed gas including hydrogen, for example, a mixed gas of hydrogen and nitrogen or a mixed gas of hydrogen and carbon dioxide. In some embodiments, the gas inlet may be located at or near the top of the chamber 136-4.

In some embodiments, the sugar solution inlet 136-1, the catalyst inlet 136-2, and the gas inlet 136-3 may be the same part or different parts.

The chamber 136-4 may be configured to accommodate the sugar solution, the catalyst, and the gaseous reactants. The gas in the chamber 136-4 may form an atmosphere. The atmosphere may include hydrogen and have certain pressure. In the case of heating and the presence of the catalyst, the sugar solution may undergo a hydrogenation reaction in the chamber 136-4. The chamber 136-4 may be made of acid-resistant, alkali-resistant, high-temperature resistant, pressure-resistant or wear-resistant materials, for example, metals or alloys (copper, rare earth metals, stainless steel, ductile iron, manganese steel, brass, bronze, white copper, solder, hard aluminum), inorganic materials (ceramics, graphene), polymer materials (organic glass, phenolic resin, ABS resin, polytetrafluoroethylene, polyvinyl chloride), composite materials (color steel plate, glass steel), or the like, or any combination thereof. In order to reduce the wall adsorption property of the catalyst, the inner wall of the chamber 121-3 may be made flatter and smoother, and the inner wall of the chamber 121-3 may be subjected to a certain processing. The processing may be a chemical processing, a physical processing, or a combination of both processings. The chemical processing may be chemical modification or processing of the inner wall, for example, formation of an oxide film, formation of a nitride film, chemical oxidation and surface modification, or the like. The physical processing may include coating, polishing, sanding, milling and extrusion, or the like.

The stirrer 136-5 may be configured to stir and mix the reactants to increase the number of collisions between the reactants, thereby increasing mass transfer efficiency. According to the mechanical structure of the stirrer, the stirrer 136-5 may be a propeller stirrer, a turbine stirrer, a paddle stirrer, an anchor stirrer, a screw belt stirrer, a magnetic stirrer, a folding leaf stirrer, a frequency double-layer stirrer and a side-in stirrer.

The fluid conduit 136-6, the fluid inlet 136-7, and the fluid outlet 136-8 may collectively constitute a heating device for the reactor 136. The heating device herein may be configured to heat the sugar solution, the catalyst, and the gas in the chamber 136-4. The sugar solution may be reacted with hydrogen to obtain a solution including the sugar alcohol under heating. The heating device may utilize a fluid to heat. The fluid herein may include water, water vapor, superheated air, heat transfer oil, or the like. The fluid may enter the fluid conduit from the fluid inlet 136-7. The fluid conduit 136-6 may be distributed within the interior or surface of the chamber 136-4 for fluid exchange with the sugar solution, the catalyst, and the gas. After heat exchange, the fluid may leave the fluid conduit 136-8 from the fluid outlet 136-7.

It should be noted that the above examples are for convenience of description only and do not constitute a limitation on the present disclosure. There are many variations and modifications in the present disclosure. Although a heating device utilizing the principle of fluid heat exchange is used herein, other types of heating devices may be used in the hydrogenation reactor 136, for example, an electric heating tube, a solar tube, an infrared heating device, or microwave heating device.

The sugar alcohol outlet 136-9 may discharge the sugar alcohol solution obtained in the hydrogenation reactor. In some embodiments, the sugar alcohol outlet 136-9 may be located at or near the bottom of the chamber 136-4. The sugar alcohol solution may be discharged from the chamber 136-4 by gravity. In some embodiments, the sugar alcohol outlet 136-9 may be located at or near the top of the chamber 136-4. The sugar alcohol solution may be pumped out of chamber 136-4 by a pressure device. In some embodiments, the sugar alcohol outlet 136-9 may have a strainer (not shown). The strainer may be located in the upstream of a liquid flow direction of the sugar alcohol outlet. The function of the strainer is to filter the catalyst that may be included in the sugar alcohol solution to reduce or avoid the catalyst from being mixed in the solution. When the sugar alcohol outlet 136-9 is located at or near the bottom of the chamber 136-4, and the solution with the solid catalyst flows downward under the force of gravity, the solid catalyst may be blocked by the strainer, and the solution may be discharged through the strainer from the sugar alcohol outlet 136-9. When the sugar alcohol outlet 136-9 is located at or near the top of the chamber 136-4, and the solid catalyst may be pumped together with the sugar alcohol solution to the sugar alcohol outlet 136-9 under the operation of the pressure device, the solid catalyst may be blocked by the strainer, and the solution may be discharged through the strainer from the sugar alcohol outlet 136-9.

The catalyst outlet 136-10 may discharge the catalyst. In some embodiments, the catalyst outlet 136-10 may be located at or near the bottom of the chamber 136-4. In some embodiments, the catalyst outlet 136-10 may discharge the filtered catalyst.

In some embodiments, structures of the sugar alcohol outlet 136-9 and the catalyst outlet 136-10 may be same or different.

The above description of the hydrogenation reactor is merely a specific example and should not be considered as the only feasible embodiment. Obviously, for those skilled in the art, after understanding the basic principles of the operation of the hydrogenation reactor, various modifications and variations in the form and details of the specific embodiment and steps of the hydrogenation reactor may be carried out without departing from this principle. However, these modifications and variations are still within the scope of the above description. In some embodiments, the sugar solution inlet 136-1, the catalyst inlet 136-2, the gas inlet 136-3, the sugar alcohol outlet 136-9, and the catalyst outlet 136-10 may be provided with one or more sealing devices. The sealing devices may be configured to seal the sugar solution inlet 136-1, the catalyst inlet 136-2, the gas inlet 136-3, the sugar alcohol outlet 136-9, and the catalyst outlet 136-10, thereby making the hydrogenation reactor 136 become a sealed container and/or controlling the entry and discharge of the materials. In some embodiments, the sealing device may be a valve, a sealing cover, a piston, a hydraulic seal, a pneumatic seal, or the like, or any combination thereof. In some embodiments, the outer layer of the fluid conduit 136-6 may have a thermal insulation sleeve. The thermal insulation sleeve may reduce heat loss and improve heat utilization. Such variations are within the protection scope of the present disclosure.

Figure 21:
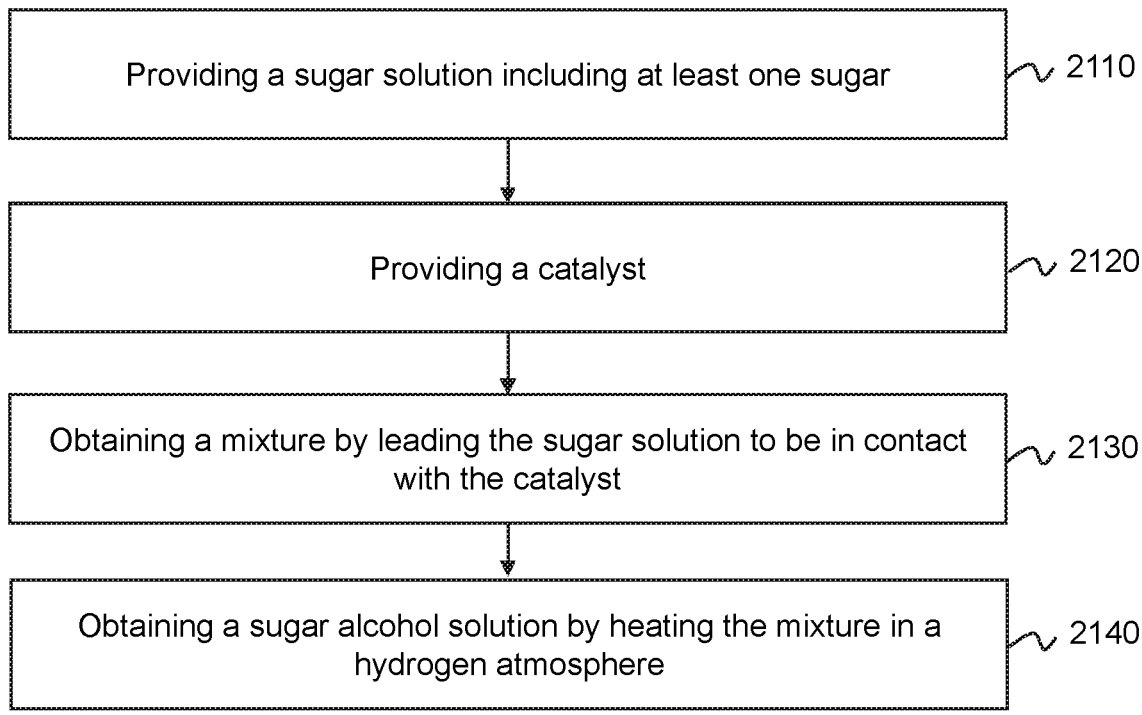
FIG. 21 is a flowchart illustrating an exemplary process for sugar solution hydrogenation according to some embodiments of the present disclosure.

FIG. 21 is a flowchart illustrating an exemplary process for sugar solution hydrogenation according to some embodiments of the present disclosure.

In 2110, a sugar solution including at least one sugar may be provided. The sugar solution here may have a certain concentration. In some embodiments, the sugar solution may include xylose, arabinose, glucose, and a combination thereof.

In 2120, a catalyst may be provided. The catalyst here may be configured to catalyze the hydrogenation of the sugar solution, accelerate the reaction process of the hydrogenation of the sugar solution, and increase the yield of the hydrogenation of the sugar solution. Detailed catalyst components may refer to the description above. The mass percentage of the catalyst to the sugar solution may be from 1% to 30%, from 1% to 20%, from 1% to 10%, from 1% to 5%, or the like. The size of the catalyst particles may be in a range from 20 meshes to 200 meshes, from 80 meshes to 160 meshes, or from 100 meshes to 140 meshes. In some embodiments, the size of the catalyst particles may be 40 meshes, 60 meshes, 80 meshes, 100 meshes, 110 meshes, 120 meshes, 130 meshes, 140 meshes, or 150 meshes, or the like.

In 2130, the sugar solution may be in contact with the catalyst to obtain a mixture. The contact here may be dynamic contact, or static contact. The dynamic contact may refer to uniform mixing of the sugar solution and the catalyst in a manner to obtain a mixture of the catalyst and the sugar solution. In some embodiments, the manner of mixing may be mechanical stirring. In some embodiments, the manner of mixing may be that the hydrogen gas is bubbled through the sugar solution including the solid catalyst. The static contact may refer to fixing a quantity of catalyst particles in the reactor, and making the sugar solution pass through the catalyst at a flow rate. In some embodiments, the sugar solution may pass through the catalyst from the top to the bottom in the axial direction, radially or centrifugally pass through the catalyst, or a combination thereof.

In 2140, the mixture may be heated in a hydrogen atmosphere to obtain the sugar alcohol solution. The hydrogen atmosphere here may have hydrogen pressure.

Under heating and the hydrogen atmosphere, the sugar in the sugar solution may undergo a gas-liquid-solid three-phase reaction to generate a corresponding sugar alcohol under the action of the catalyst. According to the double membrane theory in the gas-liquid-solid three-phase reaction, in the process of the hydrogen gas being transferred to the catalyst surface and adsorbed by the catalyst, it is necessary to overcome the external diffusion resistance when the hydrogen gas is transferred in the liquid. When the gas flow rate is low, the resistance of the hydrogen gas breaking through xylose may be large, and the hydrogenation reaction may not be easy to occur;

When the gas flow rate is increased to a certain value, the external diffusion resistance is eliminated, the reaction may reach a constant value, and the conversion and selectivity of the reaction may gradually become stable.

Increasing the concentration of the sugar solution may increase the rate and conversion rate of the hydrogenation reaction. However, if the concentration of the sugar solution is too large, the selectivity of the sugar alcohol may be reduced. Increasing the reaction temperature may increase the rate and conversion of the hydrogenation reaction. However, if the reaction temperature is too high, a small number of cracking reactions may occur in the sugar alcohol generated in the reaction, thereby reducing the selectivity of the sugar alcohol.

The hydrogenation reaction may be a reaction in which the reactant includes a gaseous substance and the product includes a condensed matter. Therefore, increasing the hydrogen pressure may facilitate the reaction. Increasing the partial hydrogen pressure may increase the rate of the hydrogenation reaction and the conversion rate, while having a greater influence on the selectivity of sugar alcohols. However, the requirement for the hydrogenation reactor may be higher while the partial hydrogen pressure is too large.

Increasing the flow rate of the sugar solution may reduce the back mixing phenomenon in the reactor, thereby increasing the rate of the hydrogenation reaction and the selectivity of the sugar alcohol. However, if the flow rate of the sugar solution is too fast, the contact time of the sugar solution with the catalyst becomes shorter, thereby reducing the conversion rate of the reaction.

In order to understand the influence of different factors on the hydrogenation reaction and determine the appropriate range of reaction conditions, a plurality of experiments were designed. In the experiments, the effects of the gas flow rate, the substrate concentration, the reaction temperature, the hydrogen partial pressure, and the substrate flow rate on the hydrogenation reaction were investigated by a single factor experiment using a xylose solution as raw materials. The experimental results are described in detail in Embodiment Eight to Embodiment Twelve. At the same time, the effects of the substrate concentration, the reaction temperature, the hydrogen partial pressure, and the substrate flow rate on the hydrogenation reaction were investigated by the single factor experiment using arabinose as raw materials. The experimental results are described in detail in Embodiment Thirteen to Embodiment Seventeen.

In the reaction of hydrogenation of the xylose solution, when other experimental conditions were determined, the gas flow rate was increased, and thereby the conversion rate of xylose was gradually increased and the selectivity of xylitol was gradually decreased. The gas flow rate may be no more than 20 ml/min, no more than 15 ml/min, no more than 10 ml/min, or may be 10 ml/min.

When other experimental conditions were kept unchanged, the substrate concentration was increased, and thereby the conversion rate of xylose was gradually increased, and the selectivity of xylitol was gradually decreased. The concentration of the xylose solution may be 0% to 20%, 0% to 15%, 0% to 10%, or 5%.

When other experimental conditions were kept unchanged, the reaction temperature was increased, and thereby the conversion rate of xylose was gradually increased, and the selectivity of xylitol was gradually decreased. The reaction temperature may be from 100° C. to 140° C., from 110° C. to 140° C., from 110° C. to 130° C., or may be 130° C.

When other experimental conditions were kept unchanged, the partial hydrogen pressure was increased, and thereby the conversion of xylose and the selectivity of xylitol were gradually increased. When the hydrogen partial pressure was increased to a certain value, the conversion of xylose and the selectivity of xylitol may tend to be stable. The hydrogen partial pressure may be in a range from 0.3 MPa to 4.0 MPa, from 0.6 MPa to 3.6 MPa, from 1.0 MPa to 3.6 MPa, or from 1.6 MPa to 3.0 MPa.

When other experimental conditions were kept unchanged, and the flow rate of xylose solution was 1.0 ml/min, the conversion of xylose and the selectivity of xylitol reached a maximum value;

When the flow rate of the xylose solution was in a range of 1.0 ml/min to 1.5 ml/min, the conversion rate of xylose and the selectivity of xylitol gradually may decrease as the flow rate of the xylose solution increases;

When the flow rate of the xylose solution was in a range of 1.5 ml/min to 2.5 ml/min, the selectivity of xylitol was gradually increased, but the conversion rate of xylose was lowered. The flow rate of the xylose solution may range from 0.5 ml/min to 2.5 ml/min, from 0.5 ml/min to 2.0 ml/min, or from 0.5 ml/min to 1.0 ml/min, or may be 1.0 ml/min.

At the same time, the effects of the substrate concentration, the reaction temperature, the hydrogen partial pressure, and the substrate flow rate on the hydrogenation reaction were investigated by the single factor experiment using arabinose as the raw materials. Detailed experimental steps and results may be described in detail in the embodiments below.

In the reaction of hydrogenation of the arabinose solution, when other experimental conditions were fixed, the substrate concentration was increased, and the conversion and selectivity of arabinose were not significantly changed. However, the smaller the substrate concentration is, the slower the reaction rate may be. The concentration of the arabinose solution may be in a range from 0% to 20%, from 1% to 15%, from 1% to 10%, or may be 5%.

When other experimental conditions were fixed, the reaction temperature was increased, the conversion rate of arabinose was gradually increased, and the selectivity of arabitol was generally decreased. The reaction temperature may be from 100° C. to 140° C., or from 100° C. to 120° C., or from 110° C. to 120° C., or 110° C.

When other experimental conditions were kept unchanged, the hydrogen partial pressure was increased, the selectivity of arabitol was gradually increased, and the conversion rate of arabinose was not significantly changed. When the hydrogen partial pressure is increased to a certain value, the selectivity of arabitol may be lowered. The hydrogen partial pressure may be from 0.6 to 3.0 MPa, from 0.6 to 2.0 MPa, from 0.6 to 1.6 MPa, or 0.8 MPa.

When the other experimental conditions were kept unchanged, and the flow rate of the arabinose solution was less than 1.0 ml/min, the flow rate of the material had no significant effect on the conversion of arabinose and the selectivity of arabitol;

When the flow rate of the arabinose solution was more than 1.0 ml/min, the selectivity of arabitol decreased gradually as the flow rate of the arabinose solution increased, but the conversion rate of arabinose decreased. The flow rate of the arabinose solution may range from 0.5 ml/min to 2.5 ml/min, from 0.5 ml/min to 2.0 ml/min, or from 0.5 ml/min to 1.0 ml/min. In some embodiments, the flow rate of the arabinose solution may be 0.5 ml/min, 1.0 ml/min, 1.5 ml/min, 2.0 ml/min, or 2.5 ml/min.

The above description about the process of the sugar solution hydrogenation reaction is merely a specific example and should not be considered as the only feasible embodiment. Obviously, for those skilled in the art, after understanding the basic principles of the sugar solution hydrogenation reaction, various modifications and variations in the form and details of the specific embodiment and steps of the sugar solution hydrogenation reaction may be carried out without departing from this principle. However, these modifications and variations are still within the scope of the above description and are within the protection scope of the present disclosure.

Figure 22:
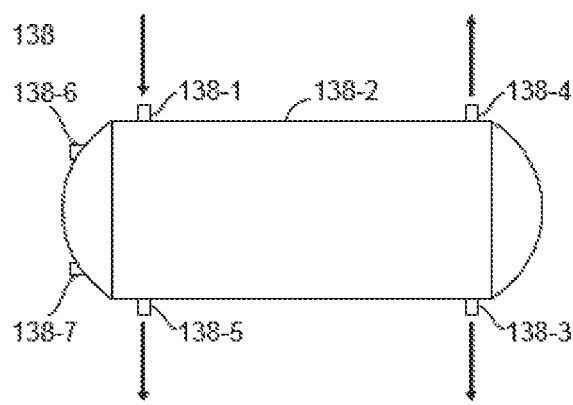
FIG. 22 is a schematic diagram illustrating an exemplary sugar alcohol storage tank according to some embodiments of the present disclosure.

FIG. 22 is a schematic diagram illustrating an exemplary sugar alcohol storage tank according to some embodiments of the present disclosure. The sugar alcohol storage tank 138 may be configured to store a sugar alcohol solution. In some embodiments, the sugar alcohol storage tank 138 may include one or more sugar alcohol inlets 138-1, a chamber 138-2, one or more sugar alcohol outlets 138-3, one or more vents 138-4, one or more effluent outlets 138-5, a level gauge upper interface 138-6, and a level gauge lower interface 138-7.

The sugar alcohol inlet 138-1 may be used for the input of a sugar alcohol solution. The sugar alcohol solution herein may be from the hydrogenation reactor 136. In some embodiments, the sugar alcohol inlet 138-1 may be provided with a strainer. The function of the strainer may be to filter solid residues (hydrogenation catalysts and/or by-products generated in the hydrogenation reaction) which may be included in the sugar alcohol solution to reduce or prevent solid residues from entering the sugar alcohol storage tank. The sugar alcohol inlets 138-1 may be located at or near the top of the chamber 138-2.

The chamber 138-2 may be configured to hold a sugar alcohol solution. The chamber 138-2 may be made of acid-resistant, alkali-resistant, high-temperature resistant, pressure-resistant or wear-resistant materials, for example, metals or alloys (copper, rare earth metals, stainless steel, ductile iron, manganese steel, brass, bronze, white copper, solder, hard aluminum), inorganic materials (ceramics, graphene), polymer materials (organic glass, phenolic resin, ABS resin, polytetrafluoroethylene, polyvinyl chloride, polyethylene, polypropylene), or composite materials (color steel plate, glass steel), or a combination of any of the above materials. In some embodiments, the chamber 138-2 may be transparent to facilitate viewing the liquid level in the sugar alcohol storage tank. In some embodiments, the chamber 138-2 may have a level gauge to facilitate viewing of the liquid level in the sugar alcohol storage tank. The level gauge may be a magnetic float type liquid level gauge, an internal floating liquid level gauge, a magnetic flap level gauge, an input level gauge, or the like. In some embodiments, the chamber 138-2 may be provided with a protective cover. The protective cover functions to insulate heat and protect from light, to reduce or prevent the sugar alcohol solution stored in the chamber 138-2 from undergoing a qualitative change due to absorption of heat and light, and also to reduce the volatilization of the sugar alcohol. In some embodiments, the chamber 138-2 may be provided with a heating device. The function of the heating device is to increase the temperature of the sugar alcohol solution stored in the chamber 138-2, thereby reducing the viscosity of the sugar alcohol solution, improving the fluidity of the sugar alcohol solution, and facilitating the discharge of the sugar alcohol solution.

The sugar alcohol outlet 138-3 may be used for the discharge of the sugar alcohol solution. In some embodiments, the sugar alcohol outlet 138-3 may be provided with a strainer. The function of the strainer is to filter solid residues (hydrogenation catalysts and/or by-products generated in the hydrogenation reaction) which may be included in the sugar alcohol solution to reduce or prevent solid residues from entering a cracking reactor. The sugar alcohol outlet 138-3 may be located at or near the bottom of the chamber 138-2;

The sugar alcohol solution may be discharged by gravity.

The vent 138-4 may be configured to vent the gas in the chamber 138-2 to avoid excessive pressure in the chamber. The gas here may include a sugar alcohol vapor, a small molecule gas generated by decomposition of the sugar alcohol solution, and air. The vent 138-4 may be located at or near the top of the chamber 138-2. In some embodiments, the vent 138-4 may be provided with a gas absorbing device. The function of the gas absorption device is to absorb the organic vapor discharged from the vent 138-4, to reduce or prevent the discharged gas from entering the air to cause pollution or harm.

The vent 138-4 and the sugar alcohol inlet 138-1 may have the same structure or different structures.

The effluent outlet 138-5 may be configured to discharge the solid residue produced in the chamber 138-2. The solid residue herein may be a by-product of the hydrogenation catalyst and/or hydrogenation reaction that enters the chamber 138-2 along with the sugar alcohol solution, or a by-product of the decomposition and/or polymerization of the sugar alcohol solution during storage. The effluent outlet 138-5 is located at or near the bottom of the chamber 138-2. The solid residue may be discharged by gravity.

The effluent outlet 138-5 and the sugar alcohol outlet 138-3 may have the same structure or different structures.

The level gauge upper interface 138-6 and the level gauge lower interface 138-7 may be configured to measure the level of the sugar alcohol solution in chamber 138-2 to detect the storage of the chamber 138-2. A level gauge may be simultaneously connected to the level gauge upper interface 138-6 and the level gauge lower interface 138-7 to detect the liquid level of the chamber 138-2. In some embodiments, the level gauge upper interface 138-6 and the liquid level gauge lower interface 138-7 may be a magnetic float type level gauge, an internal floating level gauge, a magnetic flap level gauge, and an input level gauge, etc. In some embodiments, the level gauge upper interface 138-6 may be located at the upper portion of the chamber 138-2, and the level gauge lower interface 138-7 may be located at the lower portion of the chamber 138-2.

The above description of the sugar alcohol storage tank is merely a specific example and should not be considered as the only feasible embodiment. Obviously, it will be apparent to those skilled in the art that upon understanding the basic principles of the sugar alcohol storage tank, various modifications and variations in the form and details of the structure and construction of the sugar alcohol storage tank may be carried out without departing from this principle. However, these modifications and variations are still within the scope of the above description. In some embodiments, some devices may be added or subtracted from the sugar alcohol storage tank. For example, the level gauge upper interface 138-6 and the level gauge lower interface 138-7 may not be included in the sugar alcohol storage tank. For example, the sugar alcohol storage tank may not include the vent 138-4 and/or the effluent outlet 138-5. For example, the chamber 138-2 in the sugar alcohol storage tank may have a fixed device or a buffer device to reduce or avoid sloshing or large-scale movement of the sugar alcohol storage tank. Such variations are within the protection scope of the present disclosure.

Figure 23:
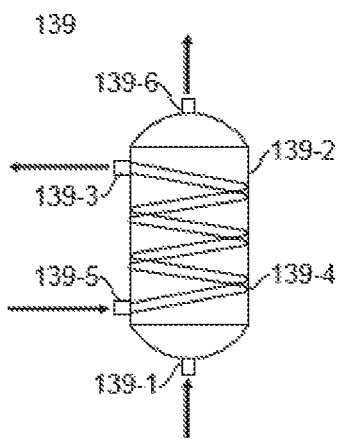
FIG. 23 is a shematic diagram illustrating an exemplary sugar alcohol preheating tank according to some embodiments of the present disclosure.

FIG. 23 is a schematic diagram illustrating an exemplary sugar alcohol preheating tank according to some embodiments of the present disclosure. The sugar alcohol preheating tank 139 may heat the sugar alcohol solution and discharge the sugar alcohol solution, the temperature of which has been increased, to a cracking tank 140. In some embodiments, the sugar alcohol solution may also enter the cracking reactor 140 directly without passing through the sugar alcohol preheating tank 139. In some embodiments, the operating temperature of the sugar alcohol preheating tank is in a range of 180° C. to 240° C., 195° C. to 235° C., 200° C. to 230° C., or 210° C. to 225° C., etc.

In some embodiments, there may be two or more sugar alcohol preheating tanks 139 which are heated stepwise to achieve a temperature suitable to enter the cracking reactor 140.

As shown in FIG. 23, the sugar alcohol preheating tank 139 may include a sugar alcohol inlet 139-1, a chamber 139-2, a heat transfer oil inlet 139-3, a heat transfer oil conduit 139-4, a heat transfer oil outlet 139-5, and a sugar alcohol outlet 139-6, or the like. The chamber 139-2 may be made of stainless steel or other materials that are resistant to high temperatures and corrosion. The chamber 139-2 may form a container to accommodate the sugar alcohol solution. The heat transfer oil conduit 139-4 may be placed inside the chamber 139-2 in a spiral or coiled form.

The heat transfer oil may enter the heat transfer oil conduit 139-4 from the heat transfer oil inlet 139-3. Through the heat transfer oil outlet 139-5, the heat transfer oil may leave the heat transfer oil conduit 139-4 to end the heat exchange with the sugar alcohol solution. After leaving the sugar alcohol preheating tank 139, the heat transfer oil may be returned to a total heat transfer oil reservoir or may enter other devices that require heat exchange, such as other sugar alcohol preheating tanks 139 or the cracking reactor 140. In some embodiments, the heat transfer oil may have a temperature slightly higher than the operating temperature of the sugar alcohol preheating tank.

The sugar alcohol solution may enter the chamber 139-2 from the sugar alcohol inlet 139-1. Within the chamber 139-2, the sugar alcohol solution may be in contact with the heat transfer oil conduit 139-4 placed within the chamber. Since the heat transfer oil conduit 139-4 may be filled with heat transfer oil with a relatively high temperature, heat may be conducted from the heat transfer oil conduit 139-4 to the sugar alcohol solution. After being heated, the sugar alcohol solution may leave the sugar alcohol preheating tank 139 from the sugar alcohol outlet 139-6.

The above description of the sugar alcohol preheating tank is merely a specific example and should not be considered as the only feasible embodiment. Obviously, for those skilled in the art, after understanding the basic principles of the operation of the sugar alcohol preheating tank, various modifications or improvements in the form and details of the specific embodiments and steps of the sugar alcohol preheating tank may be carried out without departing from this principle. However, these modifications and variations are still within the scope of the above description.

In some embodiments, other types of heating devices may be placed in the sugar alcohol preheating tank, such as, an electric heating device, a high frequency heating device, or a microwave heating device. These variations or improvements are within the protection scope of the present disclosure.

Figure 24:
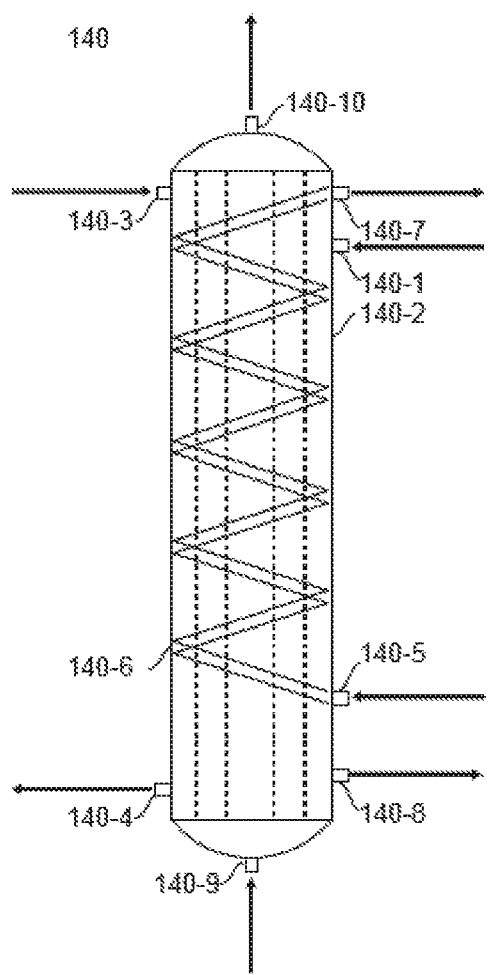
FIG. 24 is a shematic diagram illustrating an exemplary cracking reactor according to some embodiments of the present disclosure.

FIG. 24 is a schematic diagram illustrating an exemplary cracking reactor according to the present disclosure. The function of the cracking reactor 140 is to provide a hydrogen atmosphere to heat the sugar alcohol solution to cleave the sugar alcohol to obtain a mixed solution of various diols.

The cracking reactor 140 may include a sugar alcohol inlet 140-1, a reaction chamber 140-2, a hydrogen inlet 140-3, a hydrogen outlet 140-4, an insulated heat transfer oil inlet 140-5, an insulated heat transfer oil conduit 140-6, an insulated heat transfer oil outlet 140-7, a diol outlet 140-8, a heating heat transfer oil inlet 140-9, and a heating heat transfer oil outlet 140-10.

The sugar alcohol inlet 140-1 is used for the entry of the sugar alcohol solution. The sugar alcohol solution may enter continuously or intermittently depending on the operational characteristics of the system 100. When the system 100 is continuously operated, the sugar alcohol solution may be immediately introduced into the reaction chamber 140-2 from the sugar alcohol inlet 140-1 after being generated. In some embodiments, the sugar alcohol solution may also be stored after being generated. When the next step is required, the sugar alcohol solution may enter the reaction chamber 140-2 through the inlet 140-1.

The reaction chamber 140-2 may be configured to define a space to accommodate the sugar alcohol solution, the high pressure hydrogen, the cracking catalyst, and the glycol solution formed after the reaction. The reaction chamber 140-2 may be loaded with a catalyst carrier and a cracking catalyst (not shown in FIG. 24). In some embodiments, the reaction chamber 140-2 may be made of materials resistant to a high temperature and high pressure, such as stainless steel.

The hydrogen inlet 140-3 and the hydrogen outlet 140-4 may be configured to allow hydrogen to enter and exit from the reaction chamber 140-2, respectively.

After hydrogen enters the reaction chamber 140-2, a reducing hydrogen atmosphere may be formed. The hydrogen atmosphere may have hydrogen pressure. In some embodiments, the hydrogen pressure is from 2.0 MPa to 10.0 MPa, from 4.0 MPa to 8.0 MPa, from 4.5 MPa to 7.0 MPa, or the like. In some embodiments, the hydrogen pressure may be about 2.0 MPa, 3.0 MPa, 4.0 MPa, 5.0 MPa, 6.0 MPa, 7.0 MPa, or 8.0 MPa.

The insulated heat transfer oil inlet 140-5, the insulated heat transfer oil conduit 140-6, and the insulated heat transfer oil outlet 140-7 together form a heat insulating device. The heat transfer oil may enter the insulated heat transfer oil conduit 140-6 from the insulated heat transfer oil inlet 140-5. In the insulated heat transfer oil conduit 140-6, the heat transfer oil may exchange heat with the sugar alcohol solution, hydrogen, and the catalyst in the chamber 140-2 to maintain the temperature of the reaction system relatively stable. The heat transfer oil may leave through the insulated heat transfer oil outlet 140-7.

The heating heat transfer oil inlet 140-9 and the heating heat transfer oil outlet 140-10 together form a heating device. The heat transfer oil may enter a heating pipe (not shown) from the heating heat transfer oil inlet 140-9. In the heating pipe, the heat transfer oil may exchange heat with the sugar alcohol solution, hydrogen, and the catalyst in the chamber 140-2 to raise the temperature of the reactants and promote the reaction. The heat transfer oil may be removed by heating heat transfer oil outlet 140-10.

In the case of a high temperature and high pressure, and the presence of hydrogen, the sugar alcohol may be cleaved into a polyol such as ethylene glycol, 1,2-propanediol, 1,3-propanediol, or glycerin. The heat transfer oil heating device may maintain the relative stability of the reaction temperature. In some embodiments, the reaction temperature may be in a range of 180° C. to 240° C., 200° C. to 235° C., 210° C. to 225° C., or in a range of 220° C. to 225° C.

After cleavage, the solution in which the polyol is dissolved may exit from the chamber 140-2 via the solution outlet 140-8. The solution may be input into the subsequent device for separation and other operations.

The above description of the cracking reactor is merely a specific example and should not be considered as the only feasible embodiment. Obviously, for those skilled in the art, after understanding the basic principles of the operation of the cracking reactor, it is possible to carry out various modifications or improvements in the form and details of the specific embodiment and steps of the cracking reactor without departing from this principle. However, these modifications and variations are still within the scope of the above description. In some embodiments, other types of heating devices may be placed in the cracking reactor, for example, an electric heating device, a high frequency heating device, or a microwave heating device. In some embodiments, the cracking reactor may also have a catalyst inlet and/or a catalyst outlet to allow the entry and discharge of the catalyst. These variations or improvements are within the protection scope of the present disclosure.

FIG. 25-A is a schematic diagram illustrating an exemplary cracking mechanism of sugar alcohol according to some embodiments of the present disclosure.

The cracking of the sugar alcohol may be carried out under a hydrogen atmosphere at a high temperature. Under the reaction condition of hydrogen alcohol hydrogenolysis, both the C—C bond and the C—O bond in the sugar alcohol may be broken. Therefore, for the polyols of which the sugar alcohol is cleaved into small molecules, the cracking reaction catalyst is required to have higher selectivity.

The cracking of sugar alcohol molecules may follow the following reaction mechanism. First, sugar alcohol molecules such as sorbitol dehydrogenate to form the corresponding aldehyde or ketone intermediate on the surface of the catalyst. The C—C in the intermediate molecule is close to the surface of the catalyst, and a reverse aldol condensation reaction may occur under certain conditions. The C—C bond in the molecule may be cleaved, and the resulting bond-breaking product may be a molecule of aldehyde and a molecule of a ketone including a hydroxyl group. The aldehyde and ketone in the product may be separately hydrogenated to form the corresponding small molecule polyol.

The cracking reaction of the sugar alcohol may be carried out by heating in the presence of the catalyst. The component including the transition metal may be used as the catalyst for the cracking reaction. The transition metal may have high catalytic activity for the cracking of the C—C bond during the cracking of the sugar alcohol. In some embodiments, the transition metal in the cracking reaction catalyst may include a non-noble metal such as Cu or Ni, and a noble metal such as Ir, Pt, Pd, Ru, Rh, or the like. The component including the transition metal may be a metal element (such as Cu, Ni, Ir, Pt, Pd, Ru, Rh), metal oxides (such as $CuO$, $Cu_2O$, $Ni_2O_3$, $PtO_2$, $PdO_2$), metal salts (such as $NiSO_4$, $NiCl_2$, $Ni(HCO_3)_2$, $RuCl_2$, $RuCl_4$), metal carbonyl compounds (such as $Ni(CO)_4$), other metal compounds (such as a metal hydride, hydroxide, sulfide, boride, nitride, etc.) or the like, or any combination thereof.

The above component including the transition metal may be used singly or may be loaded on a carrier. The carrier herein may be a porous material or particles having a large specific surface. In some embodiments, the carrier may include porous carbon/activated carbon, MgO, $Al_2O_3$, $SiO_2$, amorphous silica alumina, zeolite molecular sieves (such as ZSM-5, SBA-15, etc.), $TiO_2$, $ZrO_2$, $WO_3$, ZnO.

In some embodiments, a component including Cu may be used as a catalyst for the cracking reaction. The component may include 10% to 50% by mass of metal Cu and 50% to 90% by mass of $Al_2O_3$. Metal Cu may be used as an active ingredient for catalytic cleavage. $Al_2O_3$ may be used as a catalyst carrier. The binding strength of Cu catalyst to the C atom in the organic molecule may be moderate, and the cracking reaction may be controlled well. In addition, during the catalytic cracking process, the sugar alcohol may generate $CO_2$ or a carboxylic acid during the C—C bond cleavage, so that the solution system exhibits weak acidity. Metal Cu may resist acid corrosion and maintain long-lasting catalytic activity.

FIG. 25-B is a flowchart illustrating an exemplary process for sugar alcohol cracking according to some embodiments of the present disclosure. In 2510, a sugar alcohol solution including at least one sugar alcohol may be provided. The solution may include at least one sugar alcohol such as sorbitol, xylitol, and arabitol. In some embodiments, the mass percentage concentration of the sugar alcohol in the sugar alcohol solution may be 1% to 20%, 5% to 20%, 10% to 20%, or the like.

In 2520, a catalyst component may be provided to be in contact with the sugar alcohol solution. Details about the catalyst component may refer to the related description of FIG. 24.

In 2530, the sugar alcohol solution and the catalyst component may be heated in a hydrogen atmosphere to obtain a glycol solution. The hydrogen atmosphere may have a hydrogen pressure. In some embodiments, the hydrogen pressure may be from 2.0 MPa to 10.0 MPa, from 4.0 MPa to 8.0 MPa, or from 5.0 MPa to 7.0 MPa.

Heating the sugar alcohol solution with the catalyst component may allow the sugar alcohol solution to maintain a reaction temperature with the catalyst component. In some embodiments, the reaction temperature may be in a range of 180° C. to 240° C., 195° C. to 235° C., 200° C. to 230° C., or 210° C. to 225° C.

The alcohol solution obtained in 2530 may include a plurality of different alcohols. In some embodiments, the alcohol solution may include at least one polyol. In some embodiments, the alcohol solution may include at least one of ethylene glycol, 1,2-propanediol, 1,3-propanediol, or glycerin.

In some embodiments, the alcohol solution obtained in 2530 may include some inorganic salt components in addition to the alcohol. In some embodiments, the inorganic salt component may include potassium chloride, potassium phosphate, sodium chloride, calcium phosphate, magnesium phosphate, or the like. These inorganic salts may be recycled by certain means.

In order to understand the influence of different factors on the cracking reaction and determine the appropriate range of reaction conditions, a plurality of experiments may be designed. After degradation and catalytic hydrogenation of the biological object, the solution may usually include xylose, arabinose, glucose, sorbitol, arabitol and xylitol. An experiment was carried out on a xylitol solution, a sorbitol solution, and a mixed solution including xylose, glucose, and arabinose. In the experiment, the effects of the hydrogen pressure, the reaction temperature, the xylitol solution concentration, and the xylitol solution flow rate on xylitol cracking reaction were investigated by a single factor experiment. The specific experimental procedures and results may be described in detail in Embodiment Seventeen to Embodiment Twenty.

In the xylitol hydrocracking reaction, when the other experimental conditions were kept unchanged, increasing the hydrogen pressure in a range of 3 to 7 MPa may increase the conversion rate of the reaction. However, the selectivity of 1,2-propanediol decreases with increasing hydrogen pressure. In addition, the selectivity of glycerol gradually increases between 3 MPa and 5 MPa, and gradually decreases between 5 MPa and 7 MPa.

Increasing the reaction temperature may increase the conversion rate and also increasing the selectivity of 1,2-propanediol. At lower reaction temperatures, xylitol hydrocracking produces glycerol and glycerol is less cleaved, so glycerol selectivity is greater. At higher reaction temperatures, the glycerol produced by the hydrogenolysis of xylitol is more hydrogenolyzed, so the selectivity of glycerol decreases at higher reaction temperatures, and the selectivity of 1,2-propanediol increases. Ethylene glycol has little change in selectivity after 215° C. By comparing the conversion at each reaction temperature with the selectivity of 1,2-propanediol, it is concluded that: under the above reaction conditions, although the xylose conversion rate and the 1,2-propanediol selectivity are both large at 235° C., the values of the two indexes are almost the same between 215° C. and 235° C. When the temperature is increased by 20° C., the yield is not significantly improved, and energy consumption is large. In addition, the selectivity of ethylene glycol is basically unchanged at 215° C. to 235° C. In order to avoid reducing the economic efficiency, the reaction temperature is selected to be 215° C. under the above reaction conditions.

Although the conversion rate of the reaction is lowered, the selectivity of glycerol, 1,2-propanediol and ethylene glycol is greatly improved, and the yields of glycerin, 1,2-propanediol and ethylene glycol are higher because the concentration of the xylitol solution is increased. Therefore, the concentration of the polyol in the solution after the reaction may be increased by increasing the concentration of the xylitol solution. A higher concentration of xylitol solution may be selected as the raw materials for the cracking reaction.

When the other experimental conditions are kept unchanged, as the flow rate of the xylitol solution increases, the conversion rate, the selectivity of 1,2-propanediol, the selectivity of glycerol, and the selectivity of ethylene glycol are gradually decreases, and both of them are decreased rapidly at the initial stage of the reaction, and then decreased slowly. Under the condition of large flow rate, in a trickle bed reactor, the residence time of the reactants is shortened, and the contact time of the reactants with the catalyst is too short, so that the catalytic reaction is incomplete;

Under the condition of low flow rate, in the trickle bed reactor, the residence time of the reactants is longer, the contact time of the reactants with the catalyst is prolonged, and the catalytic reaction is relatively complete. By calculating the yield of 1,2-propanediol, it is concluded that under the above reaction conditions, the yield reached the maximum when the feed rate of the xylitol solution is 0.5 ml/min. Under the above reaction conditions, the yield of ethylene glycol was also maximized when the feed rate of xylitol solution is 0.5 ml/min, so the feed rate was chosen to be 0.5 ml/min.

In the experiment, the effects of hydrogen pressure and reaction temperature on the sorbitol cracking reaction were investigated by the single factor experiment. The specific experimental procedures and results are described in detail in Example Twenty-One to Example Twenty-Two in the examples.

In the reaction of sorbitol hydrocleavage, as the hydrogen pressure increased, the conversion of the reaction increased. The conversion rate increased relatively between 4 MPa and 6 MPa. The conversion rate between 6 MPa and 8 MPa was relatively small. Under the above reaction conditions, the selectivity of 1,2-propanediol reached a maximum at 6 MPa, and the selectivity of ethylene glycol also reached a maximum at 6 MPa. Under the above reaction conditions, the selectivity of glycerol gradually decreased from 4 MPa to 6 MPa, and the selectivity was minimal at 6 MPa, indicating that cleaved glycerol was more and more 1,2-propanediol was formed.

In the reaction of sorbitol hydrocleavage, as the reaction temperature increases, the conversion of the reaction increased. The selectivity of 1,2-propanediol gradually increased between 195° C. and 225° C., but there was a sign of significant decrease at 225° C., and then showed a tendency to balance. When the temperature was higher than 205° C., the selectivity of ethylene glycol was not obvious at various temperatures in the experiment, and the selectivity of 1,2-propanediol was large. Both products had higher selectivity and conversion at 225° C. Therefore, under the above reaction conditions, the experiment was carried out by selecting a reaction temperature of 225° C. Under the above reaction conditions, glycerol may also produce 1,2-propanediol by hydrocleavage. The selectivity of glycerol was higher at 195° C., but when the selectivity of 1,2-propanediol began to increase, the selectivity of glycerol began to decrease, indicating that glycerol cracking produced 1,2-propanediol.

The above description of the sugar and/or sugar alcohol cracking reaction scheme was merely a specific example and should not be considered as the only feasible embodiment. Obviously, for those skilled in the art, after understanding the basic principles of sugar and/or sugar alcohol cracking reactions, it is possible that various modifications and variations in the form and details of the specific embodiments and steps of the sugar and/or sugar alcohol cracking reaction may be made without departing from this principle. However, these modifications and variations are still within the scope of the above description. In some embodiments, the mixed solution may include one or more of xylose, glucose, arabinose, xylitol, arabitol, sorbitol, or the like.

Figure 26:
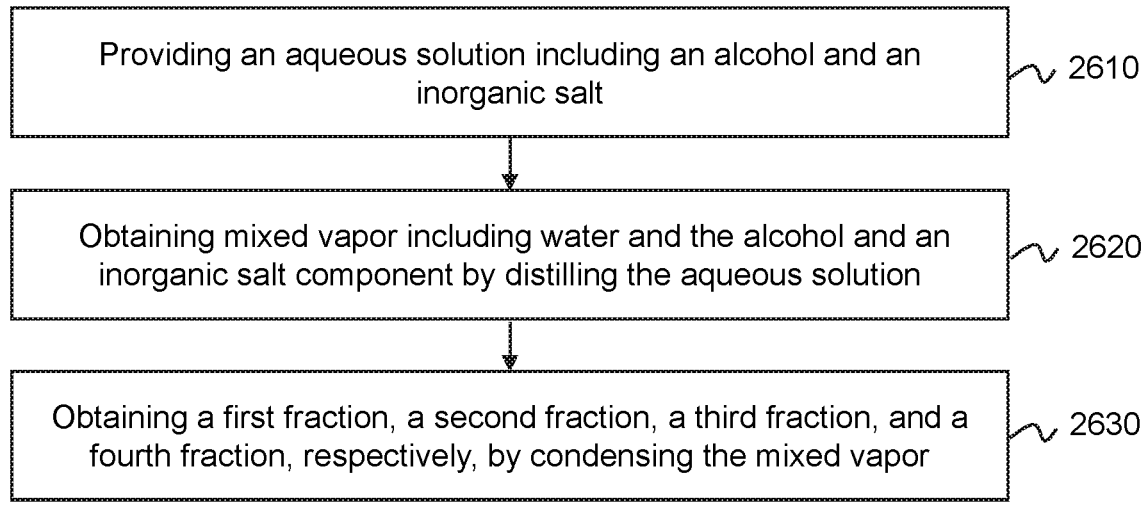
FIG. 26 is a flowchart illustrating an exemplary process for separating inorganic salts and alcohol according to some embodiments of the present disclosure.

FIG. 26 is a flowchart illustrating an exemplary process for separating inorganic salts and alcohols according to some embodiments of the present disclosure. In 2610, an aqueous solution including an alcohol and an inorganic salt may be provided. The above aqueous solution may be an alcohol solution obtained after the cracking reaction. Since the inorganic salt does not react under the high temperature and high pressure, it remains in the solution in the chamber 140-2 of the cracking reactor 140. The inorganic salt may flow out of the solution outlet 140-8 along with the alcohol and water. The alcohol included in the alcohol solution may be one or more of ethylene glycol, 1,2-propanediol, 1,3-propanediol, or the like.

In 2620, the aqueous solution may be subjected to distillation to obtain mixed vapor including water and the alcohol and an inorganic salt component. In some embodiments, vacuum distillation may be carried out at less than 1 atmosphere. In some embodiments, the distillation may also be atmospheric distillation. In some embodiments, the aqueous solution may be heated to 150° C. at 2 kPa to vaporize the water and the alcohol. The inorganic salt thus remains in the solid phase.

Since the inorganic salt may be combined with water, moisture may remain in the inorganic salt component of the solid phase. In some embodiments, the solid phase inorganic salt component may be further dried. Drying methods may include sun exposure, infrared drying, in contact with a desiccant, evaporation, vacuum drying, or the like. In some embodiments, the inorganic salt component may be dried in the evaporator 148 shown in FIG. 1.

The inorganic salt component includes a plurality of inorganic salts such as potassium chloride, potassium phosphate, sodium chloride, magnesium chloride or the like. In some embodiments, the inorganic salt component may be directly used as a fertilizer for agricultural purposes without separating the inorganic salt compounds. In some embodiments, different kinds of inorganic salts may be separated from the components by operations such as recrystallization.

In 2630, the mixed vapor may be condensed to obtain a first fraction, a second fraction, a third fraction, and a fourth fraction, respectively. Condensation of the mixed vapor may be carried out at a normal atmospheric pressure or under a reduced pressure. In some embodiments, the mixed vapor may be stepwise condensed in different temperature in a range from 600 mmHg to 750 mmHg atmospheric pressure.

In some embodiments, the first fraction may be a mixture of primarily aqueous and other low boiling organics. The low boiling organics may include one or more of ethanol, diethyl ether, propanol, or the like. The first fraction may be collected by making the mixed vapor pass through a condenser tube at a temperature ranging from 43° C. to 78° C., from 45° C. to 75° C., or from 50° C. to 70° C.

In some embodiments, the second fraction may be a mixture mainly including 1,2-propanediol. The second fraction may be collected by making the mixed vapor pass through a condenser tube at a temperature ranging from 95° C. to 105° C. or from 100° C. to 105° C.

In some embodiments, the third fraction may be a mixture mainly including ethylene glycol. The third fraction may be collected by making the mixed vapor pass through a condenser tube at a temperature range of 106° C. to 110° C. or from 106° C. to 109° C.

In some embodiments, the fourth fraction may be a mixture mainly including 1,3-propanediol. The fourth fraction may be collected by making the mixed vapor pass through a condenser tube at a temperature ranging from 110° C. to 116° C. or from 113° C. to 118° C.

The first fraction, the second fraction, the third fraction, and the fourth fraction may be collected in respective storage tanks.

Figure 27:
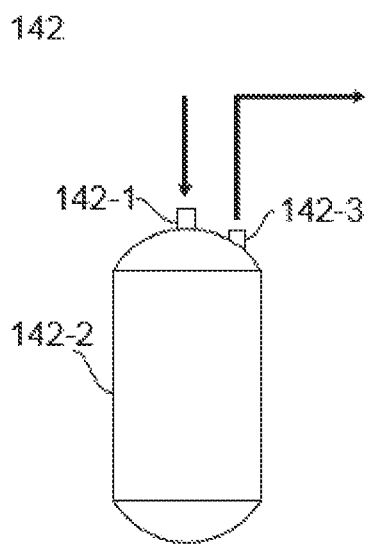
FIG. 27 is a schematic diagram illustrating an exemplary alcohol storage tank according to some embodiments of the present disclosure.

FIG. 27 is a schematic view of an alcohol storage tank according to some embodiments of the present disclosure. The alcohol storage tank 142 may include an inlet 142-1, a tank body 142-2 and an outlet 142-3.

The alcohol storage tank may be configured to receive and store fractionated alcohols including only a small amount of impurities. There are a plurality of alcohol storage tanks, and each of the alcohol storage tanks may receive the first fraction, the second fraction, the third fraction, and the fourth fraction.

The inlet 142-1 of the alcohol storage tank 142 may be connected to a condenser to receive condensate from the condenser. The tank body 142-2 may be made of organic-resistant stainless steel or carbon steel. In some embodiments, the outlet 142-3 of the alcohol storage tank 142 may be connected to the vacuum pump through a pipe.

In some embodiments, the tank body 142-2 may be provided with two interfaces for installing the level gauge. The position of the liquid level in the tank body 142-2 and the filling condition of the alcohol storage tank 142 may be known by reading of the level gauge. When the level gauge shows that the tank body is about to be filled, the alcohol may be pumped from the outlet 142-3.

EMBODIMENT

The embodiments described below are for illustrative purposes only and do not constitute a limitation on the scope of protection of the present disclosure.

Embodiment One

The straw stalks after screening with different meshes were used in bioreactor degradation experiments to test the effect of straw particle size on biological object degradation.

The naturally dried straw stalk was pulverized by a micro-pulverizer, and then sieved through sieves of different mesh numbers to obtain straw particles of different sizes, which are respectively sealed and bagged for use. The crushed and sieved straw, catalyst, and water were sequentially added to the autoclave in order, sealed and tightened, and then the gas in the kettle was replaced with hydrogen three times, and leaked. After checking, the temperature and number of revolutions were set, the pressure was adjusted, and the experiment was carried out. During the experiment, monitoring the reaction temperature should be pay attention to. If the reaction temperature is too high, the condensate should be turned on in time to cool down. After the reaction is completed, the heating voltage was turned off, and the condensed water was cooled. After the reactor was cooled, the gas in the kettle was evacuated and sampled.

The obtained sample was filtered through a 0.45 μm water filtration membrane, and the concentration of the sugar solution was measured using a Shimadzu LC-20AT liquid chromatograph. The detector was RID-10A refractive index, the column was Shodex SC1011, the mobile phase was water, the column temperature was 80° C., the flow rate was 1.0 ml/min, and the injection volume was 10 μl. After analysis by liquid chromatography, peak areas of different sugars were obtained. The concentration of glucose, xylose and arabinose was determined according to the standard curve regression equation, and the total sugar concentration was the sum of the respective sugar concentrations. The remaining residue after the completion of the reaction was washed and dried to calculate the degradation rate of the straw, as in Formula (1):

$$\text{Degradation rate} = (M-m)/M \times 100\% \qquad (1)$$

wherein M is the mass of the straw before the reaction, and m is the mass of the straw after the reaction. In the experiment, the effects of the straw particle size, the reaction pressure, the reaction time, the reaction temperature, the solid-liquid ratio (a mass ratio of straw to water), the solid-solid ratio (a mass ratio of catalyst to straw), and the stirring speed on straw degradation were investigated through the single factor experimental method. The details are described as follows.

Under the experimental conditions of a temperature of 140° C., the solid-solid ratio (a mass ratio of catalyst to straw) of 3:10, the ratio of solid to liquid (a mass ratio of straw to water) of 1:10, the stirrer speed of 500 rpm, the pressure of hydrogen of 4.0 MPa, and the reaction time of 4 hours, the straw after sieving with different meshes of the standard mesh was used as the reaction raw materials for degradation experiments. The specific experimental data is shown in Table 1.

TABLE 1

Effect of straw particle size on the reaction

| Straw particle size (mesh) | Degradation rate (%) | Sugar concentration (g/l) |
|---|---|---|
| ~10 | 39.9 | 6.105 |
| 10~20 | 48.7 | 9.241 |
| 20~60 | 49.8 | 12.708 |
| 60~100 | 46.5 | 8.654 |
| ~100 | 43.9 | 7.258 |

Embodiment Two

The biological object degradation experiments conducted under different reaction pressure tested the effect of reaction pressure on biological object degradation. The pre-processing of straw, the experimental operation of straw degradation and the analysis of experimental results were same as Embodiment One.

The degradation experiments were carried out under different reaction pressure under the experimental conditions of straw particles of 20 meshes to 60 meshes, the temperature of 140° C., the solid-solid ratio (a mass ratio of catalyst to straw) of 3:10, the solid-liquid ratio (a mass ratio of straw to water) of 1:10, the speed of the stirrer 500 rpm, and reaction time of 4 hours. The specific experimental data is shown in Table 2.

TABLE 2

Effect of reaction pressure on the reaction

| Reaction pressure (MPa) | Degradation rate (%) | Sugar concentration (g/l) |
|---|---|---|
| 1.0 | 49.2 | 12.905 |
| 1.5 | 49.8 | 12.978 |
| 2.0 | 48.4 | 11.919 |
| 3.0 | 46.4 | 9.004 |
| 4.0 | 41.7 | 5.934 |

Embodiment Three

Biological object degradation experiments conducted at different reaction times explored the effect of reaction time on biological object degradation. The pre-processing of straw, the experimental operation of straw degradation, and the analysis of experimental results were same as Embodiment One.

Under the experimental conditions of the straw particles of 20 meshes to 60 meshes, the temperature of 140° C., the hydrogen pressure of 1.5 MPa, the solid-solid ratio (a mass ratio of catalyst to straw) of 3:10, and the solid-liquid ratio (a mass ratio of straw to water) of 1:10, the speed of the stirrer of 500 rpm, the degradation experiments were carried out at different reaction times. The specific experimental data is shown in Table 3.

TABLE 3

Effect of reaction time on the reaction

| Reaction time (hour) | Degradation rate (%) | Sugar concentration (g/l) |
|---|---|---|
| 0.5 | 45.8 | 8.863 |
| 1.0 | 49.7 | 13.238 |
| 2.0 | 51.2 | 14.698 |
| 3.0 | 51.7 | 13.865 |
| 4.0 | 51.3 | 13.440 |

Embodiment Four

Biological object degradation experiments were carried out at different reaction temperatures to explore the effect of the reaction temperature on biological object degradation. The pre-processing of straw, the experimental operation of straw degradation, and the analysis of experimental results were same as the first example.

Degradation experiments were carried out at different reaction temperatures under experimental conditions of the straw particles of 20 to 60 meshes, the pressure of hydrogen of 1.5 MPa, the solid-solid ratio (a mass ratio of catalyst to straw) of 3:10, the ratio of solid to liquid (a mass ratio of straw to water) of 1:10, the speed of the stirrer of 500 rpm, and the reaction time of 2 hours. The specific experimental data is shown in Table 4.

TABLE 4

Effect of reaction temperature on the reaction

| Reaction temperature (° C.) | Degradation rate (%) | Sugar concentration (g/l) |
|---|---|---|
| 110 | 19.6 | 0.614 |
| 120 | 25.3 | 0.990 |
| 130 | 47.6 | 8.061 |
| 140 | 50.1 | 13.451 |
| 150 | 50.0 | 11.961 |

Embodiment Five

The biological object degradation experiments under different solid-liquid ratios (a mass ratio of straw to water) explored the effect of the solid-liquid ratio on biological object degradation. The pre-processing of straw, the experimental operation of straw degradation and the analysis of experimental results were same as Embodiment One.

Under the experimental conditions of the straw particles of 20 to 60 meshes, the temperature of 140° C., the hydrogen pressure of 1.5 MPa, the solid-solid ratio (a mass ratio of catalyst to straw) of 3:10, the speed of the stirrer of 500 rpm, and the reaction time of 2 hours, the degradation experiments were carried out at different solid-liquid ratios. The specific experimental data is shown in Table 5.

TABLE 5

Effect of solid-liquid ratio on the reaction

| Solid-liquid ratio (g:g) | Degradation rate (%) | Sugar concentration (g/l) |
|---|---|---|
| 1:6 | 44.9 | 5.906 |
| 1:7 | 48.5 | 6.403 |
| 1:8 | 49.9 | 8.43 |

TABLE 5-continued

Effect of solid-liquid ratio on the reaction

| Solid-liquid ratio (g:g) | Degradation rate (%) | Sugar concentration (g/l) |
|---|---|---|
| 1:9 | 48.4 | 8.335 |
| 1:10 | 51.8 | 18.397 |
| 1:11 | 48.3 | 12.331 |

Embodiment Six

The biological object degradation experiments under different solid-solid ratios (a mass ratio of catalyst to straw) explored the effect of the solid-solid ratio on biological object degradation. The pre-processing of straw, the experimental operation of straw degradation, and the analysis of experimental results are same as the first example.

Degradation experiments were carried out at different solid-solid ratios under the experimental conditions of straw particles of 20 to 60 meshes, the temperature of 140° C., the hydrogen pressure of 1.5 MPa, the solid-liquid ratio (a mass ratio of straw to water) of 1:10, the stirrer speed of 500 rpm, and reaction time of 2 hours. The specific experimental data is shown in Table 6.

TABLE 6

Effect of solid-solid ratio on the reaction

| Solid-solid ratio (g:g) | Degradation rate (%) | Sugar concentration (g/l) |
|---|---|---|
| 1:10 | 43.8 | 7.001 |
| 2:10 | 48.3 | 10.274 |
| 3:10 | 51.3 | 14.998 |
| 4:10 | 50.2 | 11.092 |
| 5:10 | 52.7 | 13.822 |

Embodiment Seven

The biological object degradation experiments were carried out at different agitation speeds to explore the effect of the stirring speed on biological object degradation. The pre-processing of straw, the experimental operation of straw degradation, and the analysis of experimental results were same as Embodiment One.

Degradation experiments were carried out under different stirring speeds under the experimental conditions of 20 to 60 meshes straw particles, the temperature of 140° C., the hydrogen pressure of 1.5 MPa, the solid-solid ratio (a mass ratio of catalyst to straw) of 3:10, the solid-liquid ratio (a mass ratio of straw to water) of 1:10, and a reaction time of 2 hours. The specific experimental data is shown in Table 7. In the table below, the unit of speed is revolutions per minute, that is, the number of revolutions per minute.

TABLE 7

Effect of speed on the reaction

| Stirring speed (r/min) | Degradation rate (%) | Sugar concentration (g/l) |
|---|---|---|
| 400 | 50.3 | 10.776 |
| 500 | 50.7 | 14.998 |
| 600 | 51.3 | 15.368 |
| 700 | 51.8 | 15.726 |
| 800 | 52.5 | 15.596 |

Embodiment Eight

Sugar solution hydrogenation experiments were carried out under different experimental conditions. The effects of reaction temperature, hydrogen pressure, xylose solution concentration, solution feed flow rate and tail gas flow rate on the hydrogenation reaction of the sugar solution were investigated.

A xylose solution was used as raw materials in the experiment. After 595.04 g of the Ni/Al2O3 catalyst and the filling were packed in a fixed bed reactor, the device was sealed and the source was opened. The air in the reactor was replaced with the hydrogen gas one or more times (e.g., 4 to 5 times), and leak detection was performed. If there is no gas leakage, the heating was started, and after the reaction temperature was reached, certain pressure of hydrogen was introduced and the pressure was kept constant. A certain concentration of raw materials was pumped into the trickle bed with a metering pump at a certain flow rate. After the reaction was completed, the gas source and each valve are closed, the power is turned off, the gas in the reactor is emptied, and sampling is performed.

The obtained sample was filtered through a 0.45 µm aqueous filter, and the concentration of the sugar alcohol solution was measured using a Shimadzu LC-20AT liquid chromatograph. The detector was RID-10A refractive index, the column was Shodex SC1011, the mobile phase was water, the column temperature was 80° C., the flow rate was 1.0 ml/min, and the injection volume was 10 µl. After analysis by liquid chromatography, the peak area of the sugar alcohol was obtained. According to the standard curve regression equation, the concentration of sugar alcohol was determined, and the mass of sugar alcohol was calculated according to Formula (2).

The main formula for the preparation of xylitol by hydrogenation of xylose under certain conditions of temperature, pressure and concentration is as follows:

$$W_{xylitol} = C_{xylose} \times V \times n \quad (2)$$

The conversion rate of the xylose refers to the mass ratio of the quality of the converted xylose to the initial xylose. The xylose conversion rate is calculated according to Formula (3).

$$X_{xylose} = \frac{W^0_{xylose} - W_{xylose}}{W^0_{xylose}} \times 100\% \quad (3)$$

The xylitol selectivity refers to the ratio of the mass of xylitol produced by the reaction to the mass of converted xylose. The xylitol selectivity is calculated according to Formula (4).

$$S_{xylitol} = \frac{W_{xylitol} \times M_{xylose}/M_{xylitol}}{W^0_{xylose} - W_{xylose}} \times 100\% \quad (4)$$

wherein:

$X_{xylose}$: conversion rate of the xylose;
$S_{xylitol}$: xylitol selectivity;
$C_{xylitol}$: the concentration of xylitol;
V: the total volume of the liquid obtained by the reaction;
n: the dilution factor;
$W^0_{xylose}$: the quality of xylose in the initial material;
$W_{xylose}$ and $W_{xylitol}$: the quality of xylose and xylitol after the reaction, respectively; and
$M_{xylose}$ and $M_{xylitol}$: the molecular weight of xylose and xylitol, respectively.

The hydrogenation experiment was carried out at different gas flow rates under the experimental conditions of a temperature of 140° C., the hydrogen pressure of 3.6 Mpa, the flow rate of the xylose solution of 1 ml/min, and a xylose solution concentration of 10% (here, the ratio of the mass of xylose to the mass of the xylose aqueous solution). The specific experimental data is shown in Table 8.

TABLE 8

Effect of gas flow rate on the reaction

| Gas flow rate (ml/min) | One-way conversion rate (%) | One-way selectivity (%) |
|---|---|---|
| 0 | 82.2 | 90.0 |
| 5 | 85.5 | 85.4 |
| 10 | 92.2 | 80.4 |
| 15 | 94.2 | 78.8 |
| 20 | 98.2 | 75.7 |

Embodiment Nine

The sugar solution hydrogenation experiment was carried out under different concentrations of xylose solution, and the effect of the concentration of xylose solution on the hydrogenation reaction of sugar solution was explored. The operation steps and experimental results of the xylose hydrogenation experiment were same as Embodiment Eight.

Under the experimental conditions of the temperature of 120° C., the hydrogen pressure of 2.0 Mpa, the gas flow rate of 20 ml/min and a flow rate of xylose solution of 1 ml/min, hydrogenation experiments were carried out at different concentrations of xylose solution (here, the ratio of the mass of xylose to the mass of xylose aqueous solution). The specific experimental data is shown in Table 9.

TABLE 9

Effect of substrate concentration on reaction

| Substrate concentration (%) | One-way conversion rate (%) | One-way selectivity (%) |
|---|---|---|
| 1 | 69.0 | 77.6 |
| 5 | 95.7 | 76.7 |
| 10 | 96.8 | 75.7 |
| 15 | 96.9 | 73.4 |
| 20 | 98.8 | 70.2 |

Embodiment Ten

The sugar solution hydrogenation experiment was carried out at different reaction temperatures, and the influence of reaction temperature on the hydrogenation reaction of sugar solution was explored. The operation steps and experimental results of the xylose hydrogenation experiment were same as Embodiment Eight.

The hydrogenation experiment was carried out at different reaction temperatures under the experimental conditions of a hydrogen pressure of 2.0 Mpa, the gas flow rate of 20 ml/min and the xylose solution concentration of 10% and a xylose solution flow rate of 1 ml/min. The specific experimental data is shown in Table 10.

TABLE 10

Effect of reaction temperature on the reaction

| Temperature (° C.) | One-way conversion rate (%) | One-way selectivity (%) |
|---|---|---|
| 100 | 58.6 | 85.2 |
| 110 | 77.3 | 85.4 |
| 120 | 85.3 | 81.3 |
| 130 | 95.8 | 76.7 |
| 140 | 99.1 | 72.5 |

Embodiment Eleven

The hydrogen liquid hydrogenation experiment was carried out under different hydrogen pressures, and the effect of hydrogen pressure on the hydrogenation reaction of sugar solution was explored. The operation steps and experimental results of the xylose hydrogenation experiment were same as Embodiment Eight.

The hydrogenation experiment was carried out under different hydrogen pressure conditions under the experimental conditions of a reaction temperature of 120° C., the gas flow rate of 5 ml/min and the xylose solution concentration of 10% and a flow rate of xylose solution of 1 ml/min. The specific experimental data is shown in Table 11.

TABLE 11

Effect of hydrogen pressure on the reaction

| Hydrogen pressure (MPa) | One-way conversion rate (%) | One-way selectivity (%) |
|---|---|---|
| 0.3 | 59.7 | 70.6 |
| 0.6 | 62.7 | 77.9 |
| 0.8 | 75.8 | 77.0 |
| 1.0 | 82.5 | 80.4 |
| 1.6 | 83.3 | 85.8 |
| 2.0 | 85.0 | 89.0 |
| 2.6 | 85.8 | 89.3 |
| 3.0 | 86.6 | 89.9 |
| 3.6 | 87.0 | 87.2 |

Embodiment Twelve

The sugar solution hydrogenation experiment was carried out under different xylose flow rates, and the effect of the flow rate of xylose solution on the hydrogenation reaction of sugar solution was explored. The operation steps and experimental results of the xylose hydrogenation experiment were same as Embodiment Eight.

Under the experimental conditions of a reaction temperature of 120° C., the hydrogen partial pressure of 3.6 Mpa, the gas flow rate of 5 ml/min. and xylose solution concentration of 20%, hydrogenation experiments were carried out at different xylose solution flow rates. The specific experimental data is shown in Table 12.

TABLE 12

Effect of the flow rate of xylose solution on the reaction

| Xylose solution flow rate (ml/min) | One-way conversion rate (%) | One-way selectivity (%) |
|---|---|---|
| 0.5 | 86.0 | 85.2 |
| 1.0 | 87.0 | 87.2 |
| 1.5 | 74.7 | 78.5 |
| 2.0 | 73.6 | 84.1 |
| 2.5 | 67.0 | 89.1 |

Embodiment Thirteen

The sugar solution hydrogenation experiment was carried out with arabinose as a raw material at different concentrations of arabinose solution, and the effect of the concentration of arabinose solution on the hydrogenation reaction of sugar solution was explored. The operation steps and experimental results of the arabinose hydrogenation experiment were same as the eighth embodiment.

Under different experimental conditions of a temperature of 110° C., the hydrogen pressure of 0.8 Mpa, the gas flow rate of 20 ml/min and a flow rate of arabinose solution of 1 ml/min, hydrogenation experiments were carried out at different concentrations of arabinose solution (herein referred to as the mass of arabinose and the mass of aqueous arabinose solution). The specific experimental data is shown in Table 13.

TABLE 13

Effect of substrate concentration on the reaction

| Substrate concentration (%) | One-way conversion rate (%) | One-way selectivity (%) |
|---|---|---|
| 1 | 99.4 | 84.9 |
| 5 | 100.0 | 84.0 |
| 10 | 99.3 | 81.3 |
| 15 | 98.3 | 82.2 |
| 20 | 97.6 | 83.4 |

Embodiment Fourteen

The sugar solution hydrogenation experiment was carried out at different reaction temperatures, and the effect of reaction temperature on the hydrogenation reaction of arabinose liquid was explored. The operation steps and experimental results of the arabinose hydrogenation experiment were same as Embodiment Eight.

The hydrogenation experiment was carried out at different reaction temperatures under the experimental conditions of a hydrogen pressure of 0.8 Mpa, the gas flow rate of 20 ml/min, the arabinose solution concentration of 10% and a flow rate of the arabinose solution of 1 ml/min. The specific experimental data is shown in Table 14.

TABLE 14

Effect of reaction temperature on the reaction

| Reaction temperature (° C.) | One-way conversion rate (%) | One-way selectivity (%) |
|---|---|---|
| 100 | 93.9 | 83.2 |
| 110 | 99.3 | 85.1 |
| 120 | 99.3 | 81.3 |
| 130 | 99.4 | 74.6 |
| 140 | 99.5 | 68.2 |

Embodiment Fifteen

The effect of hydrogen pressure on the hydrogenation of arabinose was investigated by experimenting on the hydrogenation of sugar solution under different hydrogen pressures. The operation steps and experimental results of the arabinose hydrogenation experiment were same as Embodiment Eight.

The hydrogenation experiment was carried out under different hydrogen pressure conditions under the experimental conditions of a reaction temperature of 120° C., the gas flow rate of 20 ml/min and the arabinose solution concentration of 10% and a flow rate of the arabinose solution of 1 ml/min. The specific experimental data is shown in Table 15.

TABLE 15

Effect of reaction pressure on reaction

| Hydrogen pressure (MPa) | One-way conversion rate (%) | One-way selectivity (%) |
|---|---|---|
| 0.6 | 97.9 | 69.0 |
| 0.8 | 99.0 | 81.7 |
| 1.0 | 98.3 | 71.3 |
| 1.6 | 99.3 | 81.3 |
| 2.0 | 98.4 | 80.3 |
| 2.6 | 99.5 | 65.4 |

Embodiment Sixteen

The sugar solution hydrogenation experiment was carried out under different flow rates of arabinose solution to explore the effect of the flow rate of arabinose solution on the hydrogenation reaction of sugar solution. The operation steps and experimental results of the arabinose hydrogenation experiment were same as Embodiment Eight.

The hydrogenation experiment was carried out at different reaction rates of the arabinose solution under the experimental conditions of the reaction temperature of 120° C., the hydrogen partial pressure of 0.8 Mpa, the gas flow rate of 2.5 ml/min, and an arabinose solution concentration of 10%. The specific experimental data is shown in Table 16.

TABLE 16

Effect of material flow rate on the reaction

| Material flow rate (ml/min) | One-way conversion rate (%) | One-way selectivity (%) |
|---|---|---|
| 0.5 | 99.4 | 80.8 |
| 1.0 | 99.3 | 81.3 |
| 1.5 | 98.1 | 82.8 |
| 2.0 | 96.1 | 84.4 |
| 2.5 | 92.7 | 85.1 |

Embodiment Seventeen

The xylitol solution hydrocleavage experiment was carried out under different hydrogen pressures, and the effect of hydrogen pressure on the hydrocleavage reaction of xylitol solution was explored.

The experiment follows the following steps including:

1. filling 349.79 g of the copper-based catalyst and filler in a fixed bed reactor, connecting and sealing the device, opening the ventilation source, replacing the air in the reactor with hydrogen for 4 to 5 times, and checking for leaks;
2. turning on the power which causes the temperature to heat up if there is no air leakage, introducing a certain hydrogen pressure and keeping the pressure constant after the temperature reaches the reaction temperature;
3. pumping a certain concentration of raw materials into the trickle bed with a metering pump at a certain flow rate;
4. recording experimental data regularly since reaction may last for a period of time, and paying attention to emptying the reaction liquid in the gas-liquid separator;
5. analyzing the composition of the reaction solution by high performance liquid chromatography after the reaction is completed; and
6. turning off the hydrogen cylinder and each valve and turn off the power.

The concentration of the sugar solution was determined by Shimadzu LC-20AT liquid chromatograph. The detector was RID-10A refractive index, and the column was Shodex SC1011. With water as the mobile phase, the column temperature was 80° C., the flow rate was 1.0 ml/min, and the injection volume was 10 μl.

The experimental results were calculated by the area normalization method, and the conversion of the reaction and the selectivity of the product and the yield of the product were calculated through the percentage of the area of each component measured in the total peak area. The calculation formula is shown in Formula (5), Formula (6), and Formula (7):

$$X = \frac{A_0 - A}{A_0} \times 100\%, \quad (5)$$

$$S = \frac{B}{A_0 - A} \times 100\%, \quad (6)$$

and $$Y = \frac{B}{A_0} \times 100\%, \quad (7)$$

X: the reaction conversion rate;
S: the selectivity of the product;
Y: the yield of the product;
$A_0$: the sum of the peak areas of all the substances after the reaction;
A: the peak area of the raw material after the reaction;
B: the peak area of the product after the reaction.

Further, the xylose conversion ratio is a ratio of the amount of xylose converted by the reaction to the amount of initial xylose, and is calculated according to Formula (2). The xylitol selectivity is the ratio of the amount of xylitol produced by the reaction to the amount of converted xylose, and is calculated according to Formula (3).

Under the conditions of a reaction temperature of 200° C., the xylitol solution concentration of 10% and a feed rate of 1 ml/min and a tail gas flow rate of 200 ml/min, different hydrogen pressures were respectively set for the xylitol hydrogenation reaction. The experimental results are shown in Table 17.

TABLE 17

Effect of hydrogen pressure on the reaction

| Hydrogen pressure (MPa) | One-way conversion rate (%) | One-way 1,2-propanediol selectivity (%) | One-way glycerin selectivity (%) | One-way ethylene glycol selectivity (%) |
|---|---|---|---|---|
| 3 | 7.1 | 21.8 | 15.0 | 12.5 |
| 4 | 8.9 | 21.1 | 16.4 | 13.3 |
| 5 | 10.7 | 20.1 | 17.4 | 14.9 |
| 6 | 12.4 | 19.6 | 15.6 | 13.5 |
| 7 | 14.4 | 18.4 | 14.7 | 13.0 |

Embodiment Eighteen

The xylitol solution hydrocleavage experiment was carried out at different reaction temperatures, and the effect of reaction temperature on the hydrocleavage reaction of xylitol solution was explored. The experimental operation and experimental results analysis of xylitol solution hydrocleavage were same as Embodiment Seventeen.

Under the conditions of the hydrogen pressure of 6 Mpa, the xylitol solution concentration of 10%, the feed rate of 1 ml/min and the tail gas flow rate of 200 ml/min, different reaction temperatures were set for the xylitol hydrogenation reaction. The experimental results are shown in Table 18.

TABLE 18

Effect of reaction temperature on the reaction

| Reaction temperature (° C.) | One-way conversion rate (%) | One-way 1,2-propanediol selectivity (%) | One-way glycerin selectivity (%) | One-way ethylene glycol selectivity (%) |
|---|---|---|---|---|
| 195 | 19.0 | 35.9 | 14.0 | 14.1 |
| 205 | 21.6 | 36.4 | 12.5 | 14.7 |
| 215 | 25.7 | 37.0 | 11.0 | 15.4 |
| 225 | 27.8 | 37.4 | 10.0 | 16.0 |
| 235 | 29.2 | 38.0 | 9.6 | 16.3 |

Embodiment Nineteen

The xylitol solution hydrocleavage experiment was carried out under different xylitol solution concentrations, and the effect of xylitol solution concentration on the hydrocleavage reaction of xylitol solution was explored. The experimental operation and experimental results analysis of xylitol solution hydrocleavage were same as Embodiment Seventeen.

Under the conditions of the reaction temperature of 215° C., the hydrogen pressure of 6 Mpa, the feed rate of 1 ml/min and the tail gas flow rate of 200 ml/min, different concentrations of xylitol were respectively set for the xylitol hydrogenation reaction. The specific experimental data is shown in Table 19.

TABLE 19

Effect of xylitol concentration on the reaction

| Xylitol solution concentration (wt %) | One-way conversion rate (%) | One-way 1,2-propanediol selectivity (%) | One-way glycerin selectivity (%) | One-way ethylene glycol selectivity (%) |
| --- | --- | --- | --- | --- |
| 1 | 32.4 | 22.8 | 7.5 | 13.8 |
| 5 | 29.1 | 24.0 | 8.9 | 14.1 |
| 10 | 25.7 | 26.2 | 9.9 | 14.4 |
| 15 | 22.9 | 29.1 | 11.1 | 15.1 |
| 20 | 20.6 | 33.0 | 11.3 | 15.6 |

Embodiment Twenty

The xylitol solution hydrocleavage experiment was carried out at different feed rates, and the effect of feed rate on the hydrocleavage reaction of xylitol solution was explored. The experimental operation and experimental results analysis of xylitol solution hydrocleavage were same as Embodiment Seventeen.

Under the conditions of the reaction temperature of 215° C., the xylitol solution concentration of 20%, the hydrogen pressure of 6 Mpa and the tail gas flow rate of 200 ml/min, different feed rates were set for the xylitol hydrogenation reaction. The specific experimental data is shown in Table 20.

TABLE 20

Effect of xylitol solution flow rate on xylitol cleavage

| Xylitol solution flow rate (ml/min) | One-way conversion rate (%) | One-way 1,2-propanediol selectivity (%) | One-way glycerin selectivity (%) | One-way ethylene glycol selectivity (%) |
| --- | --- | --- | --- | --- |
| 0.5 | 40.7 | 25.6 | 16.5 | 14.4 |
| 1.0 | 25.7 | 21.2 | 13.5 | 11.4 |
| 1.5 | 16.7 | 18.9 | 12.0 | 9.7 |
| 2.0 | 12.8 | 16.7 | 10.4 | 8.3 |
| 2.5 | 9.5 | 15.3 | 9.2 | 7.8 |

Embodiment Twenty-One

The sorbitol solution was used as the hydrocleavage raw material, and the sorbitol solution hydrocleavage experiment was carried out under different hydrogen pressures. The effect of hydrogen pressure on the hydrocleavage reaction of sorbitol solution was explored. The experimental operation and experimental results analysis of sorbitol solution hydrocleavage were same as Embodiment Seventeen.

The reaction temperature was 225° C., the feed rate was 1 ml/min, and the tail gas flow rate was 200 ml/min, respectively, and different hydrogen pressures were set to carry out the sorbitol cracking reaction. The specific experimental data is shown in Table 21.

TABLE 21

Effect of hydrogen pressure on the reaction

| Hydrogen pressure (MPa) | One-way conversion rate (%) | One-way 1,2-propanediol selectivity (%) | One-way glycerin selectivity (%) | One-way ethylene glycol selectivity (%) |
| --- | --- | --- | --- | --- |
| 4 | 12.5 | 39.3 | 14.6 | 9.5 |
| 5 | 15.6 | 41.0 | 12.2 | 9.5 |
| 6 | 19.9 | 41.6 | 11.4 | 10.6 |
| 7 | 20.4 | 40.6 | 12.8 | 9.1 |
| 8 | 20.8 | 39.8 | 13.1 | 9.0 |

Embodiment Twenty-Two

The hydrocleavage experiment of sorbitol solution was carried out at different reaction temperatures, and the effect of reaction temperature on the hydrocleavage reaction of sorbitol solution was explored. Wherein, the experimental operation and experimental results analysis of sorbitol solution hydrocleavage were same as Embodiment Seventeen.

Under the conditions of a hydrogen pressure of 6 MPa, a sorbitol solution concentration of 10%, a feed rate of 1 ml/min, and a tail gas flow rate of 200 ml/min, different reaction temperatures were set to carry out the sorbitol hydrogenation reaction. Specific experimental data is shown in Table 22.

TABLE 22

Effect of reaction temperature on the reaction

| Reaction temperature (° C.) | One-way conversion rate (%) | One-way 1,2-propanediol selectivity (%) | One way glycerin selectivity (%) | One-way ethylene glycol selectivity (%) |
| --- | --- | --- | --- | --- |
| 195 | 6.5 | 41.8 | 12.3 | 11.5 |
| 205 | 12.8 | 47.4 | 8.7 | 16.5 |
| 215 | 15.8 | 47.4 | 9.9 | 15.7 |
| 225 | 19.5 | 47.5 | 10.4 | 15.6 |
| 235 | 25.4 | 40.8 | 10.5 | 17.0 |

The basic concept has been described above, and it is obvious to those skilled in the art that the above disclosure is by way of example only and does not constitute a limitation of the present disclosure. Various modifications, improvements, and corrections of the present disclosure may be made by those skilled in the art, although not explicitly stated herein. Such modifications, improvements, and corrections are suggested in the present disclosure, so such modifications, improvements, and corrections are still within the spirit and scope of the exemplary embodiments of the present disclosure.

At the same time, the present disclosure uses specific words to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware apparatus, it may also be embodied in a software only, for example, the system described may be installed on an existing server or a mobile apparatus.

Similarly, it should be appreciated that in the foregoing description of embodiments of the present disclosure, various features are sometimes grouped together in a single embodiment, figure, or description thereof for the purpose of streamlining the present disclosure aiding in the understanding of one or more of the various embodiments. However, this disclosed method does not mean that the objects of the present disclosure requires more features than those mentioned in the claims. Rather, the features of the embodiments are less than all of the features of the single embodiment disclosed above.

In some embodiments, numbers describing the number of components and attributes are used. It should be understood that"about", "approximate" or "substantially" are used to modify such numbers for the description of the embodiments in some examples. Unless otherwise stated, "about," "approximate," or "substantially" may indicate ±20% variation of the value it describes. Accordingly, in some embodiments, the numerical parameters set forth in the description and attached claims are approximations that may vary depending upon the desired properties sought to be obtained by a particular embodiment. In some embodiments, the specified significant digits may be considered for the numerical parameters and the general digit retention method may be used. Although numerical fields and parameters used to confirm the breadth of its range in some embodiments of the present disclosure are approximate, such numerical values are set to be as accurate as possible within the feasible range in a particular embodiment.

Each patent, patent application, patent application publication and other materials cited herein, such as articles, books, instructions, publications, documents, or the like, are hereby incorporated by reference in their entirety. Application history documents that are inconsistent or conflicting with the contents of the present disclosure are excluded, and documents (currently or later attached to the present disclosure) that limit the widest range of the scope of the present disclosure are also excluded. It is to be noted that if the description, definition, and/or terminology used in the accompanying materials of the present disclosure are inconsistent or conflicting with the contents described in the present disclosure, the description, definition and/or terminology may be subject to the present disclosure.

At last, it should be understood that the embodiments described in the present disclosure are merely illustrative of the principles of the embodiments of the present disclosure. Other modifications may be within the scope of the present disclosure. Thus, by way of example, but not of limitation, alternative configurations of the embodiments of the present disclosure may be utilized in accordance with the teachings herein. Accordingly, embodiments of the present disclosure are not limited to the embodiments that are expressly introduced and described herein.

We claim:

1. A method for biological object degradation comprising:
providing a first biological object;
providing a catalyst that forms a mixture with the biological object, the catalyst including a component including copper and an auxiliary agent having a particle size in a range of 0.5 mm to 32 mm, a mass percentage of the component including copper being in a range of 4.8% to 100% and a mass percentage of the auxiliary agent being in a range of 0% to 95.2%; and
obtaining a first liquid phase and a first solid phase by heating the mixture in an atmosphere including hydrogen, the first liquid phase including a sugar.

2. The method of claim 1, wherein the catalyst includes at least one of copper, copper oxide, or cuprous oxide.

3. The method of claim 1, wherein the auxiliary agent is silica.

4. The method of claim 1, further comprising pre-processing the first biological object.

5. The method of claim 4, wherein the pre-processing of the first biological object includes at least one of cutting, pulverizing, grinding, or drying.

6. The method of claim 1, further comprising filtering the mixture.

7. The method of claim 1, wherein a mass ratio of the catalyst to the first biological object is in a range of 1:100 to 200:100.

8. The method of claim 1, wherein the atmosphere including hydrogen has a pressure in a range of 1.0 MPa to 6.0 MPa.

9. The method of claim 8, wherein the atmosphere including hydrogen has a pressure in a range of 1.0 MPa to 4.0 MPa.

10. The method of claim 1, wherein the heating of the mixture is carried out in a range of 100° C. to 170° C.

11. The method of claim 1, wherein the heating of the mixture lasts for a period of time that is in a range of 0.5 hour to 20.0 hours.

12. The method of claim 1, wherein the mixture is stirred during the heating of the mixture.

13. The method of claim 12, a stirring speed is in a range of 400 rpm to 800 rpm.

14. The method of claim 1, further comprising operations including:
providing a second biological object;
mixing the second biological object with the first solid phase; and
obtaining a second liquid phase and a second solid phase by heating the second biological object and the first solid phase in the atmosphere including hydrogen, the second liquid phase including the sugar.

15. A system for biological object degradation, comprising a first reactor, the first reactor comprising:
a first chamber configured to place a mixture that includes a biological object and a catalyst, the catalyst including a component including copper and an auxiliary agent having a particle size in a range of 0.5 mm to 32 mm, a mass percentage of the component including copper being in a range of 4.8% to 100% and a mass percentage of the auxiliary agent being in a range of 0% to 95.2%, the first chamber being in an atmosphere including hydrogen;

a first feed port configured to deliver the mixture;

a first heating device configured to heat the mixture to obtain a first liquid phase and a first solid phase, the first liquid phase including a sugar, the first solid phase including the catalyst;

a first discharge port configured to discharge the first liquid phase; and a second discharge port configured to discharge the first solid phase.

16. The system of claim 15, further comprising a stirring device.

17. The system of claim 15, further comprising a second reactor, the second reactor comprising:

a second chamber configured to place a second mixture that at least includes the first solid phase;

a second feed port;

a second heating device configured to heat the second mixture to obtain a second liquid phase and a second solid phase, the second liquid phase including the sugar, the second solid phase including the catalyst;

a third discharge port configured to discharge the second liquid phase; and a fourth discharge port configured to discharge the second solid phase;

wherein the second discharge port is connected with the second feed port, and second feed port is configured to receive the first solid phase from the second discharge port.

18. A catalyst for biological object degradation comprising:

a component including copper, a mass percentage of the component including copper being in a range of 4.8% to 100%; and an auxiliary agent having a particle size in a range of 0.5 mm to 32 mm, a mass percentage of the auxiliary agent being in a range of 0% to 95.2%.

19. The catalyst of claim 18, wherein the auxiliary agent is silica.

* * * * *